US011547698B2

(12) United States Patent
Yang et al.

(10) Patent No.: US 11,547,698 B2
(45) Date of Patent: Jan. 10, 2023

(54) ARYL HYDROCARBON RECEPTOR MODULATORS

(71) Applicant: ARIAGEN, INC., Menlo Park, CA (US)

(72) Inventors: Luqing Yang, Shenzhen (CN); Guodong Li, Shenzhen (CN); Suoming Zhang, Shenzhen (CN)

(73) Assignee: ARIAGEN, INC., Menlo Park, CA (US)

( * ) Notice: Subject to any disclaimer, the term of this patent is extended or adjusted under 35 U.S.C. 154(b) by 0 days.

(21) Appl. No.: 16/473,616

(22) PCT Filed: Dec. 22, 2017

(86) PCT No.: PCT/CN2017/118004
§ 371 (c)(1),
(2) Date: Jun. 25, 2019

(87) PCT Pub. No.: WO2018/121434
PCT Pub. Date: Jul. 5, 2018

(65) Prior Publication Data
US 2019/0330201 A1 Oct. 31, 2019

(30) Foreign Application Priority Data
Dec. 26, 2016 (CN) ......................... 201611216889.2

(51) Int. Cl.
*C07H 19/044* (2006.01)
*C07D 401/06* (2006.01)
(Continued)

(52) U.S. Cl.
CPC ........ *A61K 31/4245* (2013.01); *A61K 31/404* (2013.01); *A61K 31/4025* (2013.01);
(Continued)

(58) Field of Classification Search
None
See application file for complete search history.

(56) References Cited

U.S. PATENT DOCUMENTS 3,946,029 A 3/1976 Descamps et al.
4,046,774 A 9/1977 Napier
(Continued)

FOREIGN PATENT DOCUMENTS

CN 102573470 A 7/2012
CN 102850324 A 1/2013
(Continued)

OTHER PUBLICATIONS

International search report of PCT/CN2017/118004.
Written opinion of PCT/CN2017/118004.
Ro/101 of PCT/CN2017/118004.
Giuseppe La Regina et al. New Arylthioindoles and Related Bioisosteres at the Sulfur Bridging Group. 4. Synthesis, Tubulin Polymerization, Cell Growth Inhibition, and Molecular Modeling Studies. Journal of Medicinal Chemistry. Jul. 14, 2009 (Jul. 14, 2009), 52(23), ISSN: 0022-2623,pp. 7512-7527.
Abbs Fen Reji T. F. et al. Synthesis and cytotoxicity studies of thiazole analogs of the anticancer marine alkaloid dendrodoine. Indian Journal of Chemistry, Section B: Organic Chemistry Including Medicinal Chemistry. Dec. 2, 2011 (Dec. 2, 2011), 47B(7), ISSN: 0376-4699, pp. 1145-1150.
(Continued)

*Primary Examiner* — Traviss C McIntosh, III
(74) *Attorney, Agent, or Firm* — Steptoe & Johnson LLP

(57) ABSTRACT

The disclosure discloses an aryl hydrocarbon receptor modulators of formula (I), and pharmaceutically acceptable salts, (I)

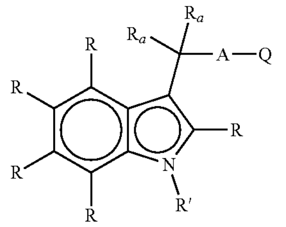

R' is H, CN, $CH_2(OH)R_0$, $C_mH_{2m+1}$, $C_nH_{2n-1}$, $C_nH_{2n-3}$,

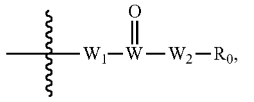

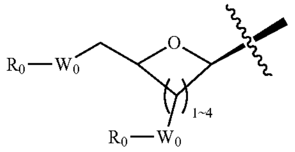

or

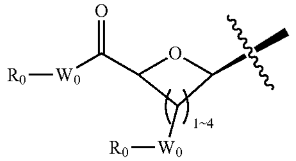

;

two $R_a$ is independently H, or two $R_a$ together form =O or =N—$W_3$—$R_1$; A is a $C_6$ to $C_{10}$ aromatic ring, or a $C_2$ to $C_{10}$ heteroaromatic ring containing 1 to 5 heteroatom from N, O and S, or 4 to 7 membered non-aromatic heterocyclic ring containing 1 to 3 heteroatom from N, O and S and C=N, which are with no substituent or substituted by 1 or 3 R; Q is R, or a $C_6$ to $C_{10}$ aromatic ring or a $C_2$ to $C_{10}$ heteroaromatic ring containing 1 to 5 heteroatom selected from N, O and S, which are with no substituent or substituted by 1 or 3 R; R is $R_c$ connected with C or $R_N$ connected with N.

13 Claims, No Drawings

(51) Int. Cl.

| | |
|---|---|
| ***C07D 403/06*** | (2006.01) |
| ***C07D 409/06*** | (2006.01) |
| ***C07D 413/06*** | (2006.01) |
| ***C07D 417/06*** | (2006.01) |
| ***C07D 417/10*** | (2006.01) |
| ***C07D 417/14*** | (2006.01) |
| ***A61K 31/4245*** | (2006.01) |
| ***A61P 35/04*** | (2006.01) |
| ***A61K 31/404*** | (2006.01) |
| ***A61K 31/4196*** | (2006.01) |
| ***A61K 31/427*** | (2006.01) |
| ***A61K 31/433*** | (2006.01) |
| ***A61K 31/437*** | (2006.01) |
| ***A61K 31/497*** | (2006.01) |
| ***A61K 31/5377*** | (2006.01) |
| ***A61K 31/7056*** | (2006.01) |
| ***A61K 31/506*** | (2006.01) |
| ***A61K 31/4025*** | (2006.01) |
| ***A61P 35/00*** | (2006.01) |
| ***C07D 209/12*** | (2006.01) |
| ***A61K 31/4178*** | (2006.01) |
| ***A61K 31/4439*** | (2006.01) |
| ***C07D 419/14*** | (2006.01) |

(52) U.S. Cl.

CPC ...... *A61K 31/4178* (2013.01); *A61K 31/4196* (2013.01); *A61K 31/427* (2013.01); *A61K 31/433* (2013.01); *A61K 31/437* (2013.01); *A61K 31/4439* (2013.01); *A61K 31/497* (2013.01); *A61K 31/506* (2013.01); *A61K 31/5377* (2013.01); *A61K 31/7056* (2013.01); *A61P 35/00* (2018.01); *A61P 35/04* (2018.01); *C07D 209/12* (2013.01); *C07D 401/06* (2013.01); *C07D 403/06* (2013.01); *C07D 409/06* (2013.01); *C07D 413/06* (2013.01); *C07D 417/06* (2013.01); *C07D 417/10* (2013.01); *C07D 417/14* (2013.01); *C07D 419/14* (2013.01); *C07H 19/044* (2013.01)

(56) References Cited

U.S. PATENT DOCUMENTS

| | | | | |
|---|---|---|---|---|
| 6,916,834 | B2 * | 7/2005 | DeLuca .................. | A61P 17/14 514/365 |
| 7,002,019 | B2 | 2/2006 | DeLuca et al. | |
| 7,419,992 | B2 | 9/2008 | DeLuca et al. | |
| 8,586,550 | B2 * | 11/2013 | Lee ...................... | C07D 493/10 514/23 |
| 9,205,148 | B2 | 12/2015 | Langermann et al. | |
| 2002/0177594 | A1 | 11/2002 | Curtin et al. | |
| 2002/0183524 | A1 | 12/2002 | DeLuca et al. | |
| 2007/0043092 | A1 | 2/2007 | DeLuca et al. | |
| 2008/0221070 | A1 | 9/2008 | William et al. | |
| 2010/0197708 | A1 | 8/2010 | Talley et al. | |
| 2012/0214853 | A1 | 8/2012 | Song | |
| 2013/0338201 | A1 | 12/2013 | Song | |
| 2020/0354353 | A1 | 11/2020 | Colabuono et al. | |

FOREIGN PATENT DOCUMENTS

| | | | | |
|---|---|---|---|---|
| EP | 1842541 | A1 | 3/2006 | |
| GB | 1318300 | | 5/1973 | |
| WO | WO 1998/039330 | | 9/1998 | |
| WO | WO 2002/028832 | | 4/2002 | |
| WO | 02064138 | | 8/2002 | |
| WO | WO 2003/068742 | A1 | 8/2003 | |
| WO | WO 2003/105847 | A1 | 12/2003 | |
| WO | WO 2004/060888 | | 7/2004 | |
| WO | WO 2006/029862 | | 3/2006 | |
| WO | WO 2008/019357 | A1 | 2/2008 | |
| WO | WO 2009/067349 | | 5/2009 | |
| WO | WO 2009/070645 | | 6/2009 | |
| WO | WO 2009/117597 | | 9/2009 | |
| WO | WO 2010/089327 | | 8/2010 | |
| WO | WO 2011/053466 | A1 | 5/2011 | |
| WO | WO 2012/015914 | | 2/2012 | |
| WO | WO 2012/145493 | | 10/2012 | |
| WO | WO 2013/033003 | | 3/2013 | |
| WO | WO 2013/041468 | | 3/2013 | |
| WO | WO 2013/116182 | A1 | 8/2013 | |
| WO | WO2013/163279 | | 10/2013 | |
| WO | WO-2014116182 | A1 * | 7/2014 | ............. B66B 1/468 |
| WO | WO 2015/035606 | | 3/2015 | |
| WO | WO 2015/112800 | | 7/2015 | |
| WO | WO 2015/112900 | | 7/2015 | |
| WO | WO2015/131035 | | 9/2015 | |
| WO | WO2016/023106 | | 2/2016 | |
| WO | WO 2016/040553 | A1 | 3/2016 | |
| WO | WO 2016/092419 | | 6/2016 | |
| WO | WO2018/085348 | | 5/2018 | |
| WO | WO 2018/153893 | | 8/2018 | |
| WO | WO 2019/057744 | | 3/2019 | |
| WO | WO 2019/099977 | A1 | 5/2019 | |

OTHER PUBLICATIONS

Chem. Rev., 2002, 102, 4303; Chem. Rev., 2012, 112, 3193; J. Biol.chem. 2009, 284, 2690.

Br. J. Cancer, 2003, 88, 599; Mal.Cancer Ther. 2004, 3, 1565.

Proc. Natl. Acad. Sci. 2002, 99, 14694-9; CN102573470; W02016040553.

Baud'Huin et al., "Factor VIII-von Willebrand factor complex inhibits osteoclastogenesis and controls cell survival," J Biol Chem. 284(46):31704-13 (2009).

Funcke et al, "The effect of alkyl substitution in drugs-IV. pharmacological properties of tropinyl 2-methyl-benzhydryl ether hydrobromide (BS 6825)," Journal of Medicinal and Pharmaceutical Chemistry 4(2): 215-224 (1961).

Gruber et al., "Correlation between the tumoral expression of β3-integrin and outcome in cervical cancer patients who had undergone radiotherapy," Br. J. Cancer 92(1):41-46 (2005).

King, "Bioisosteres, conformational restriction, and pro-drugs—case history: an example of a conformational restriction approach," Med Chem Principle and Practice 206-208 (1994).

Knölker et al., "Isolation and synthesis of biologically active carbazole alkaloids," Chem Rev. 102(11):4303-427 (2002).

Leong et al., "In vitro, in vivo, and in silico analyses of the antitumor activity of 2-(4-amino-3-methylphenyl)-5-fluorobenzothiazoles," Mol Cancer Ther 3(12):1565-75 (2004).

McDougal, "Methyl-substituted diindolylmethanes as inhibitors of estrogen-induced growth of T47D cells and mammary tumors in rats," Breast Cancer Research and Treatment 66:147-157 (2001).

Medjakovic et al., "Indolylfuran, a potent aryl hydrocarbon receptor agonist from sauerkraut, interacts with the oestrogen pathway," Food Chemistry 127(4):1764-1772 (2011).

Schmidt et al., "Occurrence, biogenesis, and synthesis of biologically active carbazole alkaloids," Chem. Rev. 112:6:3193-3328 (2012).

Song et al., "A ligand for the aryl hydrocarbon receptor isolated from lung," Proc Natl Acad Sci USA 99(23):14694-9 (2002).

Trapani et al., "DNA damage and cell cycle arrest induced by 2-(4-amino-3-methylphenyl)-5-fluorobenzothiazole (5F 203, NSC 703786) is attenuated in aryl hydrocarbon receptor deficient MCF-7 cells," Br J Cancer. 88(4):599-605 (2003).

Veale et al., "Synthesis and MRSA PK inhibitory activity of thiazole containing deoxytopsentin analogues," Tetrahedron 70:43:7845-7853 (2014).

Wille et al., "Malassezin—A novel agonist of the arylhydrocarbon receptor from the yeast Malassezia furfur," Bioorg Med Chem. 9(4):955-60 (2001).

Wincent et al., "The suggested physiologic aryl hydrocarbon receptor activator and cytochrome P4501 substrate 6-formylindolo[3,2-b] carbazole is present in humans," J Biol Chem. 284(5):2690-6(2009).

(56) References Cited

OTHER PUBLICATIONS

Zhang et al., "Induction of cytochromes P450 1A1 and 1A2 by tanshinones in human HepG2 hepatoma cell line," Toxicol Appl Pharmacol. 252(1):18-27 (2011).
Zhang et al., "A novel assay for screening inhibitors targeting HIV integrase LEDGF/p75 interaction based on $Ni^{2+}$ coated magnetic agarose beads," Sci Rep. 6:33477 (2016).
Cavalluzzo et al., "De novo design of small molecule inhibitors targeting the LEDGF/p75-HIV integrase interaction," RSC Advances 2:974-984 (2012).
Akahoshi et al., "Synthesis, structure-activity relationships, and pharmacokinetic profiles of nonpeptidic α-Keto Heterocycles as novel inhibitors of human chymase," J. Med. Chem. 44:1286-1296 (2001).
Alarma-Estrany et al., "Design of novel melatonin analogs for the reduction of intraocular pressure in normotensive rabbits," J Pharmacol Exp Ther 337(3):703-9 (2011).
Bankoti et al., "Functional and phenotypic effects of AhR activation in inflammatory dendritic cells," Toxicol Appl Pharmacol 246:18-28 (2010).
Bermúdez et al., "Beta-naphthoflavone represses dystrophin Dp71 expression in hepatic cells," Biochim. Biophys. Acta. 1759(3-4):152-158 (2006).
Bock et al., "Ah receptor- and TCDD-mediated liver tumor promotion: clonal selection and expansion of cells evading growth arrest and apoptosis," Biochem. Pharmacol. 69(10):1403-1408 (2005).
Boldron et al., "N-[6-(4-Butanoyl-5-methyl-1H-pyrazol-1-yl) pyridazin-3-yl]-5-chloro-1-[2-(4-methylpiperazin-1-yl)-2-oxoethyl]-1H-indole-3-carboxamide (SAR216471), a Novel Intravenous and Oral, Reversible, and Directly Acting P2Y12 Antagonist," Journal of Medical Chemistry 57(17):7293-7316 (2014).
Brauze et al., "The effect of aryl hydrocarbon receptor ligands on the expression of AhR, AhRR, ARNT, Hif1alpha, CYP1A1 and NQO1 genes in rat liver," Toxicol. Lett. 167(3):212-220 (2006).
Brozic et al., "Selective inhibitors of aldo-keto reductases AKR1C1 and AKR1C3 discovered by virtual screening of a fragment library," J. Med. Chem 55(17):7417-24 (2012).
Cheng et al., "Tryptophan derivatives regulate the transcription of Oct4 in stem-like cancer cells." Nat Commun 6:7209 (2015).
Cook et al., "Angiogenesis Inhibitors: Current Strategies and Future Prospects," http://cajournal.org (2010).
Crestey et al., "Design and synthesis of a new indazole library: direct conversion of N-methoxy-N-methylamides (Weinreb amides) to 3-keto and 3-formylindazoles," Tetrahedron 63(2):419-428 (2007).
Dickson et al., "Rapid synthesis of indole cis-enamides via hydroamidation of indolic alkynes," Tetrahed Letts 54(38):5239-42 (2013).
Dietrich et al., "The aryl hydrocarbon receptor (AhR) in the regulation of cell-cell contact and tumor growth," Carcinogenesis 31(8):1319-1328 (2010).
Dolciami et al., "Binding Mode and Structure-Activity Relationships of ITE as Aryl Hydrocarbon Receptor (AhR) Agonist," ChemMedChem 13(3):270-279 (2018).
Dorbritsa et al., "Development of a High-Throughput Cell-Based Assay for Identifcation of IL-17 Inhibitors," Journal of Biomolecular Screening 18(1):75-84 (2013).
Duarte et al., "Differential influences of the aryl hydrocarbon receptor on Th17 mediated responses in vitro and in vivo," PLoS One 8:079819 (2013).
Ebos et al., "Accelerated metastasis after short-term treatment with a potent inhibitor of tumor angiogenesis," Cancer Cell 15(3):232-239 (2009).
Elizondo et al., "Altered cell cycle control at the G(2)/M phases in aryl hydrocarbon receptor-null embryo fibroblast," Mol Pharmacol 57(5):1056-63 (2000).
Ellis, "Role of Angiogenesis Inhibitors in Cancer Treatment," Oncology 15:39-46 (2001).
Emtenäs et al., "An enantioselective ketene-imine cycloaddition method for synthesis of substituted ring-fused 2-pyridinones," J Org Chem 66(20):6756-61 (2001).
English et al., "VEGF inhibition and metastasis: possible implications for antiangiogenic therapy," Cancer Biol. Ther. 8(13):1214-1225 (2009).
Forrester et al., "Induction of a chloracne phenotype in an epidermal equivalent model by 2,3,7,8-tetrachlorodibenzo-p-dioxin (TCDD) is dependent on aryl hydrocarbon receptor activation and is not reproduced by aryl hydrocarbon receptor knock down," J Dermatol Sci 73:10-22 (2014).
Fritz et al., "The selective aryl hydrocarbon receptor modulator 6-methyl-1,3,8-trichlorodibenzofuran inhibits prostate tumor metastasis in TRAMP mice," Biochem. Pharmacol. 77(7):1151-1160 (2009).
Fuganti et al., "A general method for the synthesis of the most powerful naturally occurring Maillard flavors," Tetrahedron 63:4762-4767 (2007).
Gierthy et al., "Correlation of in vitro and in vivo growth suppression of MCF-7 human breast cancer by 2,3,7,8-tetrachlorodibenzo-p-dioxin," Cancer Res 53(13):3149-3153 (1993).
Gluschnaider et al., "beta-TrCP inhibition reduces prostate cancer cell growth via upregulation of the aryl hydrocarbon receptor," PLoS One 5(2):e9060 (2010).
Grzywacz et al., "A concise synthesis of an AHR endogenous ligand with the indolecarbonylthiazole skeleton," Heterocycles 60:5:1219 (2003).
Hall et al., "Activation of the Aryl-Hydrocarbon Receptor Inhibits Invasive and Metastatic Features of Human Breast Cancer Cells and Promotes Breast Cancer Cell Differentiation," Mol Endocrinol 24:359-369 (2010).
Hao et al., "Inhibitory effect and its mechanism of ITE, an endogenous aryl hydrocarbon receptor (AhR) ligand, on the proliferation of human placental trophoblast cells," Fudan Univ J Med Sci 41:488-493 (2014).
Hawerkamp et al., "Vemurafenib acts as an aryl hydrocarbon receptor antagonist: Implications for inflammatory cutaneous adverse events," Allergy. 74(12):2437-2448 (2019).
Henry et al., "A potential endogenous ligand for the aryl hydrocarbon receptor has potent agonist activity in vitro and in vivo," Arch. Biochem. Biophys. 450(1):67-77 (2006).
Henry et al., "TCDD and a Putative Endogenous AhR Ligand, ITE, Elicit the Same Immediate Changes in Gene Expression in Mouse Lung Fibroblasts," Toxicological Sciences 114:90-100 (2010).
Heravi et al., "An efficient synthesis of thiazol-2-imine derivatives via a onepot, three-component reaction," Tetrahedron Letters 53:392-394 (2012).
Holcomb et al., "Inhibition of 7,12-dimethylbenzanthracene-induced rat mammary tumor growth by 2,3,7,8-tetrachlorodibenzo-p-dioxin," Cancer Lett 82(1):43-7 (1994).
Hu et al., "Synthetic RORg agonists regulate multiple pathways to enhance antitumor immunity," Oncoimmunology 5(12) (2016).
Ishida et al., "Activation of the aryl hydrocarbon receptor pathway enhances cancer cell invasion by upregulating the MMP expression and is associated with poor prognosis in upper urinary tract urothelial cancer," Carcinogenesis 31(2):287-295 (2010).
Jana et al., "Cross-talk between 2,3,7,8-tetrachlorodibenzo-p-dioxin and testosterone signal transduction pathways in LNCaP prostate cancer cells," Biochem Biophys Res Commun 256(3):462-8 (1999).
Jin et al., "Copper-catalyzed oxidative cross-coupling of H-phosphonates and amides to N-acylphosphoramidates," Organic Letters 15(2) (2013).
John et al., "Antiangiogenic therapy and surgical practice," Br J Surg 95(3):281-293 (2008).
Johnson, et al., "Total synthesis of (−)-Rhazinilam: asymmetric C—H bond activation via the use of chiral auxiliary," J. Am. Chem. Soc. 124:6900-6903 (2002).
Jux et al., "Langerhans cell maturation and contact hypersensitivity are impaired in aryl hydrocarbon receptor-null mice," J. Immunol. 182(11):6709-6717 (2009).
Kajta et al., "Aryl hydrocarbon receptor-mediated apoptosis of neuronal cells: a possible interaction with estrogen receptor signaling," Neuroscience 158(2):811-822 (2009).
Kang et al., "Genome-wide transcriptional profiling of human glioblastoma cells in response to ITE treatment," Genomics Data 5:281-283 (2015).

(56) References Cited

OTHER PUBLICATIONS

Katner, "An Improved Synthesis of Indole-3-Carboxylic Acids," Organic Preparations and Procedures 2(4):297-303 (1970).
Kashani et al., "Expression of the aryl hydrocarbon receptor (AhR) and the aryl hydrocarbon receptor nuclear translocator (ARNT) in fetal, benign hyperplastic, and malignant prostate," Prostate 37(2):98-108 (1998).
Kawajiri, et al., "Aryl hydrocarbon receptor suppresses intestinal carcinogenesis in ApcMin/+ mice with natural ligands," Proc. Natl. Acad. Sci. U.S.A. 106(32):13481-13486 (2009).
Kerbel, "Tumor angiogenesis: past, present and the near future," Carcinogenesis 21:505-515 (2000).
Knerr et al., "Carcinogenicity of 2,3,7,8-tetrachlorodibenzo-p-dioxin in experimental models," Mol Nutr Food Res 50(10):897-907 (2006).
Koliopanos et al., "Increased aryl hydrocarbon receptor expression offers a potential therapeutic target for pancreatic cancer," Oncogene 21(39):6059-70 (2002).
Kurihara et al., "Synthesis and Cycloaddition Reaction of 2-Cyano-3-indoleacetonitriles," Chemical & Pharmaceutical Bulletin 34(11) (1986).
Lehmann et al., "The Aryl Hydrocarbon Receptor Ligand ITE Inhibits TGFβ1-Induced Human Myofibroblast Differentiation," Am J Pathol 178(4):1556-1567 (2011).
Lin et al., "Overexpression of aryl hydrocarbon receptor in human lung carcinomas," Toxicol Pathol 31(1):22-30 (2003).
Liu et al., "AhR expression is increased in hepatocellular carcinoma," J Mol Histol 44(4):455-61 (2013).
Loges et al., "Silencing or fueling metastasis with VEGF inhibitors: antiangiogenesis revisited," Cancer Cell 15(3):167-170 (2009).
Loughlin et al., "Approaches to the high-throughput synthesis of analogues of dihydroaeruginoic acid," Aust. J. Chem 53:6:457-462 (2000).
Manegold et al., "The Potential of Combined Immunotherapy and Antiangiogenesis for the Synergistic Treatment of Advanced NSCLC," J Thorac Oncol. 12(2):194-207 (2017).
Marlowe et al., "The aryl hydrocarbon receptor displaces p300 from E2F-dependent promoters and represses S phase-specific gene expression," J Biol Chem 279(28):29013-22 (2004).
McDougal et al., "Tamoxifen-induced antitumorigenic/antiestrogenic action synergized by a selective aryl hydrocarbon receptor modulator," Cancer Res 61(10):3902-3907 (2001).
McDougal et al., "Inhibition of 7,12-dirnethylbenz [a] anthracene-induced rat mammary tumor growth by aryl hydrocarbon receptor agonists," Cancer Lett 120(1):53-63 (1997).
Milen et al., "A study on the phosphorylation of indole, imidazole, carbazole, and phenothiazine derivatives," Phosphorus, Sulfur and Silicon and the Related Elements 187(9) (2012).
Milinkevich et al., "Synthesis of 5-(Thiazol-5-yl)-4,5-dihydroisoxazoles from 3-Chloropentane-2,4-dione," J. Comb. Chem. 10:521-525 (2008).
Miyagi et al., "Binding affinity between AhR and exogenous/endogenous ligands: molecular simulations and biological experiment," Molecular Simulation 41(7) (2015).
Miyake et al., "Synthesis of 5-(3-indo1y1) oxazole natural products. Structure revision of A1mazo1e D," Tetrahed 66(26):4888-4893 (2010).
Mizzoni et al., "Some thiazolines and thiazolidinones with antituberculous activity," (Jul. 5, 1958).
Mjambili et al., "Synthesis and biological evaluation of 2-aminothiazole derivatives as antimycobacterial and antiplasmodial agents," Biorganic & Medicinal Chemistry Letters 24:560-564 (2014).
Morrow et al., "Aryl hydrocarbon receptor-mediated inhibition of LNCaP prostate cancer cell growth and hormone-induced transactivation," J. Steroid Biochem. Mol. Biol. 88(1):27-36 (2004).
Mouchlis et al., "Molecular docking and 3D-QSAR CoMFA studies on indole inhibitors of GIIA secreted phospholipase A(2)," Chem Inf Model 50(9):1589-1601 (2010).
Murray et al., "Aryl hydrocarbon receptor ligands in cancer: friend and foe," Nat Rev Cancer 14(12):801-14 (2014).
Narender et al., "Aqueous phase synthesis of thiazoles and aminothiazoles in the presence of β-cyclodextrin," Tetrahedron letters 46:5953-5955 (2005).
Neumann et al., "Exploring the oxidative cyclization of substituted N-aryl enamines: Pd-catalyzed formation of indoles from anilines," Chem. Eur. J 17(26):7298-7303 (2011).
Nugent et al., "ITE, A Novel Endogenous Nontoxic Aryl Hydrocarbon Receptor Ligand, Efficiently Suppresses EAU and T-Cell-Mediated Immunity," Invest Ophthalmol Vis Sci 54:7463-7469 (2013).
O'Donnell et al., "The aryl hydrocarbon receptor mediates leflunomide-induced growth inhibition of melanoma cells," PLoS One 7(7) (2012).
Oenga et al., "TCDD and PCBs inhibit breast cancer cell proliferation in vitro," Toxicol in Vitro. 18(6):811-9 (2004).
Okino et al., "Toxic and chemopreventive ligands preferentially activate distinct aryl hydrocarbon receptor pathways: implications for cancer prevention," Cancer Prev Res (Phila Pa). 2(3):251-256 (2009).
Ott et al., "Inhibition of immune checkpoints and vascular endothelial growth factor as combination therapy for metastatic melanoma: an overview of rationale, preclinical evidence, and initial clinical data," Frontiers in Oncology, 5:1-7 (2015).
Ozawa et al., "A new synthesis of glutathione via the thiazoline peptide," Bull. Chem. Soc. Jpn., 53:2592-2593 (1980).
Paez-Ribes et al., "Antiangiogenic therapy elicits malignant progression of tumors to increased local invasion and distant metastasis," Cancer Cell 15(3):220-231 (2009).
Park et al., "The aryl hydrocarbon receptor predisposes hepatocytes to Fas mediated apoptosis," Mol Pharmacol. 67(3):612-22 (2005).
Patani et al., "Bioisosterism: A Rational Approach to Design," Chemical Reviews 96(8):3147-3176 (1996).
Peng et al., "Potential therapeutic significance of increased expression of aryl hydrocarbon receptor in human gastric cancer," World J. Gastroenterol. 15(14):1719-1729 (2009).
Piparo et al., "Virtual screening for aryl hydrocarbon receptor binding prediction," J Med Chem 49(19):5702-5709 (2006).
Poellinger, "Mechanistic aspects—the dioxin (aryl hydrocarbon) receptor," Food Addit Contam 17(4):261-6 (2000).
Poland et al., "2,3,7,8-tetrachlorodibenzo-p-dioxin and related halogenated aromatic hydrocarbons: examination of the mechanism of toxicity," Annu. Rev. Pharmacol. Toxicol. 22:517-554 (1982).
Potewar et al., "Efficient synthesis of 2,4-disubstituted thiazoles using ionic liquid under ambient conditions: a practical approach towards the synthesis of Fanetizole," Tetrahedron 63:45:11066-11069 (2007).
Puga et al., "Ah receptor signals cross-talk with multiple developmental pathways," Biochem Pharmacol. 69(2):199-207 (2005).
Puga et al., "Role of the aryl hydrocarbon receptor in cell cycle regulation," Toxicology 181-182:171-7 (2002).
Quintana et al., "Control of T(reg) and T(H)17 cell differentiation by the aryl hydrocarbon receptor," Nature 453(7191):65-71 (2008).
Quintana et al., "An endogenous aryl hydrocarbon receptor ligand acts on dendritic cells and T cells to suppress experimental autoimmune encephalomyelitis," Proc Natl Acad Sci U S A 107:20768-73 (2010).
Quintana et al., "Aryl Hydrocarbon Receptor Control of Adaptive Immunity," Pharmacol Rev. 65(4):1148-61 (2013).
Radspieler, "Studies on the synthesis of diazonamide A and phorbazol A and C," Sel. Org. React. Database (SORD), no pp. given (2007).
Rajniak, et al., "A new cyanogenic metabolite in *Arabidiposis* required for inducible pathogen defense," Nature 525(7569):376-379 (2015).
Ramanjulu et al., "Design of amidobenzimidazole STING receptor agonists with systemic activity," Nature 564(7736):439-443 (2018).
Ramjiawan et al., "Anti-angiogenesis for cancer revisited: Is there a role for combinations with immunotherapy?" Angiogenesis. 20(2):185-204 (2017).
Rasool et al., "Convenient one-pot synthesis and biological evaluation of phosphoramidates and phosphonates containing heterocycles," Phosphorus, Sulfur and Silicon and the Related Elements 193(7) (2018).

(56) References Cited

OTHER PUBLICATIONS

Ray et al., "Activation of the aryl hydrocarbon receptor by TCDD inhibits senescence: a tumor promoting event?" Biochem. Pharmacol 77(4):681-688 (2009).
Rose, "A theory of the action of cancer chemotherapeutic drugs," Clin. Exp. Immunol. 2:361-373 (1967).
Safe et al., "Mechanism of action and development of selective aryl hydrocarbon receptor modulators for treatment of hormone dependent cancers," Int J Oncol 20(6):1123-1128 (2002).
Sanderson et al., "2,3,7,8-Tetrachlorodibenzo-p-dioxin and diindolylmethanes differentially induce cytochrome P450 1A1, 1B1, and 19 in H295R human adrenocortical carcinoma cells," Toxicol. Sci. 61(1):40-48 (2001).
Schmidt, "Developing combination strategies using PD-1 checkpoint inhibitors to treat cancer," Semin Immunopathol. 41(1):21-30 (2019).
Schulz et al., "Activation of the aryl hydrocarbon receptor suppresses sensitization in a mouse peanut allergy model," Toxicol Sci 123:491-500 (2011).
Shih et al., "Bevacizumab: an angiogenesis inhibitor for the treatment of solid malignancies," Clin Ther (11): 1779-802 (2006).
Shiizaki et al., "Identification of amino acid residues in the ligand-binding domain of the aryl hydrocarbon receptor causing the species-specific response to omeprazole: possible determinants for binding putative endogenous ligands," Molecular Pharmacology Fast Forward (2013).
Simon et al., "Estimates of cancer potency of 2,3,7,8-tetrachlorixlibenzo(p)dioxin using linear and nonlinear dose-response modeling and toxicokinetics," Toxicological sciences 112(2):490-506 (2009).
Simones et al., "Consequences of AhR Activation in Steady-State Dendritic Cells," Toxicological Sciences 119:293-307 (2011).
Singh et al. "Primary peripheral T cells become susceptible to 2,3,7,8-tetrachlorodibenzo-p-dioxin-mediated apoptosis in vitro upon activation and in the presence of dendritic cells," Mol. Pharmacol. 73(6):1722-1735 (2008).
Smith et al., "Tapinarof is a natural AhR agonist that resolves skin inflammation in mice and humans," J Invest Dermatol. 137(10):2110-2119 (2017).
Solankee, et al., "Thiazoline: synthesis and antitubercular activity of 2-Alkyl/Aryl/-5-(w-carboxy pentyl) thiazolin-4-one," Part II, J. Inst. Chemists (India) vol. 66 (1994).
Stevens et al., "The aryl hydrocarbon receptor: a perspective on potential roles in the immune system," Immunology 127(3):299-311 (2009).
Sutter et al., "EGF receptor signaling blocks aryl hydrocarbon receptor mediated transcription and cell differentiation in human epidermal keratinocytes," Proc. Natl. Acad. Sci. U.S.A. 106(11):4266-4271 (2009).
Tchaicha et al., "Abstract 4131: Overcoming aryl hydrocarbon receptor mediated tumor immunosuppression," Immunology, 4131-4131 (2019).
Tsai et al., "Aryl hydrocarbon receptor (AhR) agonists increase airway epithelial matrix metalloproteinase activity," J Mol Med 92:615-628 (2014).
Van Zandt et al., "Discovery of 3-[(4,5,7-Trifluorobenzothiazol-2-yl)methyl]indole-N-acetic acid (lidorestat) and congeners as highly potent and selective inhibitors of aldose reductase for treatment of chronic diabetic complications," J. Med. Chem. 48:3141-3152 (2005).
Veldhoen et al., "The aryl hydrocarbon receptor links TH17-cell-mediated autoimmunity to environmental toxins," Nature 453(7191):106-109 (2008).
Wang et al., "The first design and synthesis of [11C]MKC-1 ([11C]Ro 31-7453), a new potential PET cancer imaging agent," Nucl Med Biol 37(7):763-75 (2010).
Wang et al., "The first synthesis of [(11)C]SB-216763, a new potential PET agent for imaging of glycogen synthase kinase-3 (GSK-3)," Bioorg Med Chem Lett 21(1):245-9 (2011).
Wang, et al., "An endogenous aryl hydrocarbon receptor ligand inhibits proliferation and migration of human ovarian cancer cells," Cancer Letters 340:63-71 (2013).
Wang et al., "Activation of the aryl hydrocarbon receptor affects activation and function of human monocyte-derived dendritic cells," Clinical and Experimental Immunology 177:521-530 (2014).
Wang et al., "Decreased Expression of the Aryl Hydrocarbon Receptor in Ocular Behcet's Disease," Mediators Inflamm 2014:195094 (2014).
Wang et al., "Discovery of the Human Immunodeficiency Virus Type 1 (HIV-1) Attachment Inhibitor Temsavir and its Phosphonooxymethyl Prodrug Fostemsavir," J Med Chem. 61(14):6308-6327 (2018).
Wei et al., "Role of the Aryl Hydrocarbon Receptor in the Pathogenesis of Chronic Rhinosinusitis with Nasal Polyps," Inflammation 37:387-95 (2013).
Wei et al., "An aryl hydrocarbon receptor ligand acts on dendritic cells and T cells to suppress the Th17 response in allergic rhinitis patients," Laboratory Investigation 94:528-535 (2014).
Wei et al., "Increased aryl hydrocarbon receptor expression in patients with allergic rhinitis," QJM 107:107-113 (2014).
Wu et al., "ITE and TCDD Differentially Regulate the Vascular Remodeling of Rat Placenta via the Activation of AhR," PLoS One 9:e86549 (2014).
Yan et al., "Synthesis, evaluation, and mechanism study of novel indole-chalcone derivatives exerting effective antitumor activity through microtubule destabilization in vitro and in vivo," J. Med. Chem. 59(11) 5264-5283 (2016).
Yeste et al., "Nanoparticle-mediated codelivery of myelin antigen and a tolerogenic small molecule suppresses experimental autoimmune encephalomyelitis," Proc Natl Acad Sci U S A 109:11270-5 (2012).
Yeste et al., "IL-21 induces IL-22 production in CD4p T cells," Nat Commun. 5:3753 (2014).
Yeste et al., "Tolerogenic nanoparticles inhibit T cell-mediated autoimmunity through SOCS2," Sci Signal. 9(433):ra61 (2016).
Yoshida et al., "Effects of AhR ligands on the production of immunoglobulins in purified mouse B cells," Biomedical Research 33:67-74 (2012).
Yu et al., "In utero exposure of mice to dibenzo[a,l] pyrene produces lymphoma in the offspring: role of the aryl hydrocarbon receptor," Cancer Res 66(2):755-762 (2006).
Zhang et al., "A Simple Statistical Parameter for Use in Evaluation and Validation of High Throughput Screening Assays," J Biomol Screen 4(2):67-73 (1999).
Zhang et al., "The aryl hydrocarbon receptor as a target for estrogen receptor-negative breast cancer chemotherapy," Endocr Relat Cancer 16(3):835-844 (2009).
Zhang et al., "Activation of aryl hydrocarbon receptor suppresses invasion of esophageal squamous cell carcinoma cell lines," Tumori 98(1):152-157 (2012).
Zhang et al., "Rhodium(I)-catalyzed cycloisomerization of nitrogen-tethered indoles and alkylidenecyclopropanes: convenient access to polycyclic indole derivatives," Chemistry 19(41):13668-73 (2013).
Zhang et al., "A tryptophan derivative, ITE, enhances liver cell metabolic functions in vitro," Int J Mol Med. 39(1): 101-112 (2017).
Zhao et al., "Akt-mediated phosphorylation of Oct4 is associated with the proliferation of stem-like cancer cells," Oncology Reports 33:1621-1629 (2015).
Zimmerman et al., "N-substituted prodrugs of mebendazole provide improved aqueous solubility and oral bioavailability in mice and dogs," J Med Chem. 61(9):3918-3929 (2018).
"Fruit juice and medications don't mix," Consumer Reports News (Sep. 2, 2008).
Classic Bioelectronic isosteres.
USPTO, PTAB decision on the appeal of U.S. Appl. No. 13/954,834, 17 pages (May 30, 2018).

* cited by examiner

ARYL HYDROCARBON RECEPTOR MODULATORS

CROSS-REFERENCE TO RELATED APPLICATIONS

This application is a national stage application of PCT Application No. PCT/CN2017/118004. This Application claims priority from PCT Application No. PCT/CN2017/118004, filed Dec. 22, 2012, and CN Application No. 2016112168892, filed Dec. 26, 2016, the contents of which are incorporated herein in the entirety by reference.

Some references, which may include patents, patent applications, and various publications, are cited and discussed in the description of the present disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE INVENTION

The present disclosure relates to the field of anti-tumor compounds, and more particularly relates to a class of compounds which can modulate activity of aryl hydrocarbon receptor (AhR) and pharmaceutically acceptable salts thereof.

BACKGROUND OF THE INVENTION

Due to changes of environment and lifestyle, incidence of cancer increases with each passing day. Coupled with its high fatality rate, cancer is a serious threat to human's health. Although there has been significant progress in medical treatment of certain cancers and targeted drugs and immune therapy have improved survival rate of patients greatly, in the past 20 years, the total of 5 year survival rate of all cancer patients increased only 10% monthly. And due to resistance or uncontrolled migration and rapid growth of malignant tumors, detection and treatment of cancer are extremely difficult.

Aryl hydrocarbon receptor (AhR) is a kind of intracellular transcriptional regulatory factor which can sense stimulation of xenobiotic in external environment and mediate toxic reactions. AhR after activation can regulate expression of many genes in chromosome and promote decomposition of xenobiotic. Previous studies have shown that this signal is also involved in several important biological processes, such as signal transduction, cellular differentiation and apoptosis. Relationship between AhR and immune regulation has also been a hotspot of research. Previous research has shown that AhR can participate in differentiation and function of T cells, macrophages and DC. In addition, AhR also plays a key role in immune rejection reactions after organ transplantation. Study has found that to activate AhR in body of mice by use of dioxin can reduce their survival rate after viral infection and differentiation and proliferation rate of virus-specific COB8 T cells are also affected. For example, another compound of DIM and derivatives thereof have activity of inhibiting tumor (*Breast Cancer Res. Treat.* 2001, 66, 147). DIM is currently in phase II clinical trials for treatment of prostate cancer and cervical cancer. Natural products ICZ and FICZ are both AhR agonist, and can anti-asthmatic (*Chem. Rev.,* 2002, 102, 4303; *Chem. Rev.,* 2012, 112, 3193;

*J. Biol. Chem.* 2009, 284, 2690). Malassezin (*Bioorg. Med. Chem.* 2001, 9, 955). Aminoflavonone, developed by NCI, is in phase I clinical trials. 3-hydroxymethyl indole (indole-3-carbinol), in phase II clinical trials, is used as chemical protection agent and immune stimulant. Phortress is an AhR agonists developed by Pharminox Univ. of Nottingham, and is in phase I clinical trials for treatment of solid tumors (*Br. J. Cancer,* 2003, 88, 599; *Mal. Cancer Ther.* 2004, 3, 1565). Tanshinone I is a natural AhR ligand for antitumor chemoprotectant (*Toxicol Appl Pharmacol.* 2011 Apr. 1; 252 (1): 18-27). 2-(indolylacetyl-3-yl) furan (*Food Chem.* 2011, 127, 1764-1772). ITE is a natural endogenous AhR agonist having effect of anti-liver cancer, prostate cancer, breast cancer and ovarian cancer (*Proc. Natl. Acad. Sci.* 2002, 99, 14694-9; CN102573470; WO2016040553).

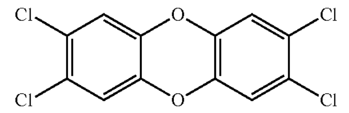

TCDD

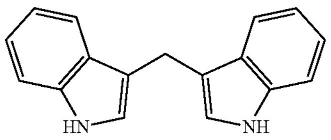

DIM

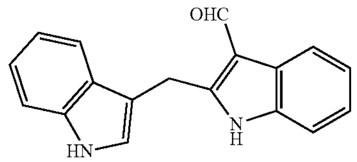

Malasserin

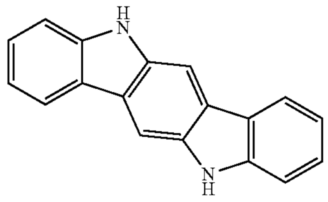

ICZ

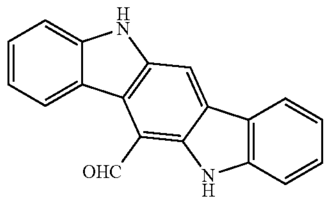

FICZ

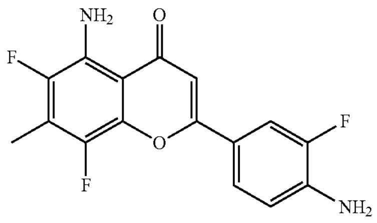

aminoflavonone

-continued

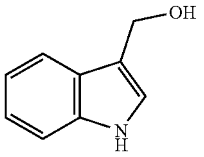

Indole-3-carbinol

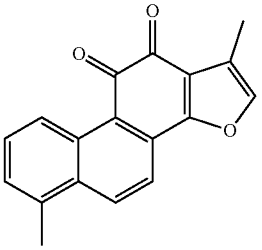

Tanshinone I

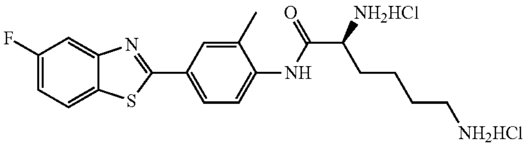

Phortress

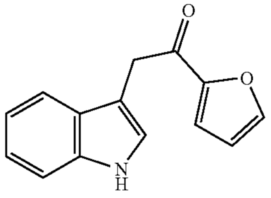

Indolylfuran

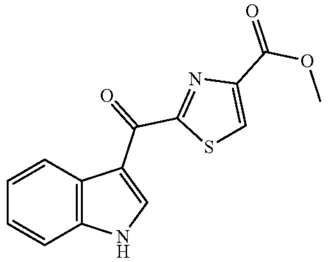

ITE

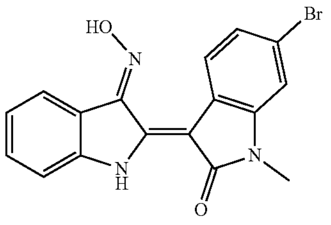

MeBio

SUMMARY OF THE INVENTION

An objective of the present disclosure is to provide a new kind of aryl hydrocarbon receptor modulators of formula (I) having AhR activity, and pharmaceutically acceptable salts thereof, (I)

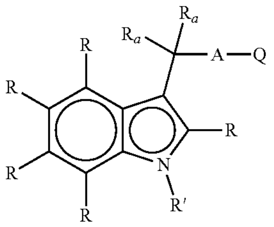

R' is H, CN, $CH_2(OH)R_0$, $C_mH_{2m+1}$, $C_nH_{2n-1}$, $C_nH_{2n-3}$,

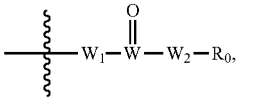

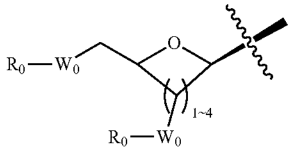

or

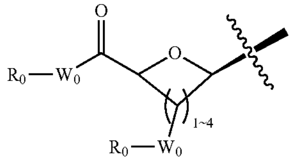

;

wherein, $W_0$ is O or NH; $W_1$ is bond; $C(R_0)_2$, $C(R_0)_2O$, $C(R_0)_2OC(R_0)_2$ or $C(R_0)_2OC(R_0)_2C(R_0)_2$; when W is C, S or S(O), $W_2$ is bond, O, $NR_0$, $CH(N(R_0)_2)$ or $OCH_2C(O)$; when W is $P(OR_0)$, $W_2$ is O or $NR_0$; each $R_0$ is independently H, $C_mH_{2m+1}$, $C_mH_{2m+1}OC(O)$, $C_mH_{2m+1-r}X_r$, $C_mH_{2m+1}OC(O)C_mH_{2m}$, (cyclic $C_4H_8NO)C_mH_{2m}$, $CH_3(OCH_2CH_2)_u$ or $CH_3(OCH_2CH_2)_uOCH_2$;

Two $R_a$ is independently H, or two $R_a$ together form =O, =N—CN or =N—$W_3$—$R_1$; when $W_3$ is O or NH, $R_1$ is H, $C_mH_{2m+1}$, $C_mH_{2m+1}C(O)$, $C_mH_{2m+1}OC(O)$ or $C_mH_{2m+1}S(O)_{1\sim2}$;

A is a $C_6$ to $C_{10}$ aromatic ring with no substituent or substituted by 1 or 3 R; or a $C_2$ to $C_{10}$ heteroaromatic ring containing 1 to 5 heteroatom selected from N, O and S, or 4 to 7 membered non-aromatic heterocyclic ring containing 1 to 3 heteroatom selected from N, O and S and containing C=N, which are with no substituent or substituted by 1 to 3 R;

Q is R, or $C_6$ to $C_{10}$ aromatic ring with no substituent or substituted by 1 to 3 R, or 3 to 10 membered, preferably 4 to 7 membered, more preferably 5 to 6 membered heterocyclic ring, preferably heteroaryl ring containing 1 to 5, preferably 1 to 3, more preferably 2 to 3 heteroatom selected N, O and S, which are with no substituent or substituted by 1 to 3 R;

R is $R_c$ connected with C or RN connected with N, wherein each $R_c$ is independently X, CN, R", —Y—OR", —Y—C(O)R", —Y—OC(O)R", —Y—C(O)OR", —Y—OC(O)OR", —Y—NR"$_2$, —Y—C(O)NR"$_2$, —Y—NR"C(O)R", —Y—NR"C(O)NR"$_2$, —Y—OC(O)NR"$_2$, —Y—NR"C(O)OR", —Y—S(O)$_{1\text{-}2}$R", —Y—S(O)$_{1\sim2}$NR"$_2$ or —Y—NR"S(O)$_{1\sim2}$R"; each RN is independently CN, R", —Y—OR", —Y—C(O)R", —Y—OC(O)R", —Y—C(O)OR", —Y—OC(O)OR", —Y—NR"$_2$, —Y—C(O)NR"$_2$, —Y—NR"C(O)R", —Y—NR"C(O)NR"$_2$, —Y—OC(O)

NR"$_2$, —Y—NR"C(O)OR", —Y—S(O)$_{1\sim2}$R", —Y—S(O)$_{1\text{-}2}$NR"$_2$ or —Y—NR"S(O)$_{1\sim2}$R";

R" is H, D, $C_mH_{2m+1}$, $C_nH_{2n-1}$, $C_nH_{2n-3}$, $C_mH_{2m+1-r}X_r$, $C_nH_{2n-1-s}X_s$ or $C_nH_{2n-3-t}X_t$;

Y is bond, —$C_mH_{2m}$—, —$C_mH_{2n-2}$—, —$C_nH_{2n-4}$—, —$C_mH_{2m-i}X_i$—, —$C_nH_{2n-2-j}X_j$— or —$C_nH_{2n-4-k}X_k$—;

m is 1 to 8, n is 2 to 8, u is 1 to 5, r≤2m+1, s≤2n-1, t≤2n-3, i≤2m, j≤2n-2, k≤2n-4, X is halogen; preferably, m is 1 to 5 more preferably 1 to 3, n is 2 to 6 more preferably 2 to 4, u is 1 to 4 more preferably 1 to 3, X is F, Cl or Br.

Wherein, the term "cyclic $C_4H_8NO$" in (cyclic $C_4H_8NO$) $C_mH_{2m}$ is a 6 membered ring in which atoms of N and O are arranged by meta or para arrangements, preferably morpholine substituted at N position.

$C_mH_{2m+1}$, $C_mH_{2m+1-r}X_r$, —$C_mH_{2m}$— and —$C_mH_{2m-i}X_i$— can be a straight-chain or branch-chain alkyl. $C_nH_{2n-1}$, $C_nH_{2n-1-s}X_s$, —$C_nH_{2n-2}$— and —$C_nH_{2n-2-j}X_j$— can be a straight-chain or branch-chain alkenyl. $C_nH_{2n-3}$, $C_nH_{2n-3-t}X_t$, —$C_nH_{2n-4}$— and —$C_nH_{2n-4-k}X_k$ can be a straight-chain or branch-chain alkynyl.

When n is 3 to 8, $C_nH_{2n-1}$, $C_nH_{2n-1-s}X_s$, —$C_nH_{2n-2}$— and —$C_nH_{2n-2-j}X_j$— can also be naphthenic group. When n is 5 to 8, $C_nH_{2n-3}$, $C_nH_{2n-3-t}X_t$, —$C_nH_{2n-4}$— and —$C_nH_{2n-4-k}X_k$ can also be dual-alkenyl or cyclic alkenyl.

In some preferable embodiments of the invention, when A is

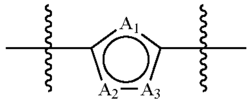, formula (I) turns into formula (I1), (I1)

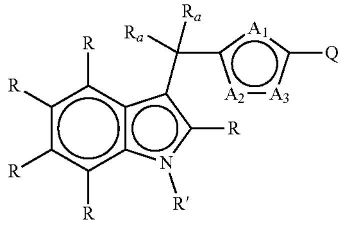

in formula (I1), one of $A_1$, $A_2$ and $A_3$ is O, S or N(R), the rest two are each independently C(R) or N. To be specific, it can be divided three classes, if $A_1$ is O, S or N(R), $A_2$ and $A_3$ is independently C(R) or N respectively; if $A_2$ is O, S or N(R), $A_1$ and $A_3$ is independently C(R) or N respectively; if $A_3$ is O, S or N(R), $A_1$ and $A_1$ is independently C(R) or N respectively.

On the base of formula (I1) of the invention, more preferably, one of $A_1$, $A_2$ and $A_3$ is O, S or N(R); the rest two ones are each independently N. At this moment, all of $A_1$, $A_2$ and $A_3$ are heteroatom. More preferably on the base of this, when $A_3$ is fixed to be N, the formula (I1) turns into formula (Ia)

(Ia)

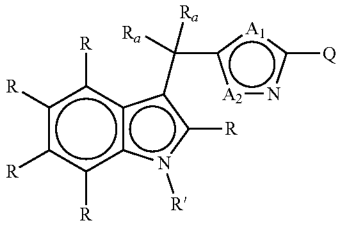

in formula (Ia), $A_1$ is O, S or N(R), $A_2$ is N; or $A_2$ is O, S and N(R), $A_1$ is N.

On the base of formula (I1) of the invention, more preferably, when $A_2$ is CH, formula (I1) turns into formula (Ib), (Ib)

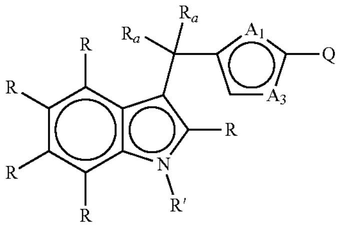

in formula (Ib), $A_1$ is N or C(R), $A_3$ is O, S or N(R); or $A_1$ is O, S or N(R), $A_3$ is N or C(R).

On the base of formula (I1) of the invention, more preferably, when $A_1$ is N, $A_3$ is C(R) and two $R_a$ together form =N—$W_3$—$R_1$ or H independently, at this moment, formula (I1) turns into formula (Ic) or formula (Id);

(Ic)

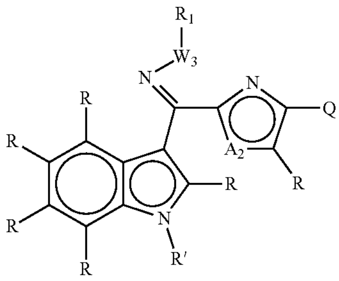

(Id)

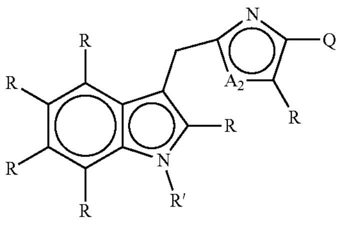

in formula (Ic) and formula (Id), $A_2$ is O, S or N(R).

On the base of formula (I1) of the invention, more preferably, when $A_1$ is N, $A_3$ is C(R) and R' is

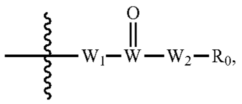

at this moment, formula (I1) turns into formula (Ie), (Ie)

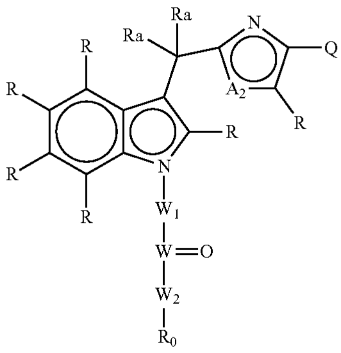

in formula (Ie), $A_2$ is O, S or N(R).

On the base of formula (I1) of the invention, more preferably, when $A_1$ is N, $A_3$ is C(R) and R' is

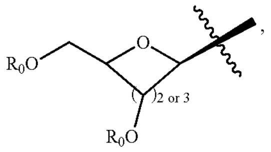

at this moment, formula (I1) turns into formula (If), (If)

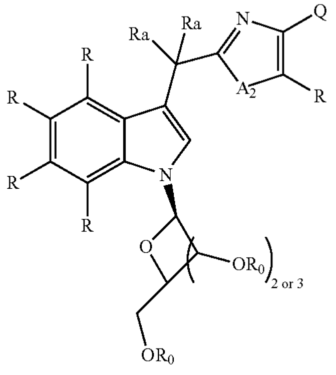

in formula (If), $A_2$ is O, S or N(R), each $R_0$ is independently H or Ac.

In some preferable embodiments of the invention, Q is

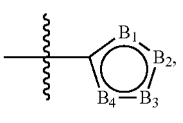

one of $B_1$, $B_2$, $B_3$ and $B_4$ is O, S or N(R), the rest three ones are each independently C(R) or N; that is to say, when $B_1$ is O, S or N(R), $B_2$, $B_3$ and $B_4$ are independently C(R) or N;

or when $B_2$ is O, S or N(R), B1, $B_3$ and B4 are independently C(R) or N;

or when $B_3$ is O, S or N(R), $B_1$, $B_2$ and B4 are independently C(R) or N;

or when $B_4$ is O, S or N(R), $B_1$, $B_2$ and $B_3$ are independently C(R) or N.

In some preferable embodiments of the invention, when Q is

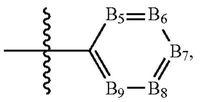

$B_5$ to $B_9$ are C(R), i.e. Q is a benzene ring; or one or two of $B_5$ to $B_9$ is N, the rest three ones are independently C(R), that is to say, Q can be a pyridine ring, at this moment, if $B_5$ is N, $B_6$ to $B_9$ are independently C(R); or if $B_6$ is N, $B_5$, $B_7$ to $B_9$ are independently C(R); or if $B_7$ is N, $B_5$, $B_6$, $B_8$ and $B_9$ are independently C(R);

Q can be a pyridazine ring, at this moment, if $B_5$ and $B_6$ are N respectively, $B_7$ to $B_9$ are independently C(R); or if $B_6$ and $B_7$ are N respectively, $B_5$, $B_8$ and $B_9$ are independently C(R);

Q can be a pyrimidine ring, at this moment, if $B^5$ and $B_7$ are N respectively, $B_6$, $B_8$ and $B_9$ are independently C(R);

Q can be a pyrazine ring, at this moment, if $B_5$ and $B_8$ are N respectively, $B_6$, $B_7$ and $B_9$ are independently C(R).

On the base of formula (I1) of the invention, more preferably, when $A_1$ is N, $A_2$ is S, $A_3$ is CH and Q is a 5 membered heteroaromatic ring, formula (I1) turns into formula (Ig), formula (Ig)

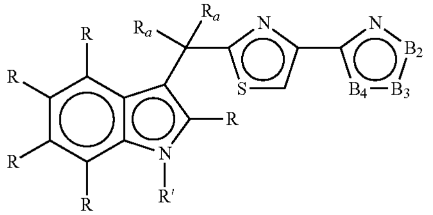

wherein one of $B_2$, $B_3$ and $B_4$ is O, S or N(R), the rest ones are each independently C(R) or N, that is to say, if $B_2$ is O, S or N(R), $B_3$ and $B_4$ are each independently C(R) or N;

if $B_3$ is O, S or N(R), $B_2$ and $B_4$ are each independently C(R) or N;

if $B_4$ is O, S or N(R), $B_2$ and $B_3$ are each independently C(R) or N.

On the base of formula (I1) of the invention, more preferably, when $A_1$ is N, $A_2$ is S, $A_3$ is CH and Q is a 5 membered heterocycle, at this moment, formula (I1) turns into formula (Ih), formula (Ih)

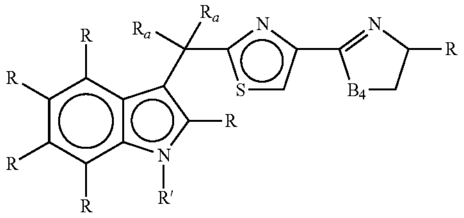

$B_4$ is O, S or N(R).

In some preferable embodiments of the invention, when A is a non-aromatic heterocyclic ring with N and S heteroatom and Q is R, formula (I) turns into formula (I2), formula (I2)

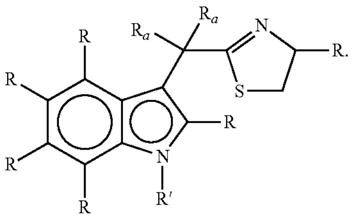

In some preferable embodiments of the invention, when A is

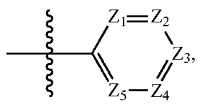

formula (I) turns into formula (I3), (I3)

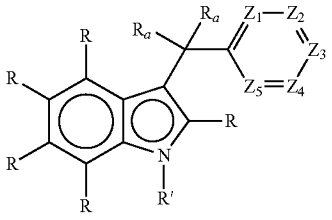

in formula (I3), $Z_1$ to $Z_5$ are independently C(Q), i.e. A is a benzene ring;

or, one or two of $Z_1$ to $Z_5$ are N, the rest ones are independently C(Q), i.e.

A can be a pyridine ring, at this moment, if $Z_1$ is N, $Z_2$ to $Z_5$ are independently C(Q); or if $Z_2$ is N, $Z_1$, $Z_3$ to $Z_5$ are independently C(Q); or if $Z_3$ is N, $Z_1$, $Z_2$, $Z_4$ and $Z_5$ are independently C(Q);

A can be a pyridazine ring, at this moment, if $Z_1$ and $Z_2$ are N respectively, $Z_3$ to $Z_5$ are independently C(Q); or if $Z_2$ and $Z_3$ are N respectively, $Z_1$, $Z_4$ and $Z_5$ are independently C(R);

A can be a pyrimidine ring, at this moment, $Z_1$ and $Z_3$ are N respectively, $Z_2$, $Z_4$ and $Z_5$ are independently C(Q);

A can be a pyrazine ring, at this moment, $Z_1$ and $Z_4$ are N respectively, $Z_2$, $Z_3$ and $Z_5$ are independently C(Q);

or, the two ones of $Z_1$ to $Z_5$ adjacent to each other is C(Q) and forms together a 5 to 6 membered carbocyclic ring or a 5 to 6 membered heterocyclic ring containing 1 to 3 heteroatom selected from N, O and S, the rest three ones each are independently C(Q), or two of the rest three ones are each independently C(Q), the last ones is N; or one of the rest three ones is C(Q), the rest two are independently N. According to position forming a ring, two kinds of situations can be classified:

when $Z_1$ and $Z_2$ is C(Q) and form a 5 to 6 carbon ring or a 5 to 6 heterocycle containing 1 to 3 heteroatom selected from N, O and S, $Z_3$ to $Z_5$ are independently C(Q), or $Z_3$ and $Z_4$ are independently C(Q) and $Z_5$ is N; or $Z_3$ and $Z_5$ are independently C(Q) and $Z_4$ is N; or $Z_4$ and $Z_5$ are independently C(Q) and $Z_3$ is N; or $Z_3$ is C(Q) and $Z_4$ and $Z_5$ are N independently; or $Z_4$ is C(Q) and $Z_3$ and $Z_5$ are N independently; or $Z_5$ is C(Q) and $Z_3$ and $Z_4$ are N independently;

when $Z_2$ and $Z_3$ is C(Q) and form a 5 to 6 carbon ring or a 5 to 6 heterocycle containing 1 to 3 heteroatom selected from N, O and S, $Z_1$, $Z_4$ and $Z_5$ are independently C(Q), or $Z_1$ and $Z_4$ are independently C(Q) and $Z_5$ is N; or $Z_1$ and $Z_5$ are independently C(Q) and $Z_4$ is N; or $Z_4$ and $Z_5$ are independently C(Q) and $Z_1$ is N; or $Z_1$ is C(Q) and $Z_4$ and $Z_5$ are N independently; or $Z_4$ is C(Q) and $Z_1$ and $Z_5$ are N independently; or $Z_5$ is C(Q) and $Z_1$ and $Z_4$ are N independently.

In some preferable embodiments of the invention, R' is

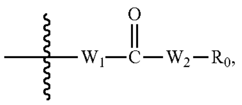

$W_1$ is bond, $C(R_0)_2O$ or $C(R_0)_2OC(R_0)_2$; $W_2$ is O or $CH(N(R_0)_2)R_0$.

In the embodiments, each functional group or radical can be selected optionally and combined in the scope of description, for example in formula (I), R' can be one selected from the following substituent:

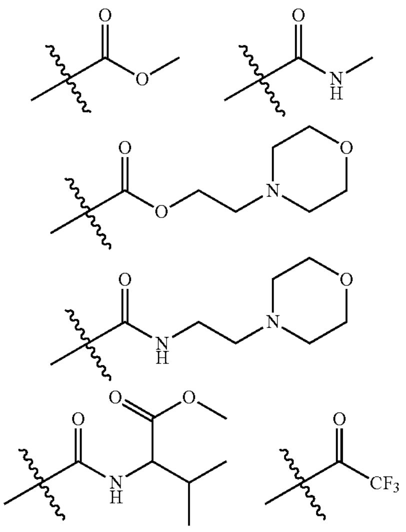

-continued
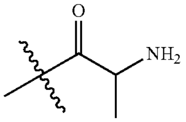
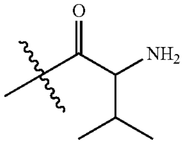
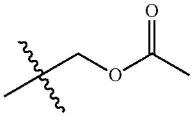
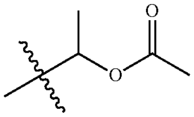
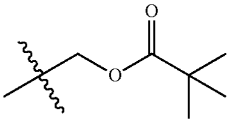
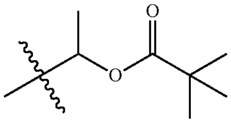
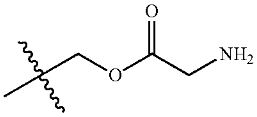
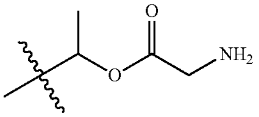
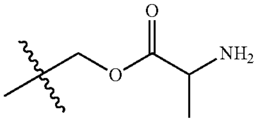
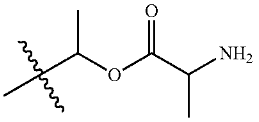
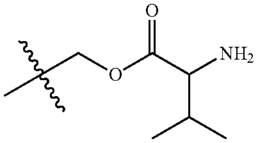
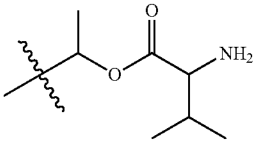
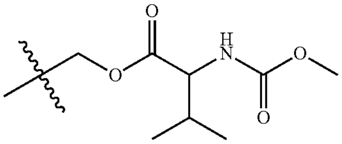
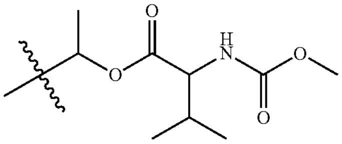
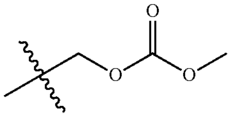
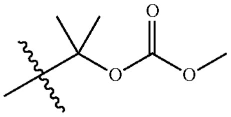
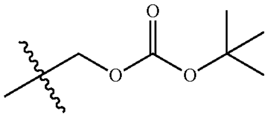
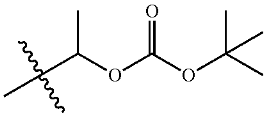
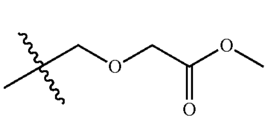
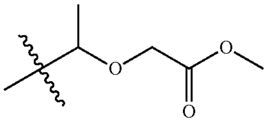
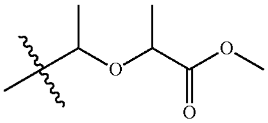
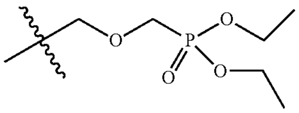
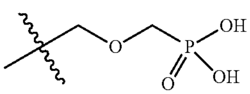
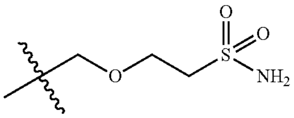
-continued
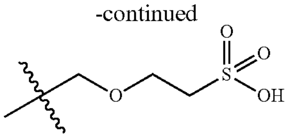
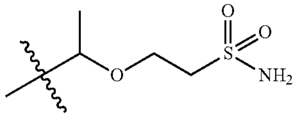
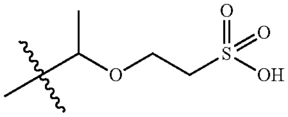
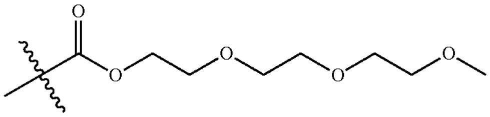
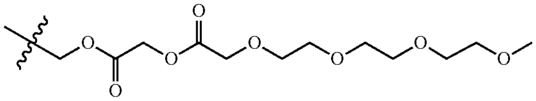
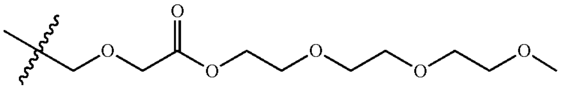
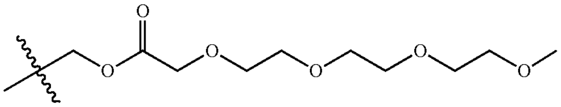
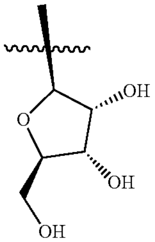
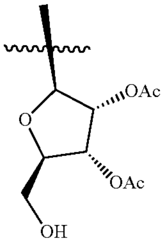
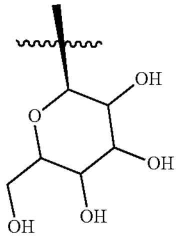
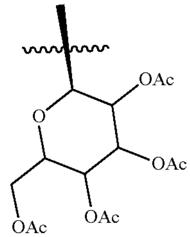
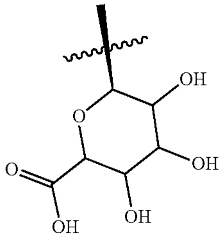
and
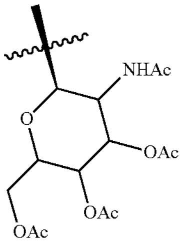
in formula (I1),
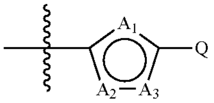

can be one selected from the following substituent:
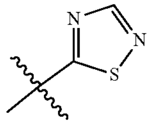
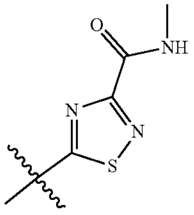
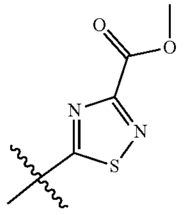
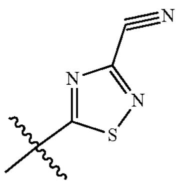
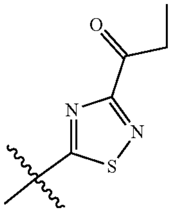
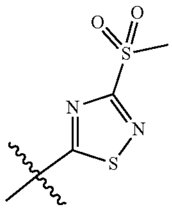
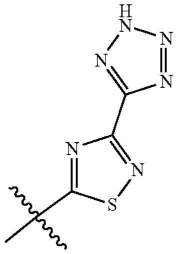
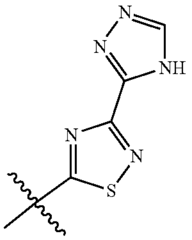
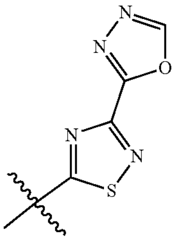
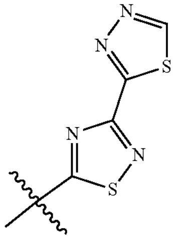
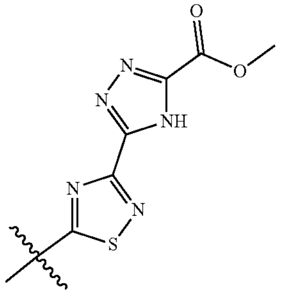
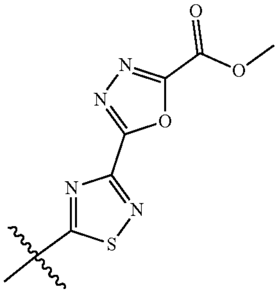
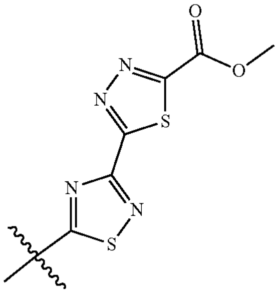
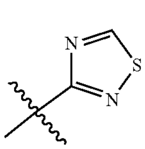
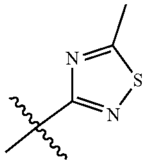
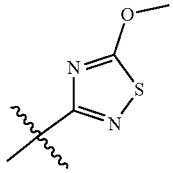
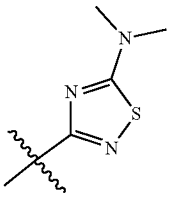
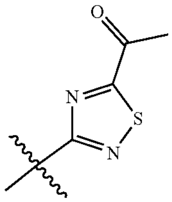
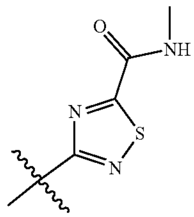
-continued
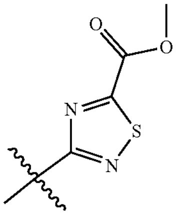
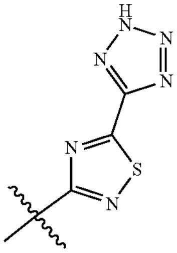
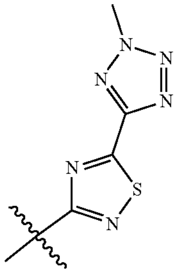
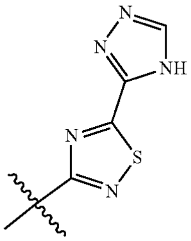
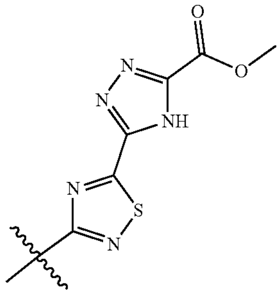
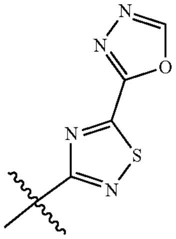
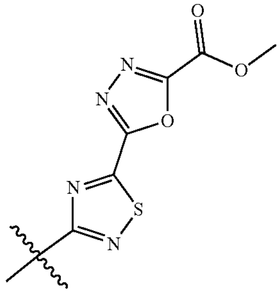
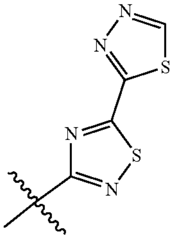
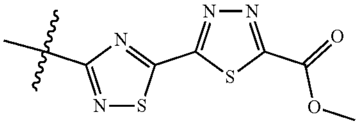
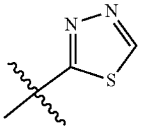
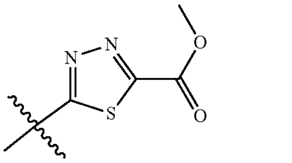
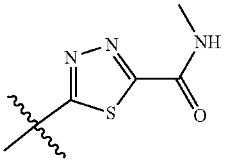
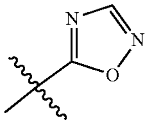
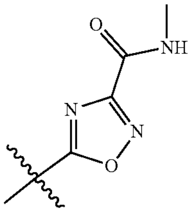
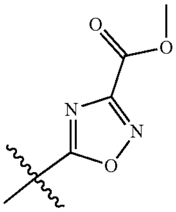
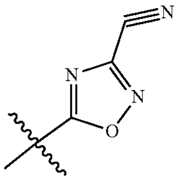

-continued
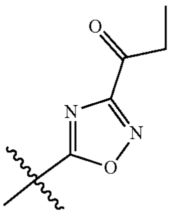
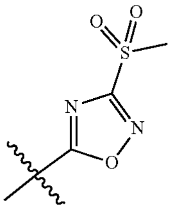
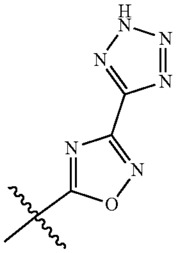
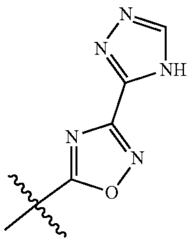
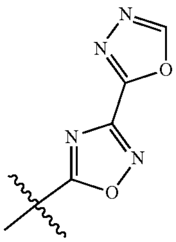
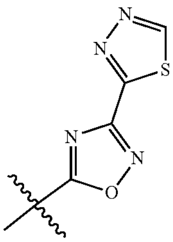
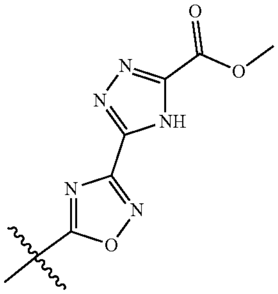
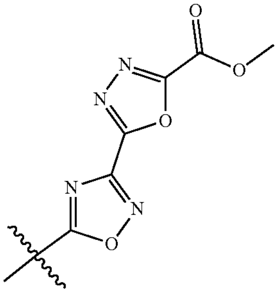
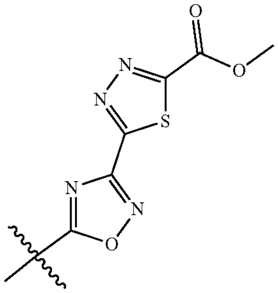
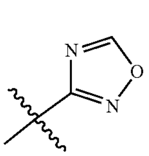
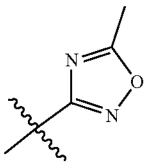
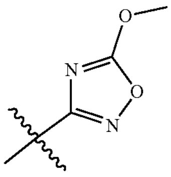
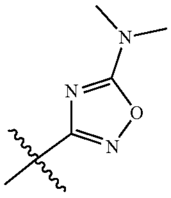
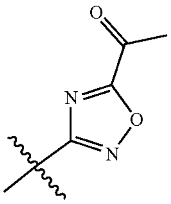
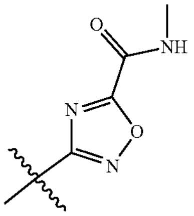
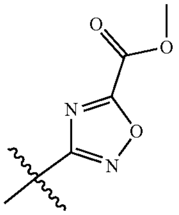
-continued
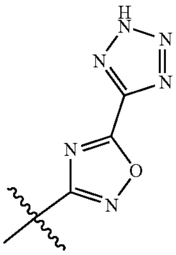
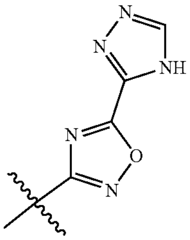
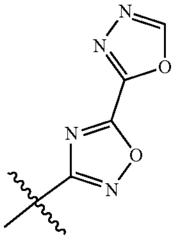
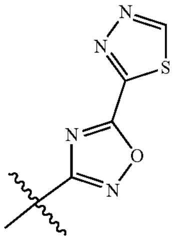
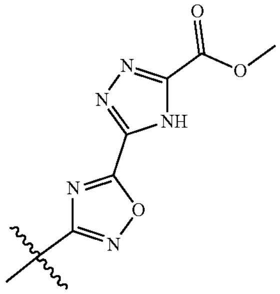
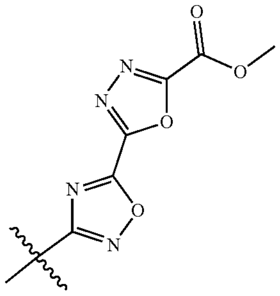
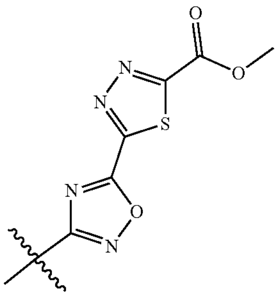
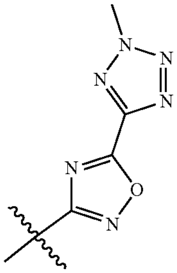
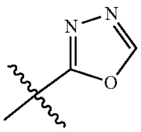
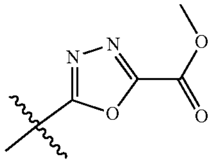
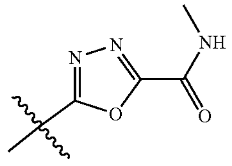
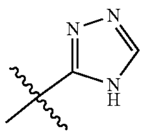
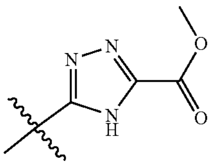
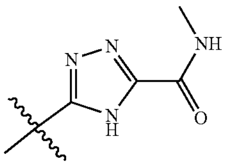
and
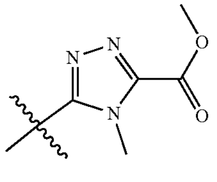

in formula (Ib),
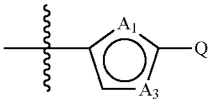
can be one selected from the following substituent:
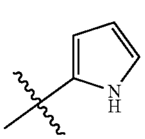
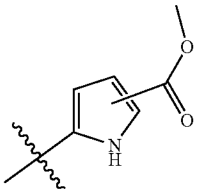
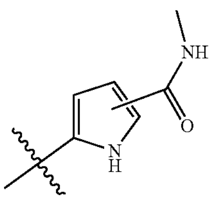
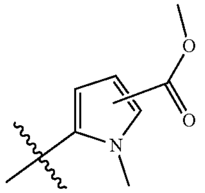
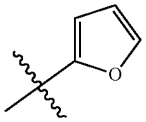
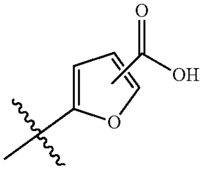
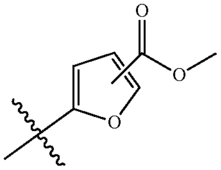
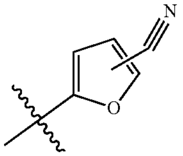
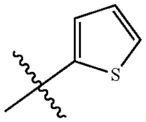
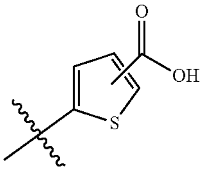
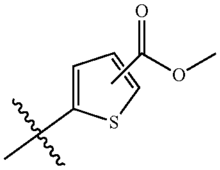
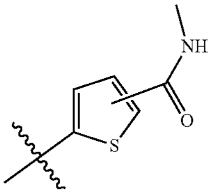
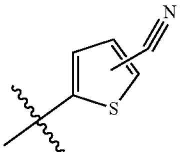
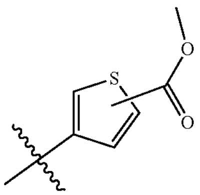
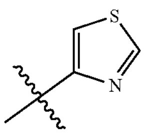
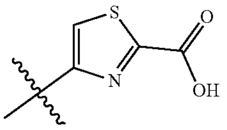
-continued
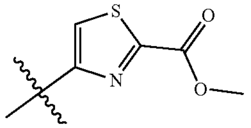
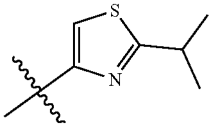
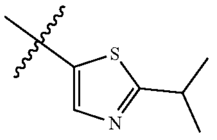
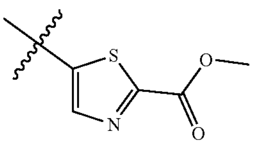
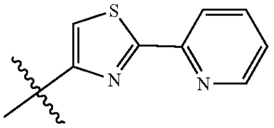
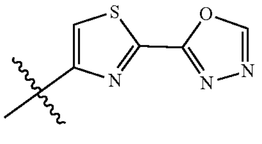
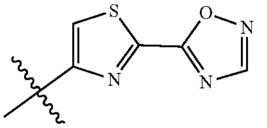 and
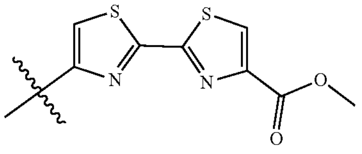
in formula (Ic) to formula (If),
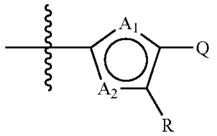
can be one selected from the following substituent:
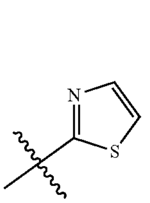
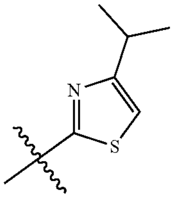
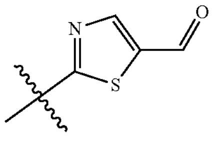
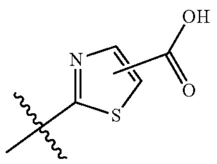
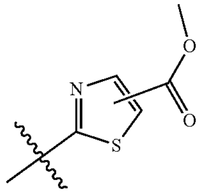
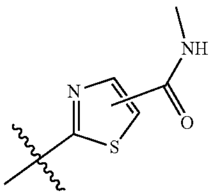

-continued
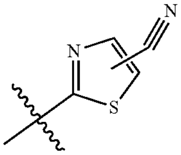
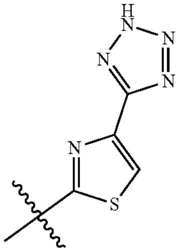
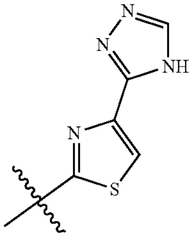
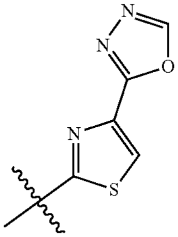
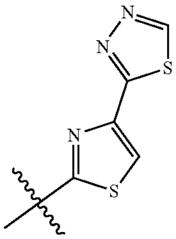
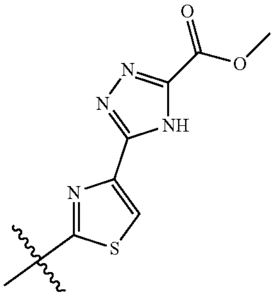
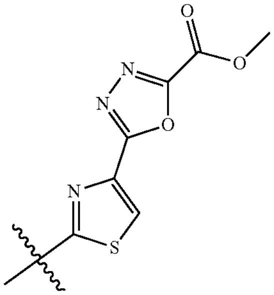
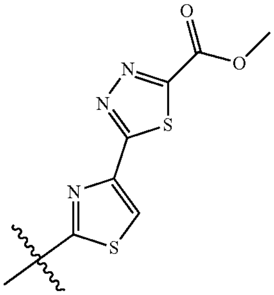
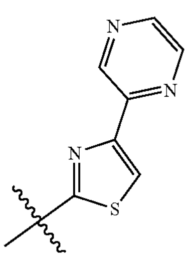
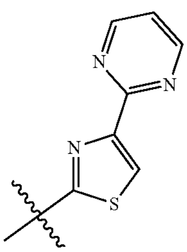
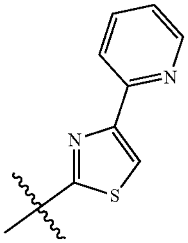
-continued
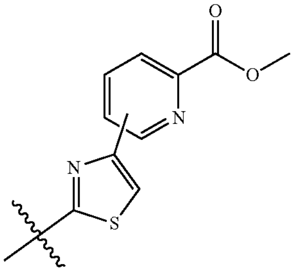
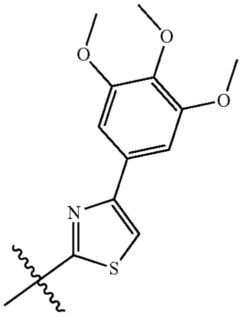
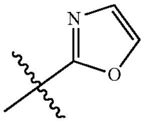
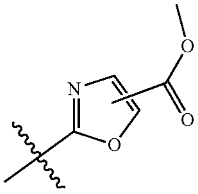
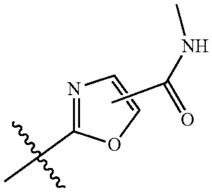
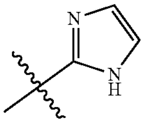
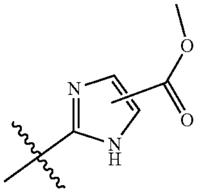
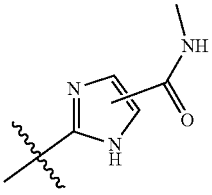
and
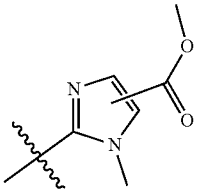
Compound of formula (Ia) can be selected from
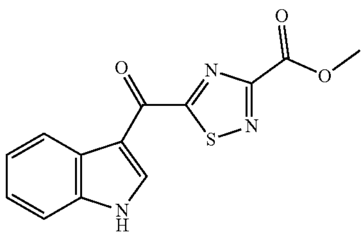

-continued
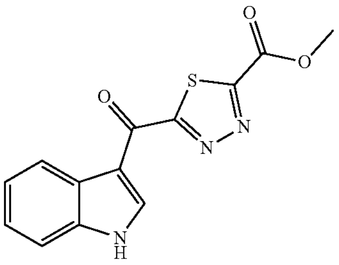
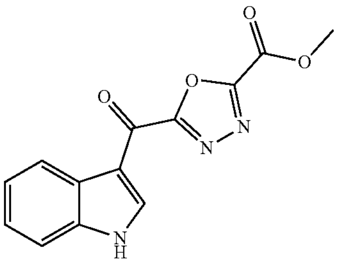
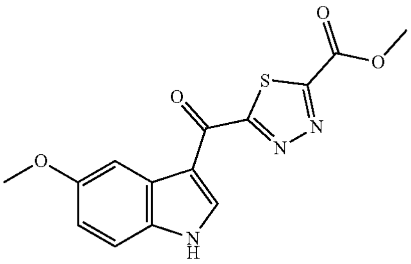
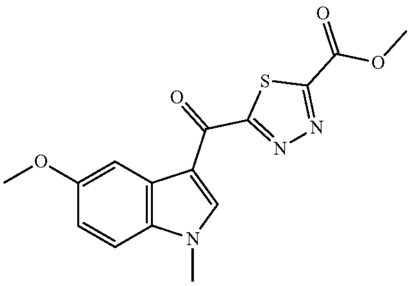
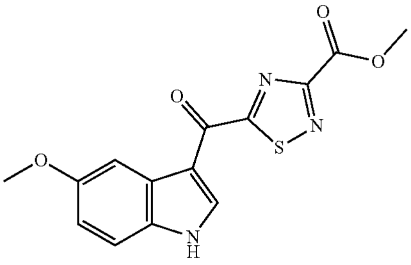
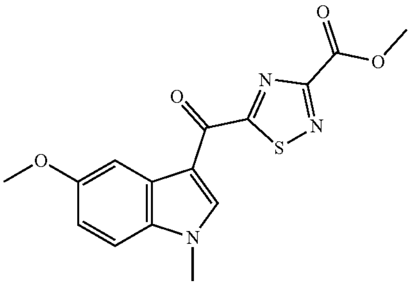
-continued
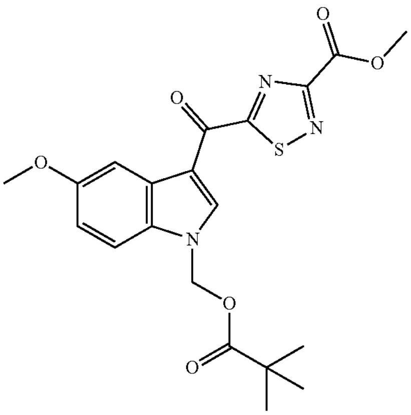
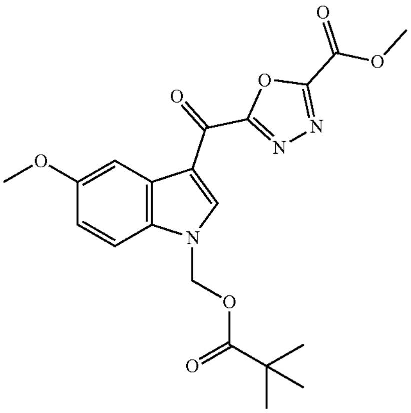
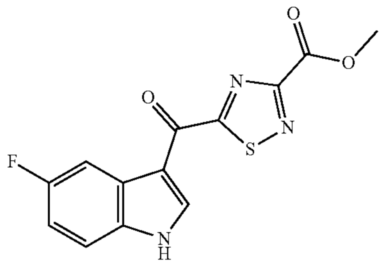
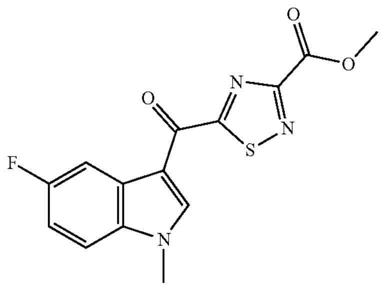
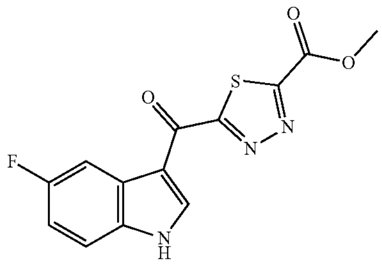

-continued
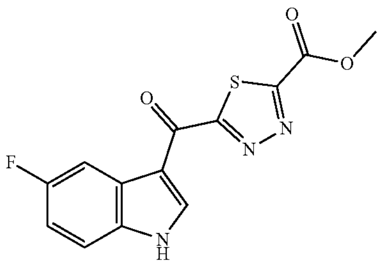
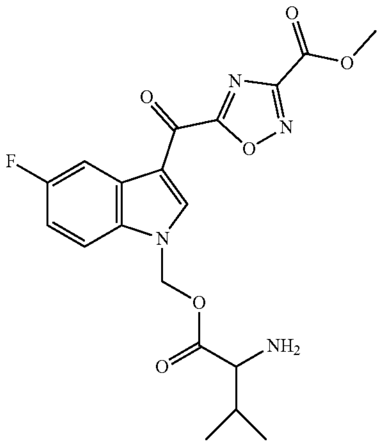
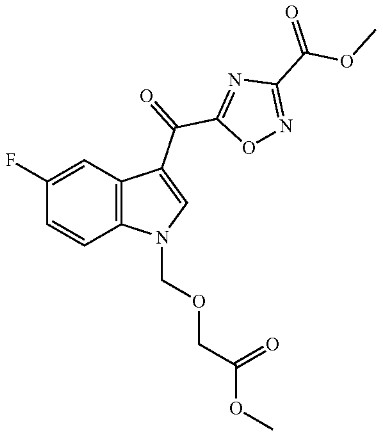
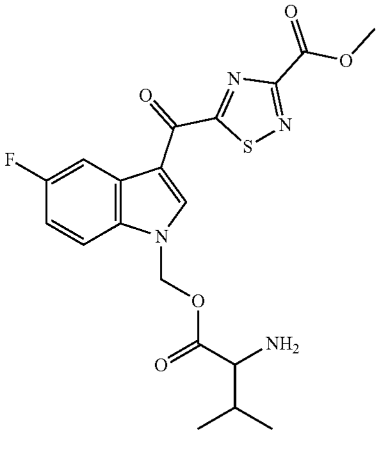
or
-continued
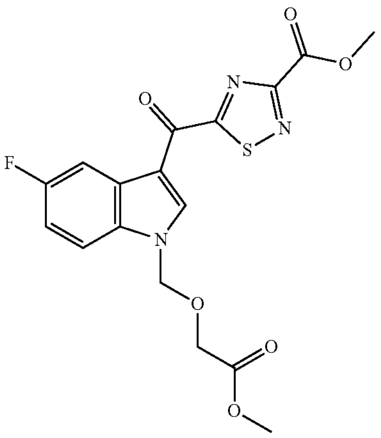
Compound of formula (Ib) can be selected from
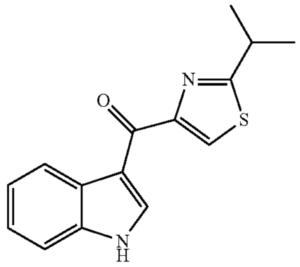
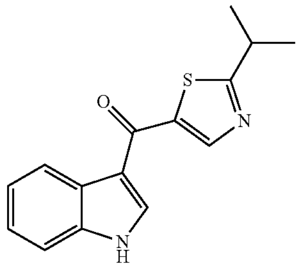
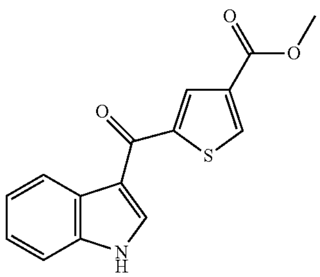
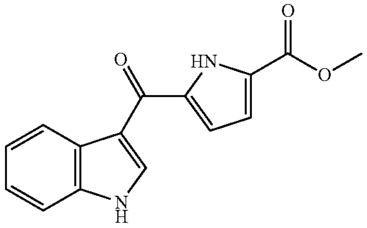
or -continued
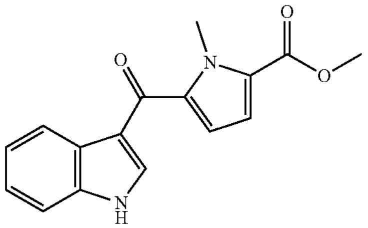
Compound of formula (Ic) can be selected from
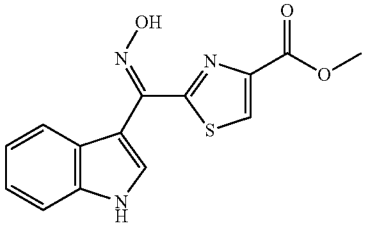
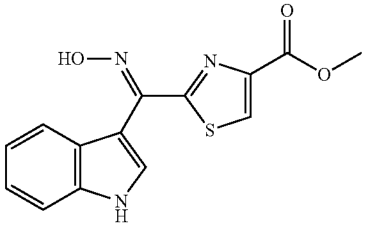
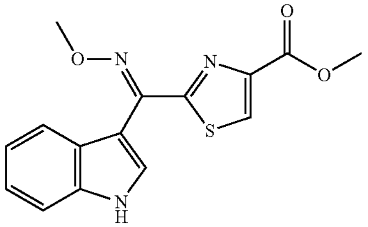
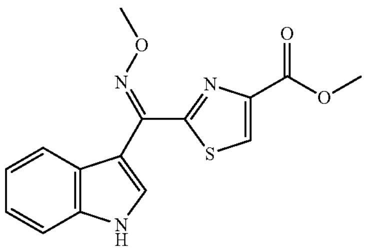
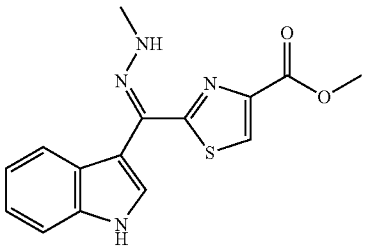
-continued
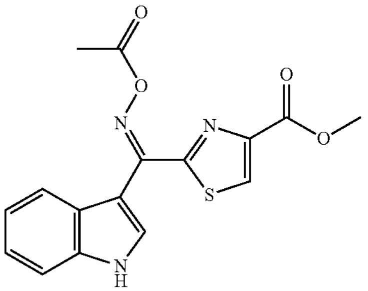
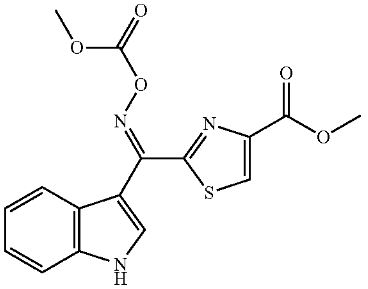
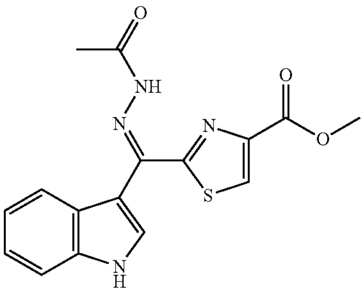
or
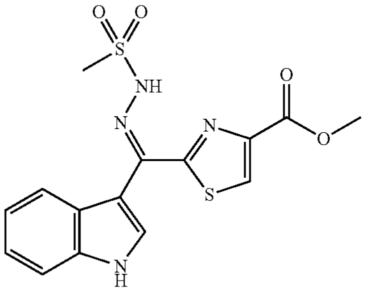
Compound of formula (Id) can be selected from
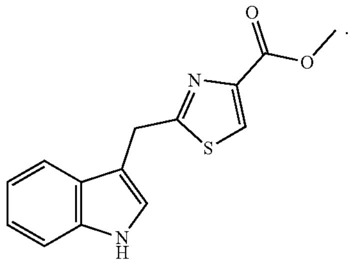 [SMILES: COC(=O)c1csc(Cc2c[nH]c3ccccc23)n1]

Compound of formula (Ie) can be selected from
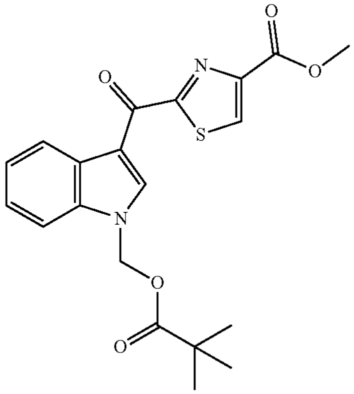
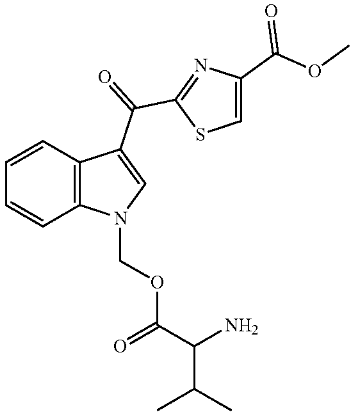
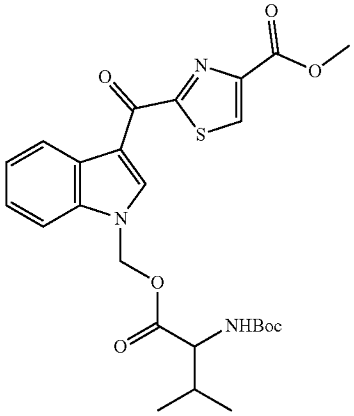
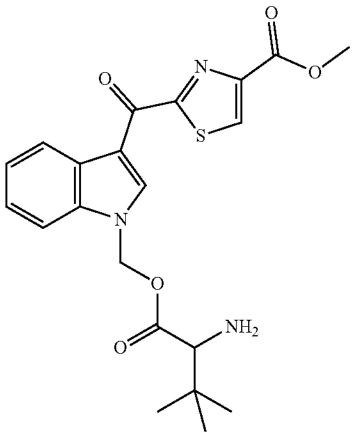
-continued
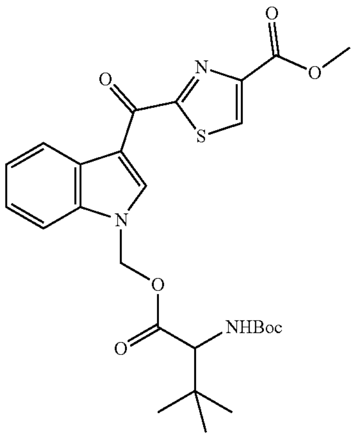
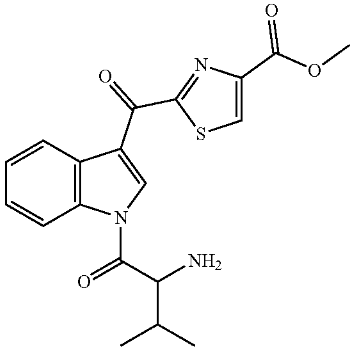
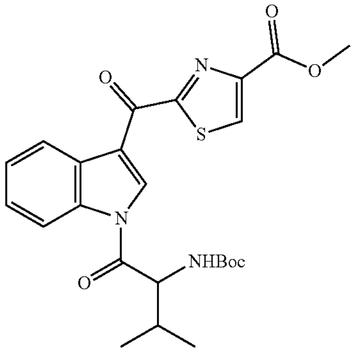
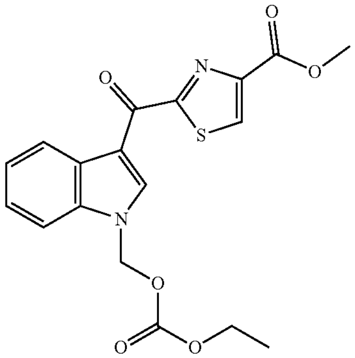

-continued
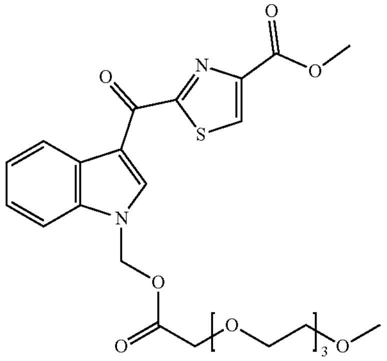
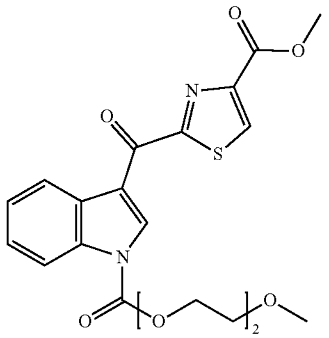
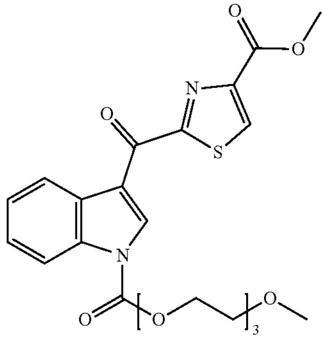
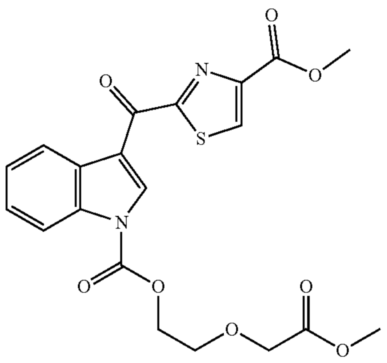
-continued
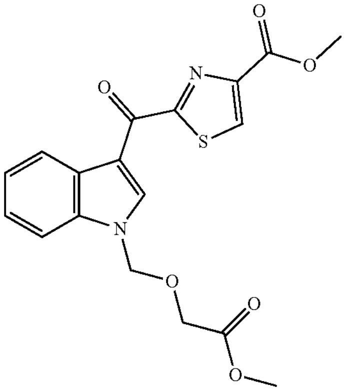
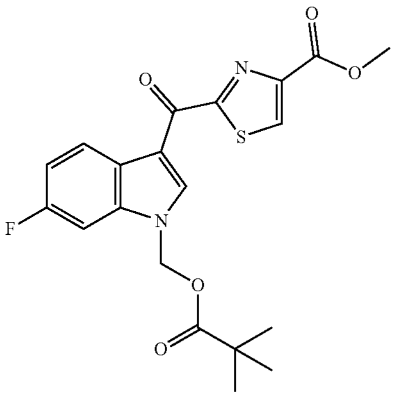
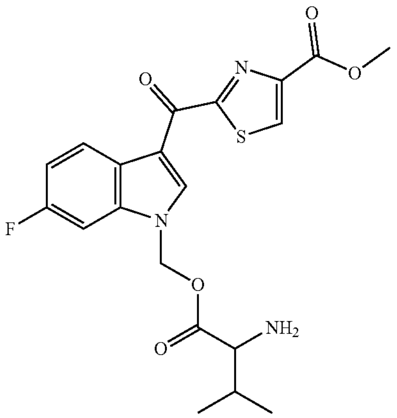
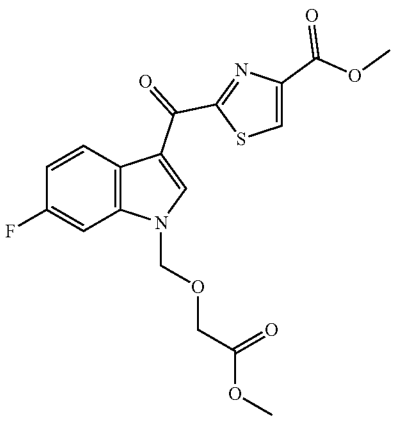

-continued
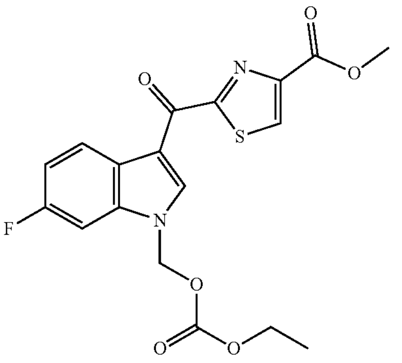
or
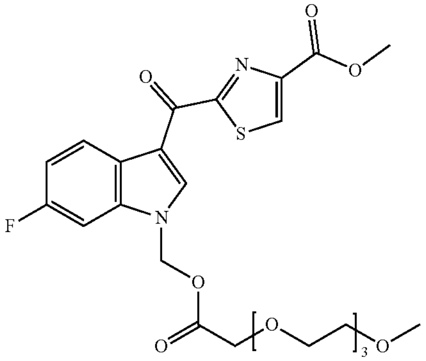
Compound of formula (Ig) can be selected from
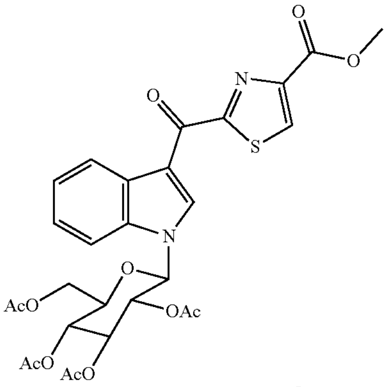
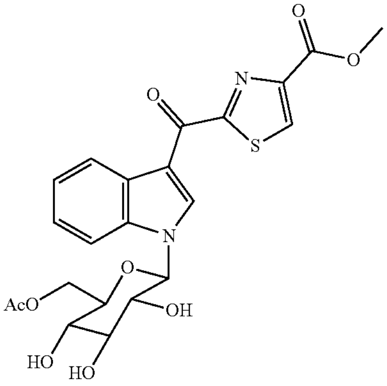
-continued
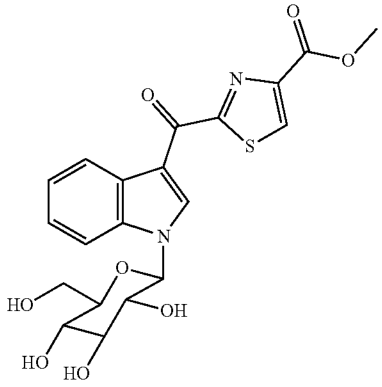
or
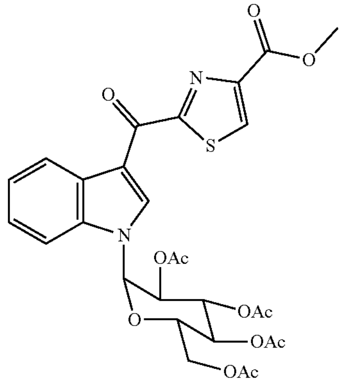
Compound of formula (Ig) can be selected from
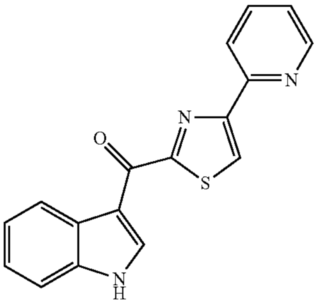
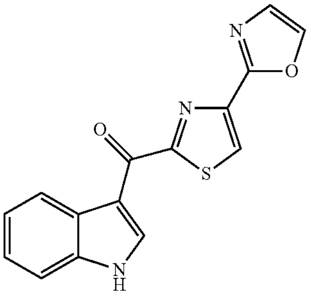

-continued
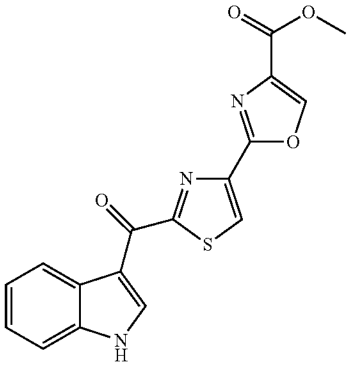
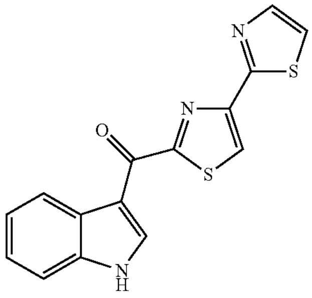
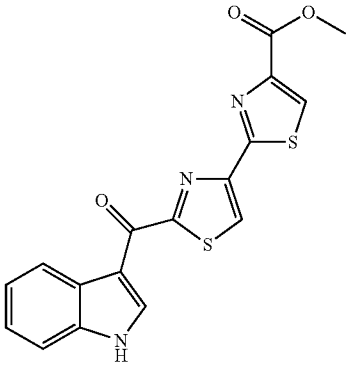
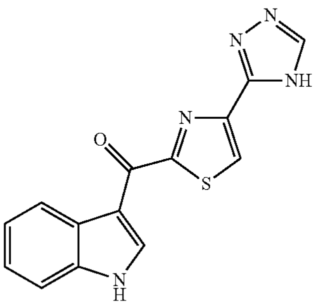
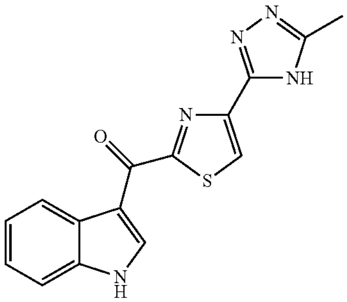
-continued
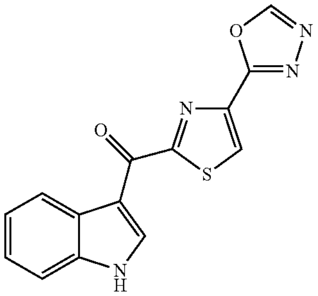
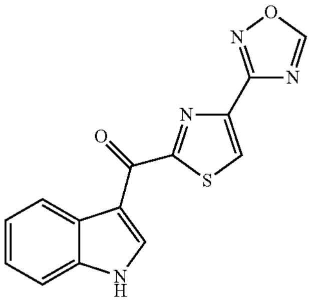
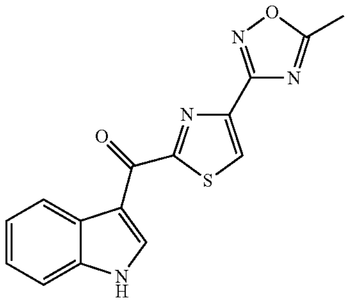
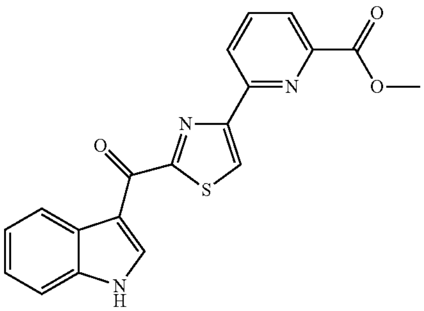
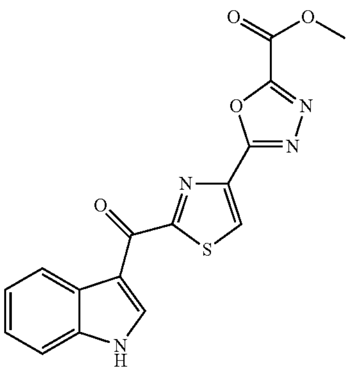

-continued
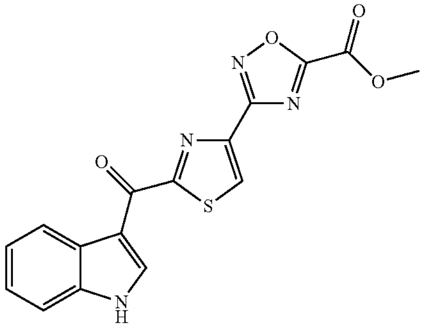
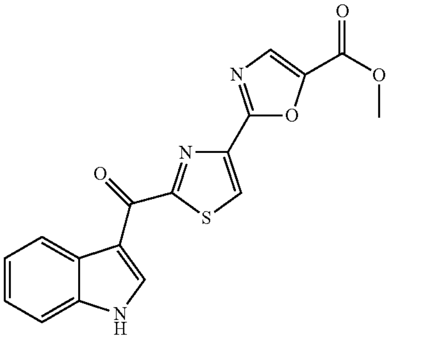
or
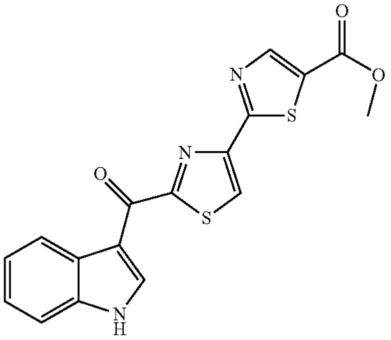
Compound of formula (Ih) can be selected from
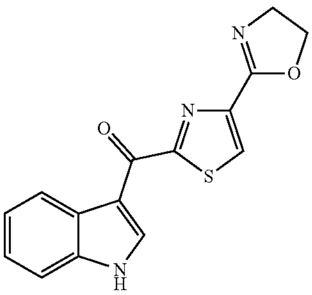
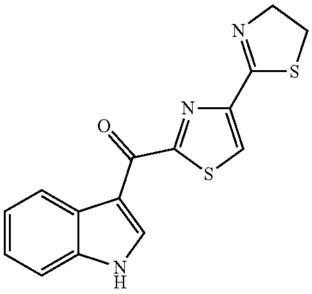
-continued
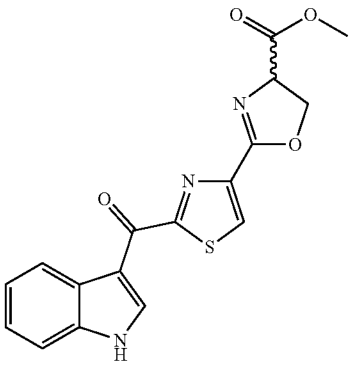
or
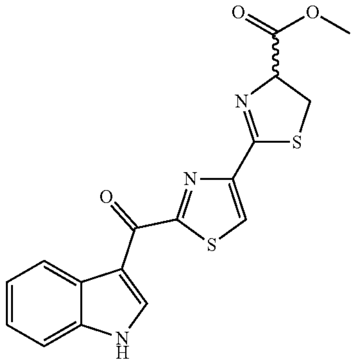
Compound of formula (I2) can be selected from
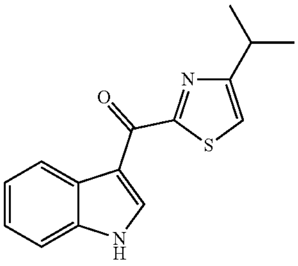
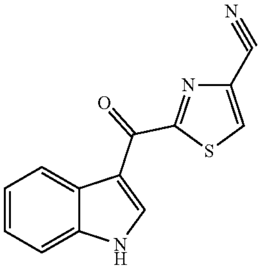
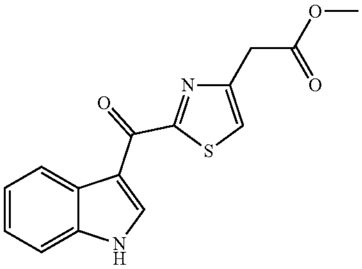

-continued
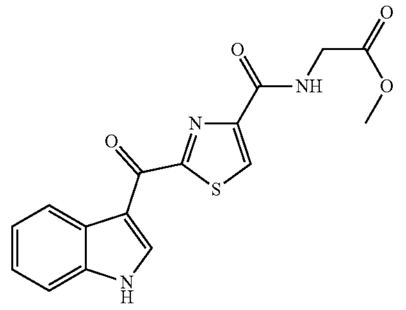
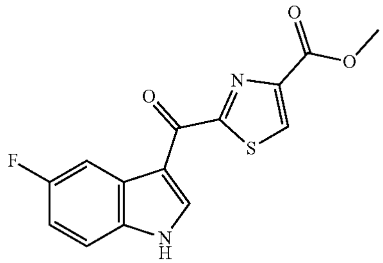
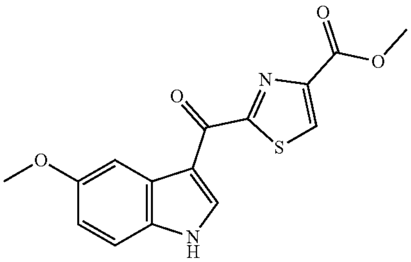
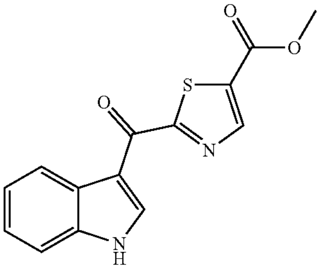
or
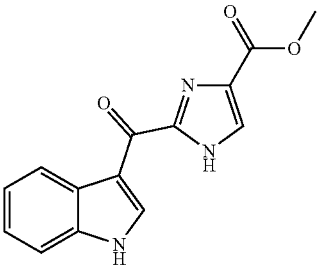
Compound of formula (I2) can be selected from
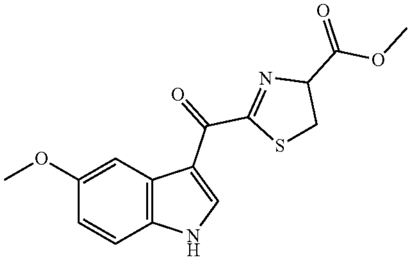
or
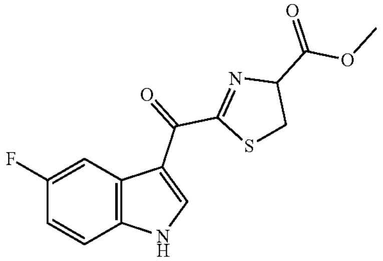
.
Compound of formula (I3) can be selected from
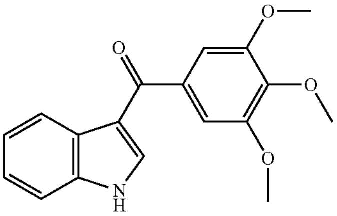
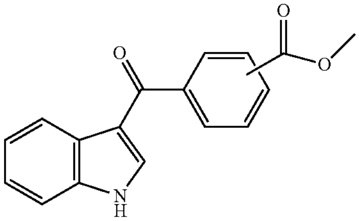
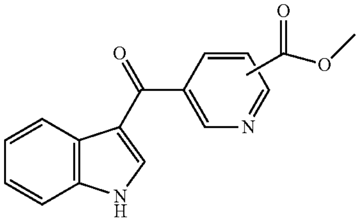
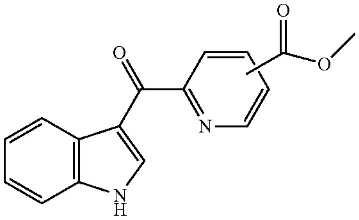
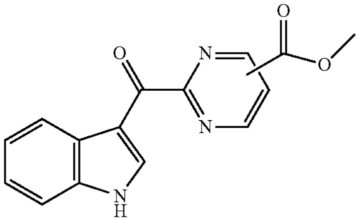

-continued
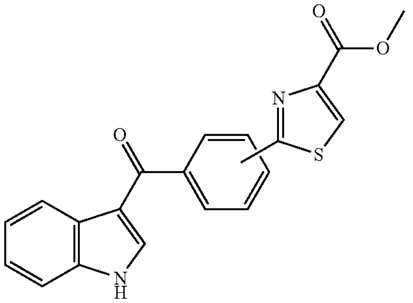
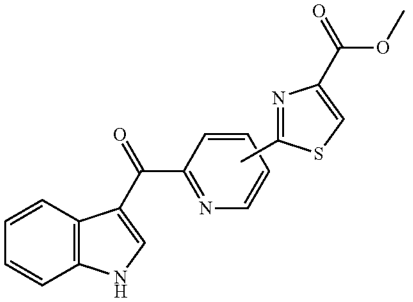
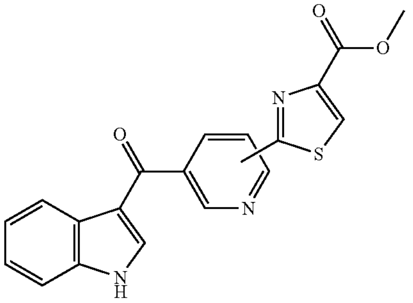
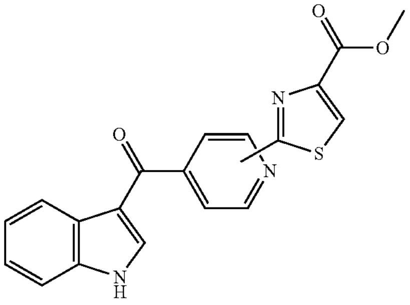
or
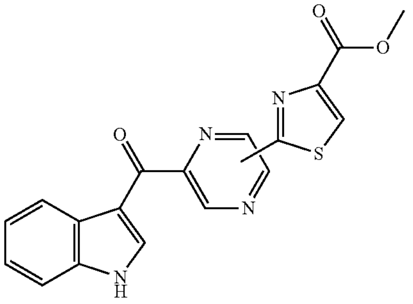
Aryl hydrocarbon receptor modulators shown in formula (I) of the invention can be classified into 5 categories of compound as follows:
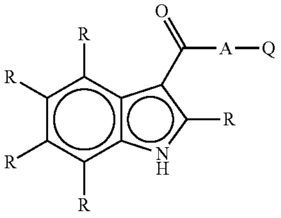
formula ($I_A$)(when R' is H)
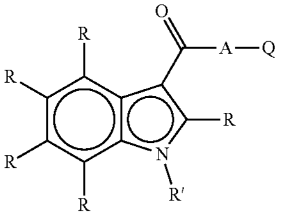
formula ($I_B$)(when R' isn't H)
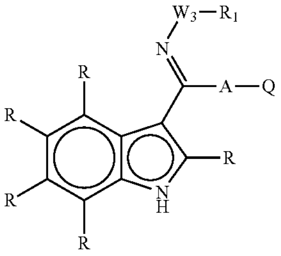
formula ($I_C$)(when R' is H),
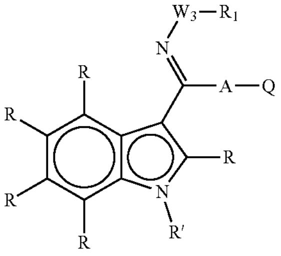
formula ($I_D$)(when R' isn't H),
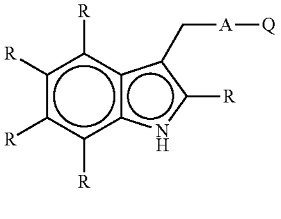

formula ($I_E$) (when R' is H)

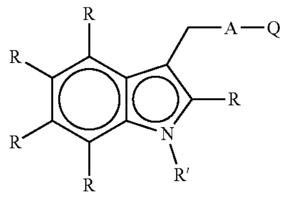

formula ($I_F$)(when R' isn't H)

Wherein, synthesis route of formula ($I_A$) to formula ($I_F$) is as follows

Step 1, starting material S (indole or indole derivative) reacts with acyl halides compound (ClC(O)AQ), alcoholic compound, or olefinic compound by the Friedel-Craft to give target compound $I_A$ of 3-substituted indole;

Step 2, target compound $I_A$ reacts with R'X or R'OH to give target compound $I_B$;

Step 3, target compound $I_A$ or target compound $I_B$ reacts with $H_2NW_3R_1$ to give target compound $I_C$ or target compound $I_D$;

Step 4, target compound $I_A$ or target compound $I_B$ are reduced to give target compound $I_E$ or target compound $I_F$ by reduction reaction.

Positive effect of the present disclosure is that compounds shown in formula (I) of the present disclosure can coupled to AhR to regulate those functions and signal paths con-

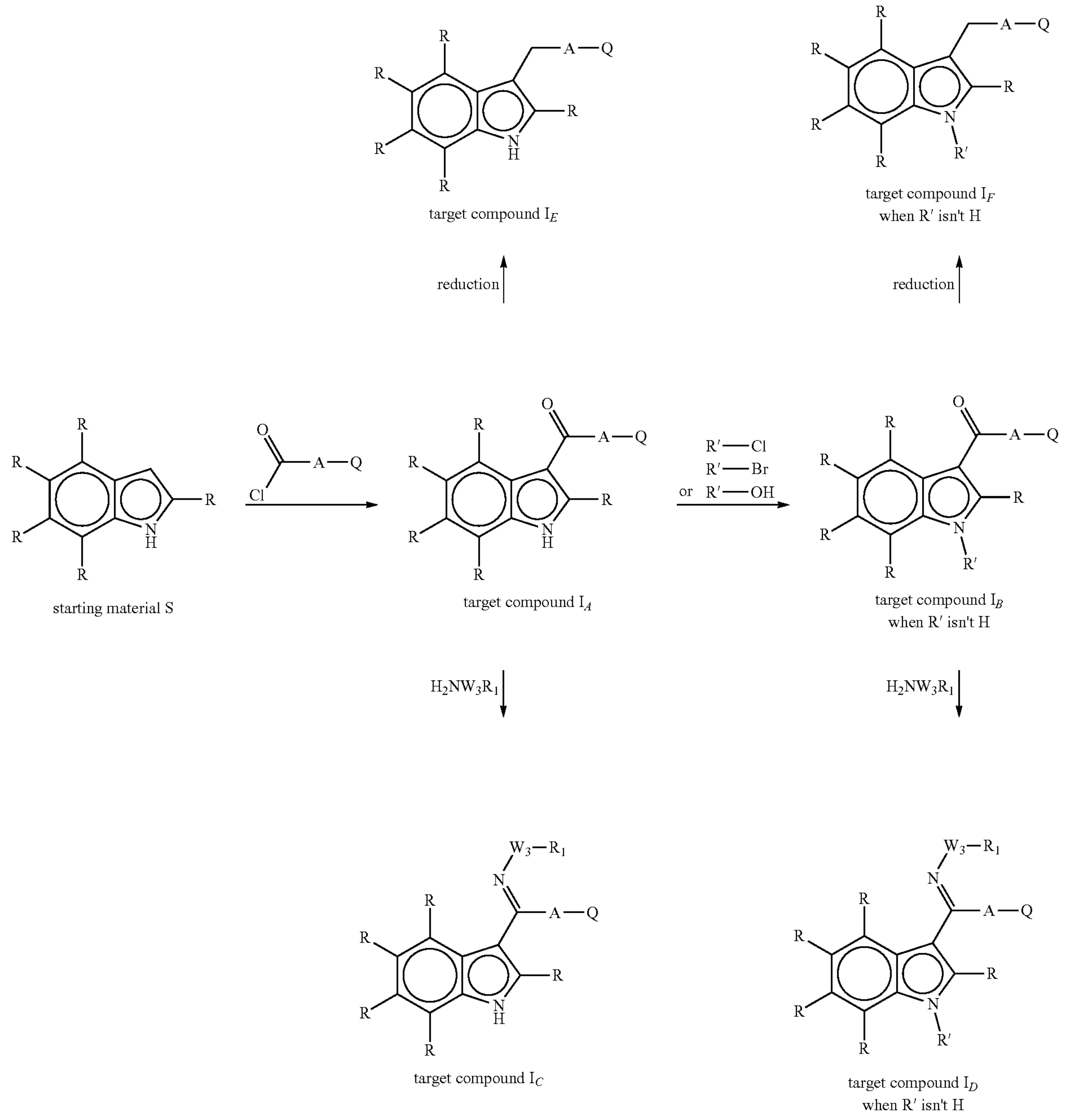

trolled by AhR, thereby to affect growth and proliferation of cancer cells and invasiveness of tumor cells. Pharmaceutical composition containing compound shown in Formula (I) can be used as AhR inhibitor or non-constitutive AhR agonists (non-constitutive AhR agonists) to inhibit cancer cell growth and to inhibit metastasis and invasion of tumor cells.

DETAIL DESCRIPTION OF PREFERRED EMBODIMENTS

Example 1 Compound 1-1 and Compound 1-2

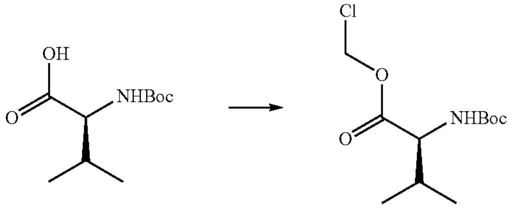

Intermediate 1a

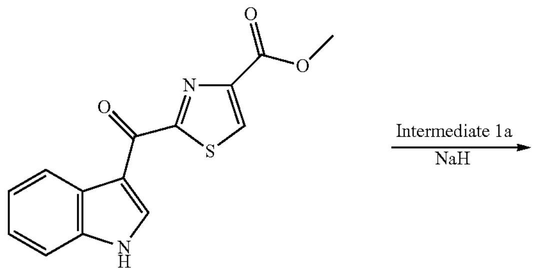

Raw material S1

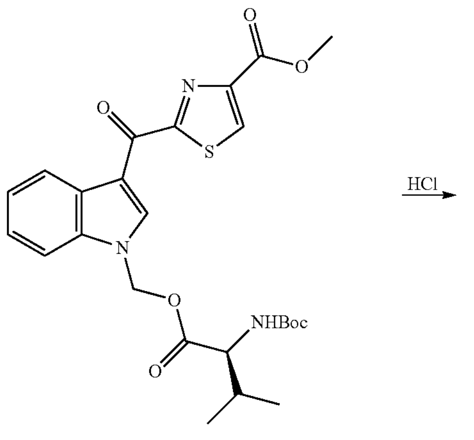

Compound 1-1

-continued

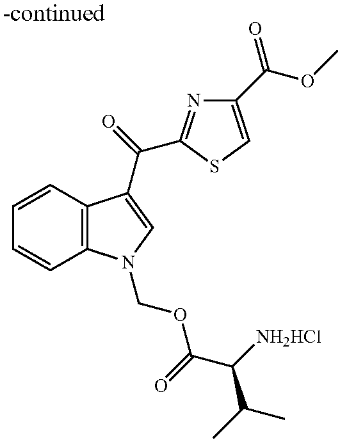

Compound 1-2

Synthesis of Intermediate 1a

Sodium bicarbonate (1.546 g, 16.411 mmol) and tetrabutylammonium bromide (0.237 g, 0.736 mmol) were added into a suspension of Boc-L-Valine (0.8 g, 3.66 mmol) in dichloromethane and water (12 mL/12 mL) under stirring. Then reaction mixture was cooled to below 0° C., into which chloromethyl chlorosulfonate (0.91 g, 5.52 mmol) was slowly added dropwise, and then stirred overnight. Reaction solution was extracted with dichloromethane twice. Organic phase was washed by water and saturated aqueous sodium chloride solution once respectively, then dried over anhydrous sodium sulfate and concentrated under reduced pressure to give a crude product. The crude product was purified by silica gel column chromatography (PE/EA=20/1) to give an oily Intermediate 1a (0.97 g, yield 99%).

Synthesis of Compound 1-1

Sodium hydride (0.165 g, 4.139 mmol) was added in batches into a solution of Raw material S1 (1 g, 3.763 mmol) in dimethyl formamide (DMF) (10 mL) under stirring. Then reaction system was heated up to 40° C. to react for 1 hour and cooled to room temperature, into which a solution of Intermediate 1a (0.97 g, 3.6 mmol) in DMF (2 mL) was slowly added dropwise, lastly stirred at room temperature overnight. Reaction solution was poured into 60 mL of ice water and filtered to give a crude product. The crude product was purified by silica gel column chromatography (PE/EA=20/1 to 10/1) to give Compound 1-1 (0.5 g, yield 28%). MS (ESI) m/z: 516 $[M+1]^+$.

Synthesis of Compound 1-2

Compound 1-1 (0.5 g, 0.97 mmol) was dissolved in dioxane (2 mL), into which a solution of hydrogen chloride in dioxane (5 mL) was added dropwise. Reaction system was kept at room temperature overnight. Then the reaction solution was filtered to give Compound 1-2 (0.24 g, yield 55%).

$^1H$ NMR (400 MHz, $CDCl_3$): δ 9.24 (s, 1H), 8.94 (s, 1H), 8.41 (brs, 3H), 8.35 (d, J=7.6 Hz, 1H), 7.81 (d, J=7.6 Hz, 1H), 7.39~7.47 (m, 2H), 6.63 (d, J=10.8 Hz, 1H), 6.58 (d, J=10.8 Hz, 1H), 4.02 (d, J=7.6 Hz, 1H), 3.94 (s, 3H), 2.07~2.12 (m, 1H), 0.84 (d, J=7.2 Hz, 1H), 0.80 (d, J=7.2 Hz, 1H). MS(ESI) m/z: 416 [M+1]+

Example 2 Compound 2-1 and Compound 2-2

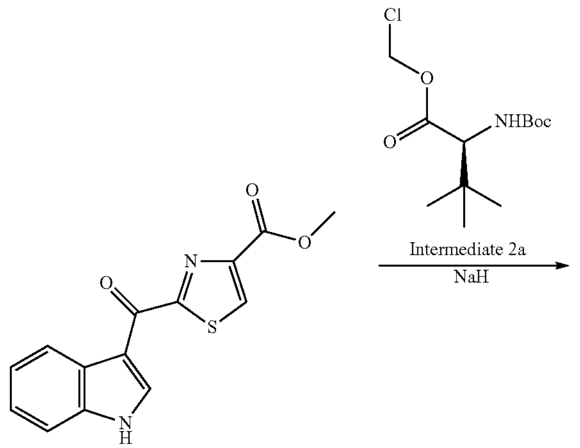

Raw material S1

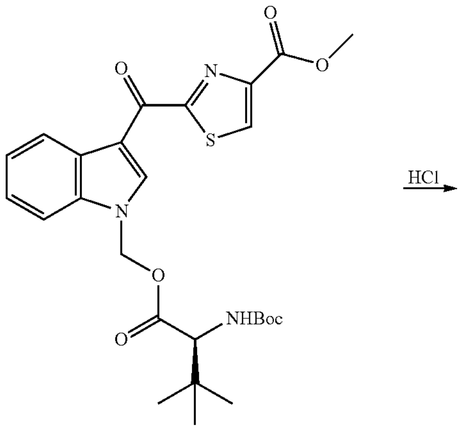

Compound 2-1

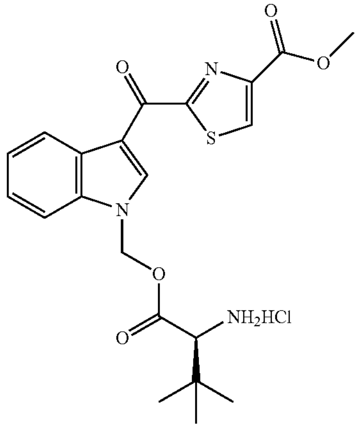

Compound 2-2

Synthesis of Intermediate 2a

Synthesis method of Intermediate 2a was the same as that of Intermediate 1a, an oily Intermediate 2a (2.3 g, Yield 95%) was synthesized from Boc-L-Tert-leucine (2 g, 8.647 mmol).

Synthesis of Compound 2-1

Synthesis method of Compound 2-1 was the same as that of Compound 1-1. Compound 2-1 (1.4 g, yield 74%) was synthesized from Intermediate 2a (1 g, 3.6 mmol).

$^1$H NMR (400 MHz, $CDCl_3$): δ 9.24 (s, 1H), 8.50~8.52 (m, 1H), 8.46 (s, 1H), 7.57~7.60 (m, 1H), 7.39~7.43 (m, 1H), 6.42 (d, J=11.2 Hz, 1H), 6.17 (d, J=11.2 Hz, 1H), 5.05 (d, J=9.2 Hz, 1H), 4.10 (d, J=8.4 Hz, 1H), 4.04 (s, 3H), 1.42 (s, 9H), 0.83 (s, 9H). MS(ESI) m/z:530 $[M+1]^+$.

Synthesis of Compound 2-2

Synthesis method of Compound 2-2 was the same as that of Compound 1-2. Compound 2-2 (0.85 g, yield 70%) was synthesized from Compound 2-1 (1.4 g, 2.6 mmol).

$^1$H NMR (400 MHz, $CDCl_3$): δ 9.24 (s, 1H), 8.94 (s, 1H), 8.36 (d, J=7.2 Hz, 1H), 8.27 (brs, 3H), 7.82 (d, J=7.6 Hz, 1H), 7.39~7.47 (m, 2H), 6.61 (s, 1H), 3.93 (s, 3H), 3.86 (s, 3H), 0.89 (s, 9H). MS(ESI) m/z: 430$[M+1]^+$.

Example 3 Compound 3

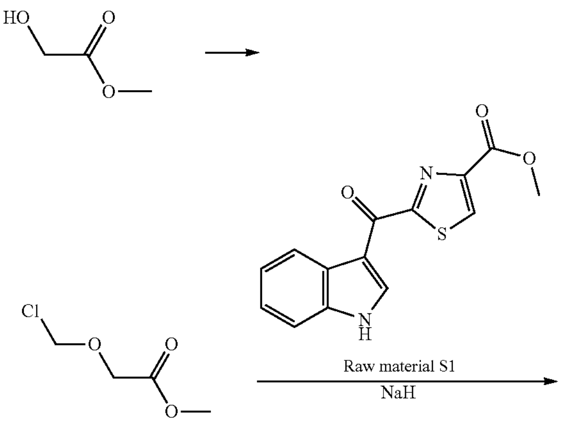

Intermediate 3a

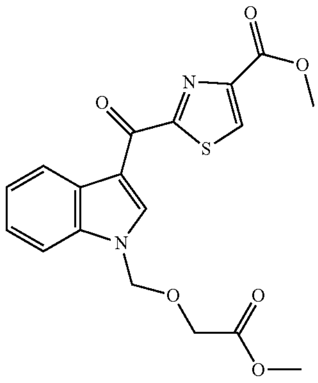

Compound 3

Synthesis of Intermediate 3a

Dichloromethane (50 mL) and paraformaldehyde (1.3 g, 43.3 mmol) were added to methyl glycolate weighed (3 g, 33.3 mmol). Reaction system was cooled to below −20° C., through which hydrogen chloride gas prepared at real time was continuously aerated, and kept to react for 30 minutes at −20° C. After that, hydrogen chloride gas was removed. Reaction solution was added with anhydrous magnesium sulfate and anhydrous sodium sulfate, further incubated for 1 hour, then kept overnight at room temperature, then filtered to remove the solid. Mother liquor was concentrated to dryness at room temperature and purified by silica gel column chromatography to give Intermediate 3a (1.2 g, yield 26%).

Synthesis of Compound 3

Synthesis method of Compound 3 was the same as that of Compound 1-1. A pale yellow solid of Compound 3 (280 mg, yield 74%) was synthesized from Raw material S1 (286 mg, immol) and Intermediates 3a (500 mg, 3.6 mmol).

$^1$H NMR (400 MHz, $CDCl_3$): δ 9.19 (s, 1H), 8.55~8.56 (m, 1H), 8.45 (s, 1H), 7.63~7.65 (m, 1H), 7.41~7.45 (m, 2H), 5.82 (s, 2H), 4.12 (s, 2H), 4.03 (s, 3H), 3.77 (s, 3H). MS (ESI) m/z: 389 $[M+I]^+$.

Example 4 Compound 4-1 and Compound 4-2

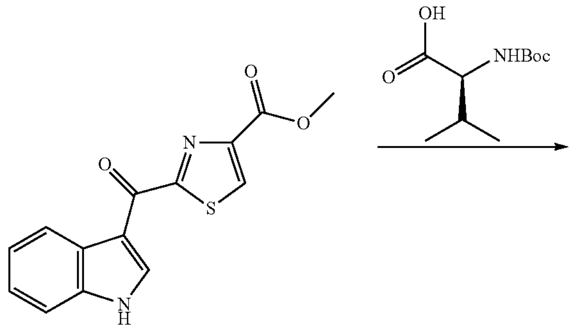

Raw material S1

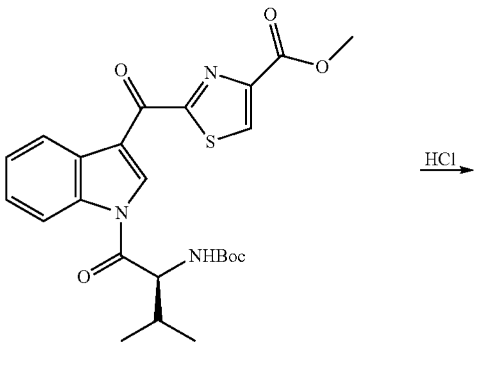

Compound 4-1

-continued

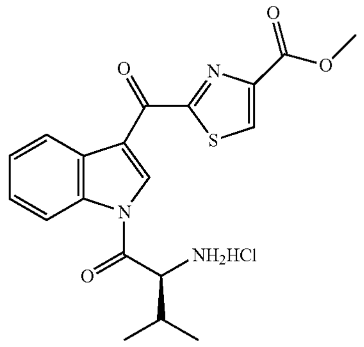

Compound 4-2

Synthesis of Compound 4-1

Raw material S1 (2.86 g, 10 mmol) was added to a solution of Boc-L-valine (2.17 g, 10 mmol) in DMF (20 mL), then into which HATU (4.56 g, 12 mmol) and DIEA (2.6 g, 20 mmol) were added under stirring. Reaction system was stirred overnight. Reaction solution was poured into water and extracted with ethyl acetate twice. Organic phase was washed with water and saturated brine each once, then dried over anhydrous sodium sulfate and concentrated under reduced pressure to give a crude product. The crude product was purified by silica gel column chromatography (PE/EA=4/1) to give Compound 4-1 (3.01 g, yield 62%).

$^1$H NMR (400 MHz, $CDCl_3$): δ 9.75 (s, 1H), 8.48~8.55 (m, 3H), 7.47~7.52 (m, 2H), 5.44 (d, J=8.8 Hz, 1H), 5.27 (dd, J=4.0, 8.8 Hz, 1H), 4.05 (s, 3H), 2.37~2.42 (m, 1H), 1.48 (s, 9H), 1.25 (d, J=6.8 Hz, 3H), 1.01 (d, J=6.4 Hz, 3H). MS (ESI) m/z: 508 $[M+23]^+$.

Synthesis of Compound 4-2

Synthesis method of Compound 4-2 was same as that of Compound 1-2. Compound 4-2 (348 mg, yield 77%) was synthesized from Compound 4-1 (486 mg, immol).

$^1$H NMR (400 MHz, $CDCl_3$): δ 9.56 (s, 1H), 9.04 (s, 1H), 8.81 (brs, 3H), 8.46~8.48 (m, 1H), 8.35~8.37 (s, 1H), 7.54~7.60 (m, 2H), 5.01 (d, J=4.8 Hz, 1H), 3.99 (s, 3H), 2.42~2.47 (m, 1H), 1.17 (d, J=6.8 Hz, 3H), 1.07 (d, J=6.8 Hz, 3H). MS (ESI) m/z: 386 [M+1].

Example 5 Compound 5

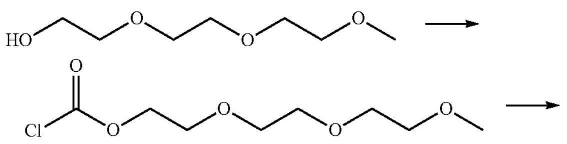

Intermediate 5a

-continued

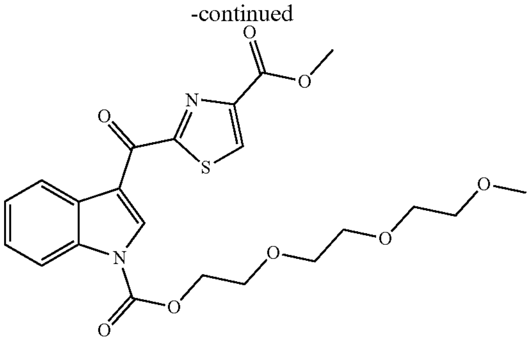

Compound 5

Synthesis of Intermediate 5a

Triethylene glycol monomethyl ether (2.0 g, 12.2 mmol) was dissolved in tetrahydrofuran (20 mL), into which triphosgene (1.8 g, 6.1 mmol) was added under stirring. Reaction system was cooled to 0° C. by ice bath, into which pyridine (1.5 g, 19.0 mmol) was slowly added dropwise, kept to react at room temperature for 1 hour and then filtered. Mother liquor was concentrated under reduced pressure to give a colourless liquid of Intermediate 5a (2.1 g, yield 75.9%).

Synthesis of Compound 5

Raw material S-1 (2.0 g, 7.0 mmol) was dissolved in tetrahydrofuran (80 mL), then into which triethylamine (1.5 g, 14.9 mmol) was added dropwise. Reaction system was cooled to 0° C. by ice bath, then into which a solution of Intermediate 5-1 (2.1 g, 9.3 mmol) in dichloromethane (20 mL) was added dropwise. Reaction system was kept for 1 hour at room temperature, then poured into ice water and extracted with dichloromethane. Organic phase was washed with saturated brine and dried over anhydrous sodium sulfate, and then concentrated to dryness under reduced pressure. Crude product was purified by silica gel column chromatography (PE/EA=3/1) to give a white solid of Compound 5 (2.5 g, yield 75.8%).

$^1$H NMR (400 MHz, $CDCl_3$): δ 9.56 (s, 1H), 8.49 (s, 2H), 8.33~8.24 (m, 1H), 7.51~7.39 (m, 2H), 4.75~4.67 (m, 2H), 4.03 (s, 3H), 4.01~3.94 (m, 2H), 3.80 (dd, J=5.9, 3.4 Hz, 2H), 3.74~3.69 (m, 2H), 3.67~3.62 (m, 2H), 3.53~3.48 (m, 2H), 3.35 (s, 3H). LCMS(ESI) m/z:477.2[M+1]$^+$.

Example 6 Compound 6

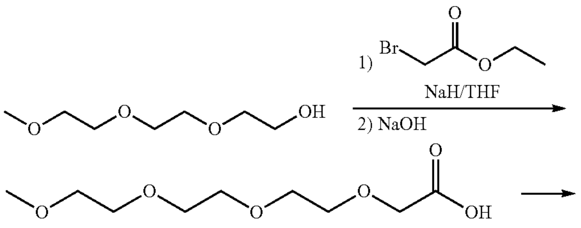

Intermediate 6a

-continued

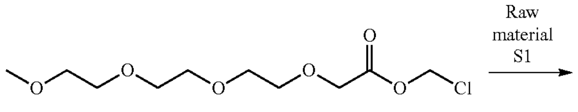

Intermediate 6b

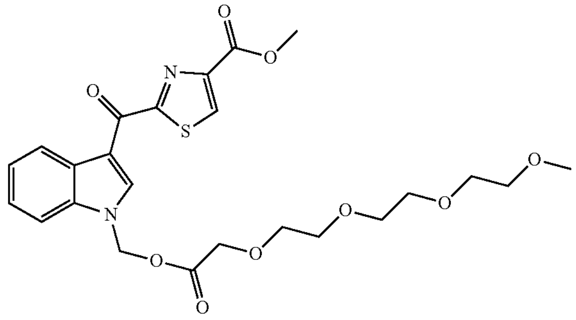

Compound 6

Synthesis of Intermediate 6a

Triethylene glycol monomethyl ether (10 g, 60.9 mmol) was dissolved in tetrahydrofuran (100 mL), into which sodium hydride (3.2 g, 60% content, 79.17 mmol) was added in batches at 0° C. After addition, reaction system was stirred at room temperature for 1 hour, then into which ethyl bromoacetate (20.1 g, 122 mmol) was added dropwise, and kept to react at room temperature for 3 hours. Reaction solution was added directly with water (100 mL) and then extracted with dichloromethane. Organic phase was dried over anhydrous sodium sulphate, concentrated to dryness under reduced pressure, then into which water (100 mL) and sodium hydroxide of solid (3 g, 73 mmol) were added, stirred at room temperature for 1 hour and extracted with ethyl acetate twice. Aqueous phase was adjusted with dilute hydrochloric acid to pH=2 to 3 and then extracted with mixed solvent of dichloromethane/isopropanol (V/V=10:1) for 5 times. Organic phase was dried over anhydrous sodium sulfate and concentrated under reduced pressure to give a crude product. Crude product was purified by silica gel column chromatography (DCM:$CH_3OH$=100:1-20:1) to give Compound 6a (10 g, yield 74%).

Synthesis of Intermediate 6b

Compound 6a (2 g, 8.99 mmol) was dissolved in dichloromethane (20 mL), then into which sodium bicarbonate (3.1 g, 36 mmol), tetrabutylammonium bromide (289 mg, 0.699 mmol) and water (20 mL) were added. Reaction system was cooled to 0° C., hereinafter, into which a solution of chloromethyl chlorosulfonate (1.48 g, 8.99 mmol) in dichloromethane (10 mL) solution was added dropwise, and was stirred overnight at room temperature, then kept statically for stratification. Aqueous phase was extracted with dichloromethane twice. Organic phase was dried over anhydrous sodium sulfate and concentrated under reduced pressure to give a crude product. The crude product was purified by silica gel column chromatography (DCM: $CH_3OH$=50:1) to give an oily liquid of Intermediate 6b (300 mg, yield 12.3%). LCMS (ESI) m/z: 271 [M+1]$^+$.

Synthesis of Compound 6

Raw material S1 (1 g, 3.49 mmol) was dissolved in DMF (15 mL), into which sodium hydride (153 mg, content of 60%, 3.84 mmol) was added at 0° C. After addition, reaction system was stirred for 10 minutes, then heated to 50° C., stirred for 1 hour and then cooled to room temperature, into which Compound 6b (0.944 mg, 3.49 mmol) was added, then kept to react for 4 h at room temperature, then into which water and dichloromethane were added and extracted with dichloromethane for 3 times. Organic phase was dried over anhydrous sulphate sodium and concentrated under reduced pressure to obtain a crude product. The crude product was purified by silica gel column chromatography ($CH_3OH$:DCM=0-2%) to give Compound 6 (650 mg, yield 35.8%).

$^1$H NMR (400 MHz, $CDCl_3$): δ 9.25 (s, 1H), 8.52~8.54 (m, 1H), 8.46 (s, 1H), 7.59~7.61 (m, 1H), 7.41~7.44 (m, 2H), 6.32 (s, 2H), 4.21 (s, 2H), 4.04 (s, 3H), 3.70~3.72 (m, 2H), 3.65~3.68 (m, 2H), 3.60~3.64 (m, 6H), 3.52~3.54 (m, 2H), 3.37 (s, 3H). LCMS (ESI) m/z: 521 [M+1]$^+$.

Example 7 Compound 7

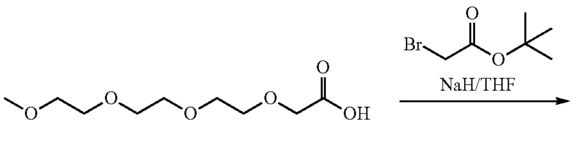

Intermediate 6a

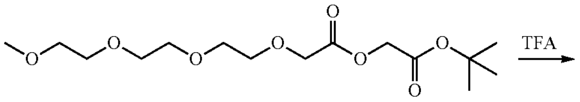

Intermediate 7a

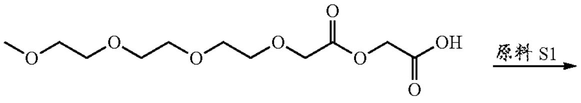

Intermediate 7b

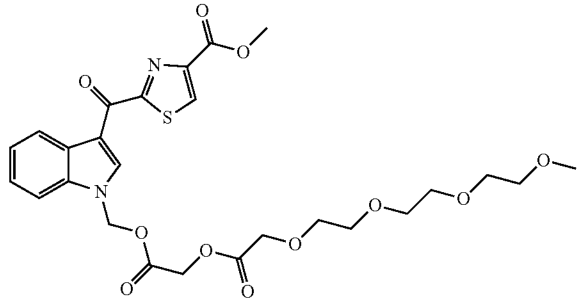

Compound 7

Synthesis of Intermediate 7a

Synthesis method of Intermediate 7a was the same as that of Compound 6a. Starting material was Intermediate 6a. Yield was 75%. LCMS (ESI) m Iz: 337.2 [M+1]$^+$.

Synthesis of Intermediate 7b

Intermediate 7a (3.4 g, 10 mmol) was dissolved in dichloromethane (5 mL), then into which trifluoroacetic acid (5 mL) was added. Reaction system was stirred at room temperature overnight and concentrated to dryness under reduced pressure. Crude product was purified by silica gel column chromatography ($CH_3OH$:DCM=0-2%) to give an oil of Intermediate 7b (2.6 g, yield 76%). LCMS (ESI) m/z: 281.2 [M+1]$^+$.

Compound 7

Synthesis method of Compound 7 was the same as that of compound 6. Yield was 55%.

$^1$H NMR (400 MHz, $CDCl_3$): δ 9.20 (s, 1H), 8.50~8.52 (m, 1H), 8.44 (s, 1H), 7.53~7.56 (m, 1H), 7.40~7.42 (m, 2H), 6.31 (s, 2H), 4.70 (s, 2), 4.25 (s, 2H), 4.02 (s, 3H), 3.63~3.71 (m, 10H), 3.53~3.55 (m, 2H), 3.37 (s, 3H). LCMS (ESI) m/z: 579.2 [M+1]+

Example 8 Compound 8

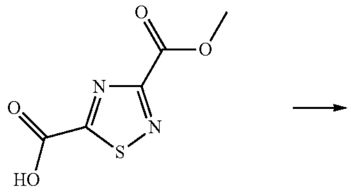

Raw material S2

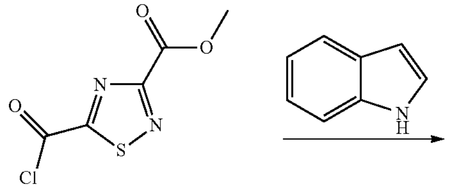

Intermediate 8a

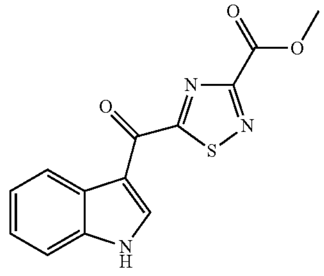

Compound 8

Synthesis of Intermediate 8a

Raw material S2 (188 mg, immol) was dissolved in dichloromethane (20 mL), into which one drop of DMF was added. Reaction system was then cooled to 0 to 5° C., then into which oxalyl chloride (151 mg, 1.2 mmol) was added dropwise. Then ice bath was removed. Reaction system was stirred at room temperature for 1 hour, then concentrated to dryness under reduced pressure, into which dichloromethane (20 mL) was used for dissolution, concentrated to dryness under reduced pressure to give Intermediate 8a which was used directly for the next step.

Synthesis of Compound 8

A solution of Intermediate 8a (immol) in dichloromethane (30 mL) was added dropwise to a suspension of anhydrous aluminium trichloride (164 mg, 1.2 mmol) in dichloromethane (30 mL). Reaction system was stirred for 2 hours, into which a solution of indole (143 mg, 1.2 mmol) in dichloromethane (30 mL) was slowly added dropwise and then reacted overnight. After that, reaction system was washed with saturated sodium bicarbonate solution. Organic phase was washed with saturated brine, then dried over anhydrous sodium sulfate and concentrated under reduced pressure to give a crude product. The crude product was purified by silica gel column chromatography (PE/EA=4/1) to obtain a pale yellow solid of Compound 8 (120 mg, yield 42%).

$^1$H NMR (400 MHz, DMSO-$d_6$): δ 12.4 (brs, 1H), 9.05 (s, 1H), 8.28~8.30 (m, 1H), 7.62~7.64 (m, 1H), 7.32~7.37 (m, 2H), 4.00 (s, 3H). MS (ESI) m/z: 288.0 [M+1]$^+$.

Example 9 to 18 Compound 9 to 18

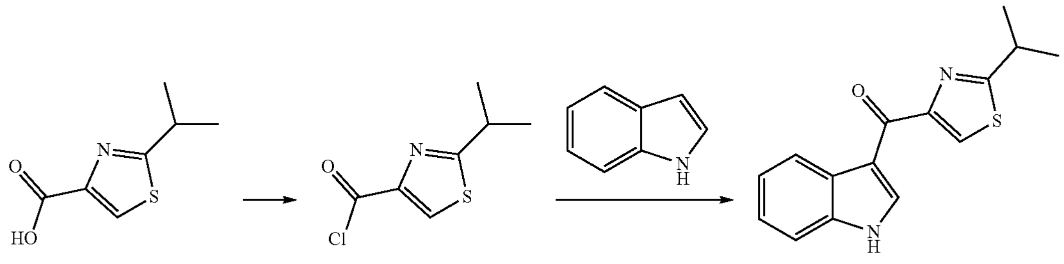

Compound 9

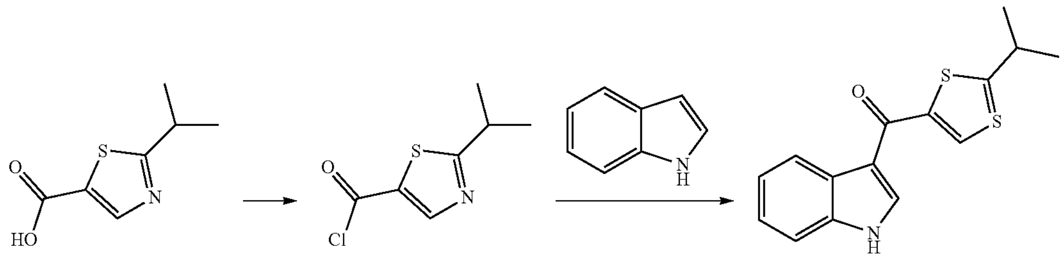

Compound 10

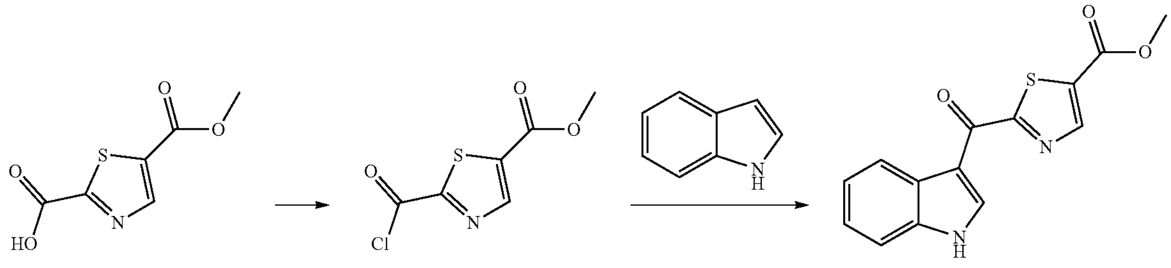

Compound 11

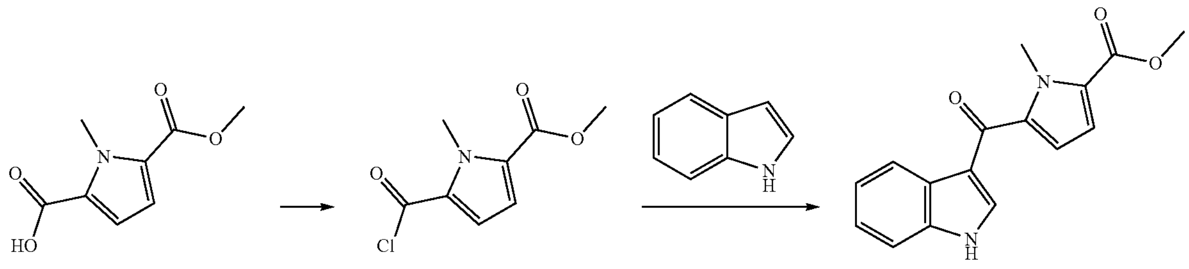

Compound 12

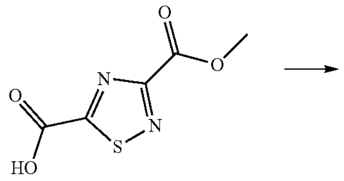

-continued
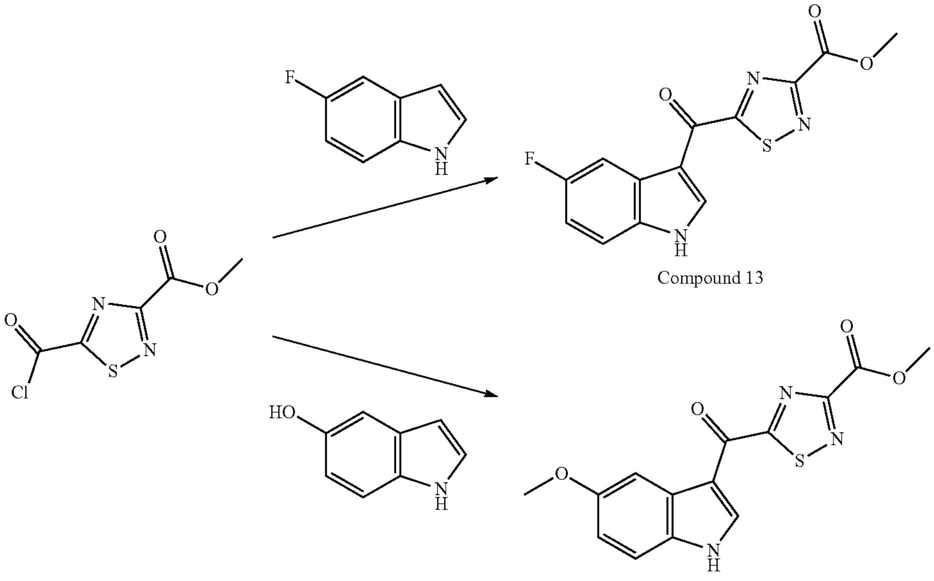
Compound 13
Compound 14
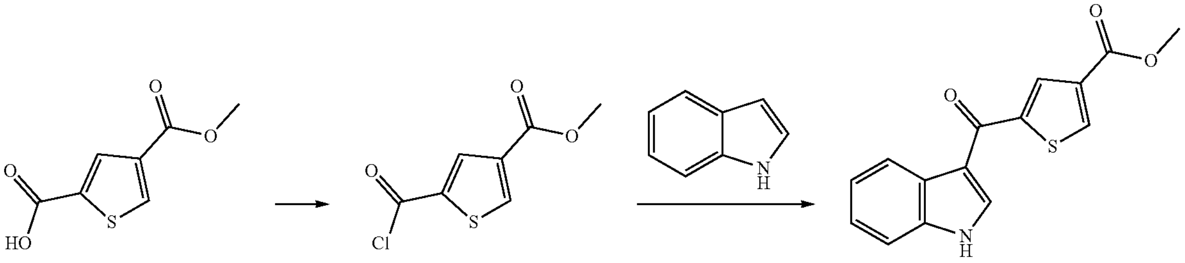
Compound 15
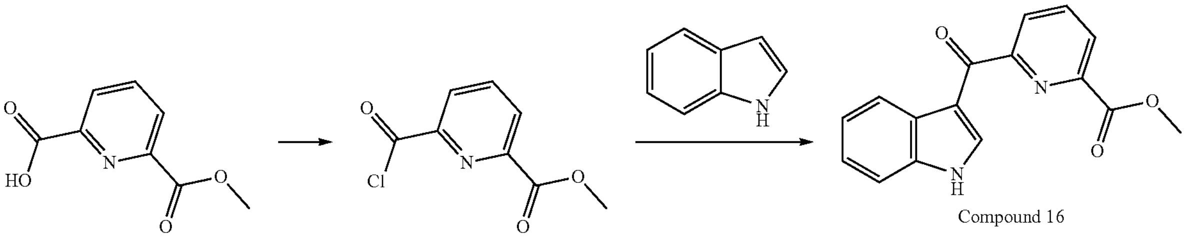
Compound 16
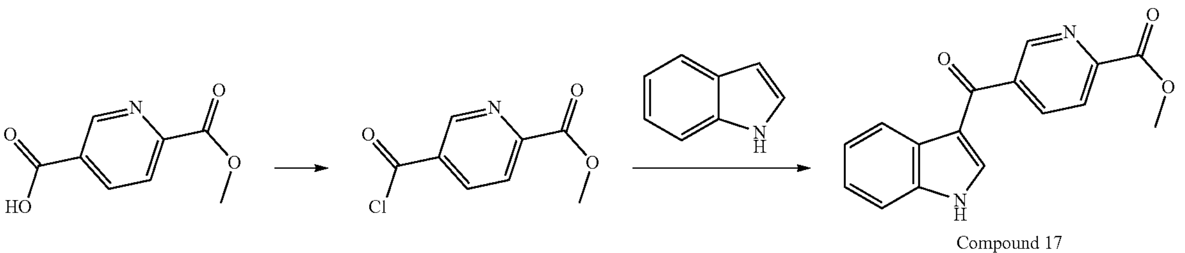
Compound 17
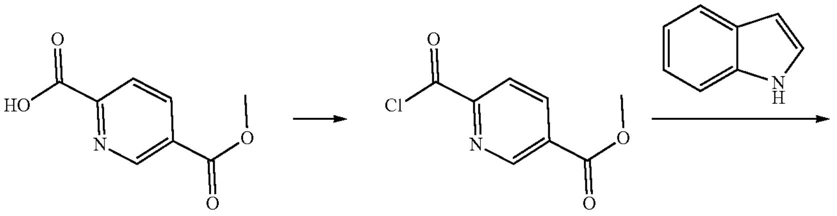

-continued

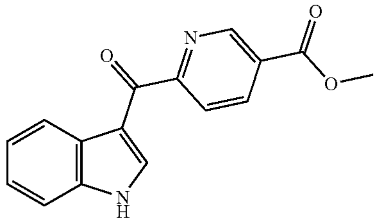

Compound 18

Methods of preparing Compound 9 to 18 were the same as that of Example 8. The difference was that corresponding acid was used in place of Raw material S-2. Other materials were the same as that of Example 8.

Compound 9: MS (ESI) m/z: 271.1 $[M+1]^+$.

Compound 10: $^1H$ NMR (400 MHz, $CDCl_3$): δ 8.79 (brs, 1H), 8.41~8.43 (m, 1H), 8.24 (s, 1H), 7.98 (d, J=2.8 Hz, 1H), 7.48~7.50 (m, 1H), 7.31~7.37 (m, 2H), 3.37~3.43 (m, 1H), 1.49 (d, J=6.8 Hz, 6H).

Compound 11: $^1H$ NMR (400 MHz, DMSO-$d_6$): δ 12.49 (brs, 1H), 9.09 (s, 1H), 8.70 (s, 1H), 8.29~8.34 (m, 1H), 7.58~7.60 (m, 1H), 7.29~7.34 (m, 2H), 3.98 (s, 3H).

Compound 12: $^1H$ NMR (400 MHz, $CDCl_3$): δ 8.73 (brs, 1H), 8.50~8.35 (m, 1H), 7.83 (d, J=3.1 Hz, 1H), 7.55~7.41 (m, 1H), 7.43~7.31 (m, 2H), 6.96 (d, J=4.1 Hz, 1H), 6.69 (d, J=4.2 Hz, 1H), 4.25 (s, 3H), 3.90 (s, 3H).

Compound 13: $^1H$ NMR (400 MHz, DMSO-$d_6$): δ 12.56 (brs, 1H), 9.06 (s, 1H), 7.94 (dd, J=2.8, 9.6 Hz, 1H), 7.65 (dd, J=4.8, 8.8 Hz, 1H), 7.20 (dt, J=2.8, 9.6 Hz, 1H), 4.00 (s, 3H). MS (ESI) m/z: 306.0 $[M+1]^+$.

Compound 14: $^1H$ NMR (400 MHz, DMSO-$d_6$): δ 12.43 (brs, 1H), 8.97 (s, 1H), 7.9 (d, J=2.4 Hz, 1H), 7.52 (d, J=8.8 Hz, 1H), 6.97 (dd, J=2.4, 8.8 Hz, 1H), 3.99 (s, 3H), 3.83 (s, 3H). MS (ESI) m/z: 318.0 $[M+1]^+$.

Compound 15: $^1H$ NMR (400 MHz, $CDCl_3$): δ 9.07 (brs, 1H), 8.41~8.44 (m, 1H), 8.37 (s, 1H), 8.11 (s, 1H), 7.95 (d, J=2.0 Hz, 1H), 7.48~7.50 (m, 1H), 7.34~7.37 (m, 2H), 3.94 (s, 3H). MS (ESI) m/z: 286.0 $[M+1]^+$.

Compound 16: $^1H$ NMR (400 MHz, DMSO-$d_6$): δ 12.22 (brs, 1H), 9.10 (s, 1H), 8.39~8.42 (m, 1H), 8.20~8.30 (m, 3H), 7.53~7.57 (m, 1), 7.26~7.30 (m, 2H), 3.97 (s, 3H). MS (ESI) m/z: 281.0 $[M+1]^+$.

Compound 17: $^1H$ NMR (400 MHz, $CDCl_3$): δ 9.17 (brs, 1H), 8.43~8.47 (m, 1H), 8.30 (brs, 2H), 7.70 (s, 1H), 7.54~7.56 (m, 2H), 7.38~7.40 (m, 2H), 4.09 (s, 3H). MS (ESI) m/z: 286.0 $[M+1]^+$.

Compound 18: $^1H$ NMR (400 MHz, DMSO): δ 12.20 (brs, 1H), 9.23~9.24 (m, 1H), 8.76 (s, 1H), 8.51 (dd, J=8.0, J=2.0, 1H), 8.35~8.52 (m, 1H), 8.14 (dd, J=8.4, J=0.8, 1H), 7.53~7.56 (m, 1H), 7.25~7.31 (m, 2H), 3.95 (s, 3H). MS(ESI) m/z: 281$[M+1]^+$.

Example 19 Compound 19-1, 19-2

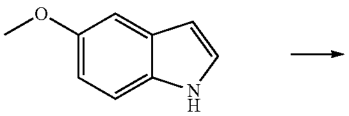

-continued

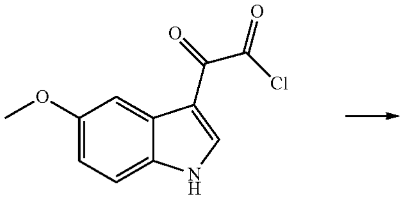

Intermediate 19a

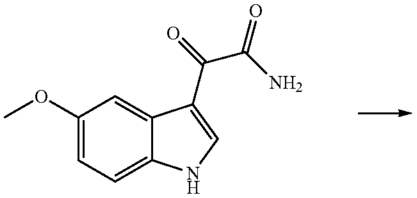

Intermediate 19b

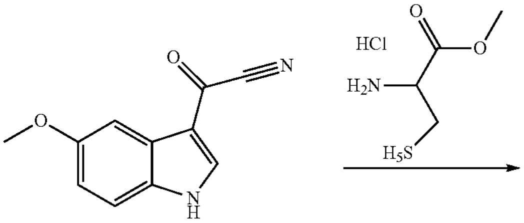

Intermediate 19c

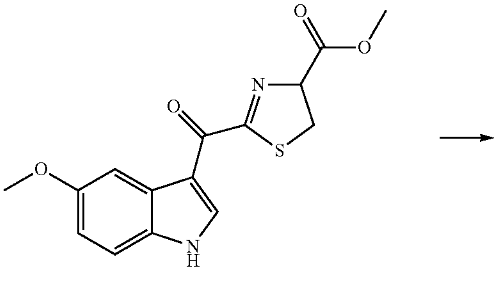

Intermediate 19-1

-continued

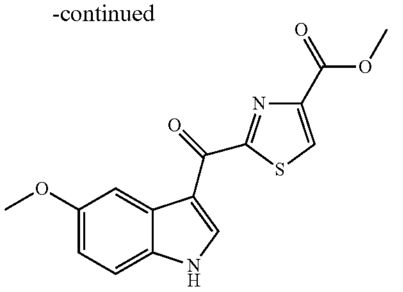

Compound 19-2

Synthesis Intermediate 19a

5-Methoxy indole (10 g, 68 mmol) was added into 250 mL of three-necked flask, then into which methyl tertiary butyl ether (75 mL) was added for dissolution. Reaction system was cooled to −10° C., then into which oxalyl chloride (9.5 g, 74 mmol) was dropped slowly. During this course of dropping, temperature of reaction system was controlled below −5° C. After dropping, reaction system was stirred for 1 h at low temperature. Then ice bath was removed. Reaction system was stirred for 30 minutes at room temperature, then into which petroleum ether (100 mL) was added, stirred for 30 minutes and filtered. Filter cake was washed with a mixture of petroleum ether and methyl tertiary butyl ether, then dried to give Intermediate 19a (15.5 g, yield 97%). LCMS (ESI) m/z: 234 $[M+1]^+$ (the product was diluted with methanol, the acyl chloride was transferred to methyl ester).

Synthesis of Intermediate 19b

Intermediate 19a (15.5 g) was added in batches into a mixture of 52.3 g concentrated ammonia (25%) and 100 mL ethanol at 0° C. After addition, reaction system was kept to react for 2 h at 10° C. Reaction mixture was poured into 100 mL ice water, then stirred for 30 minutes and filtered. Filter cake was dried to give a pale gray solid, i.e. Intermediate 19b (10.5 g). LCMS (ESI) m/z: 219 $[M+1)^+$.

Synthesis of Intermediate 19c

Intermediate 19b (10 g, 45.8 mmol) was suspended in 150 mL ethyl acetate, then into which pyridine (10.87 g, 137.5 mmol) was added. Reaction system was cooled to below 10° C., into which, trifluoroacetic anhydride (14.439, 68.7 mmol) was slowly added dropwise for approximately 30 minutes. After addition, reaction continued for 2 h at 10° C. Reaction solution was poured into 100 mL ice water and extracted with ethyl acetate twice. Organic phase after being combined was washed with saturated sodium bicarbonate twice, and with 0.5N diluted hydrochloric acid twice, then dried over anhydrous sodium sulfate, filtered and concentrated under reduced pressure to give a crude solid of 8.8 g. The crude solid was washed with a mixed solvent of ethyl acetate:dichloromethane=5:1, then filtered to give Intermediate 19c (7.2 g, yield 78%).

$^1$H NMR (400 MHz, $CDCl_3$): δ 12.76 (bis, 1H), 8.53 (s, 1H), 7.48~7.51 (m, 2H), 6.99 (dd, J=8.8 Hz, J=2.4 Hz, 1H), 3.80 (s, 3H). MS (ESI) m/z: 201.0 [M+1]

Synthesis of Compound 19-1

Intermediate 19c (2 g, 10 mmol) was dissolved in N,N'-dimethylformamide (15 mL), then into which L-cysteine methyl ester hydrochloride (1.72 g, 10 mmol) and DBU (152 mg, immol) were added. Reaction system was heated to 40° C. for reacting for 3 h, then cooled to room temperature and dropped into 80 mL ice-dilute hydrochloric acid (containing 0.1 mmol HCl), stirred for 20 minutes and filtered. Filter cake was pressed to dryness and washed with a little dichloromethane and dried to give Intermediate 19-1 (3.1 g, yield 97%).

$^1$H NMR (400 MHz, $CDCl_3$): δ 8.78 (brs, 1H), 8.71 (d, J=2.8 Hz, 1H), 7.97 (d, J=2.8 Hz, 1H), 7.33 (d, J=8.8 Hz, 1H), 6.97 (dd, J=8.8 Hz, J=2.8 Hz, 1H), 5.48 (t, J=8.8 Hz, 1H), 3.92 (s, 3H), 3.89 (t, 3H), 3.61 (d, J=9.6 Hz, 2H). MS (ESI) m/z: 319.0 $[M+1]^+$.

Synthesis of Compound 19-2

Compound 19-1 (2.6 g, 6.16 mmol) was dissolved in N,N-dimethylformamide (30 mL). Reaction system was kept to react at 80° C. by bubbling air for 12 h. Reaction solution was dropped into ice water, then stirred for 20 minutes and filtered. Filter cake was washed with water and dried to give Compound 19-2 (2.5 g, yield 96%).

$^1$H NMR (400 MHz, $CDCl_3$): δ 9.23 (d, J=3.6 Hz, 1H), 9.02 (brs, 1H), 8.44 (s, 1H), 8.05 (d, J=2.4 Hz, 1H), 7.37 (d, J=8.8 Hz, 1H), 6.99 (dd, J=8.8 Hz, J=2.4 Hz, 1H), 4.03 (s, 3H), 3.95 (s, 3H). MS (ESI) m/z: 317.0 $[M+1]^+$.

Example 20 Compound 20-1, 20-2

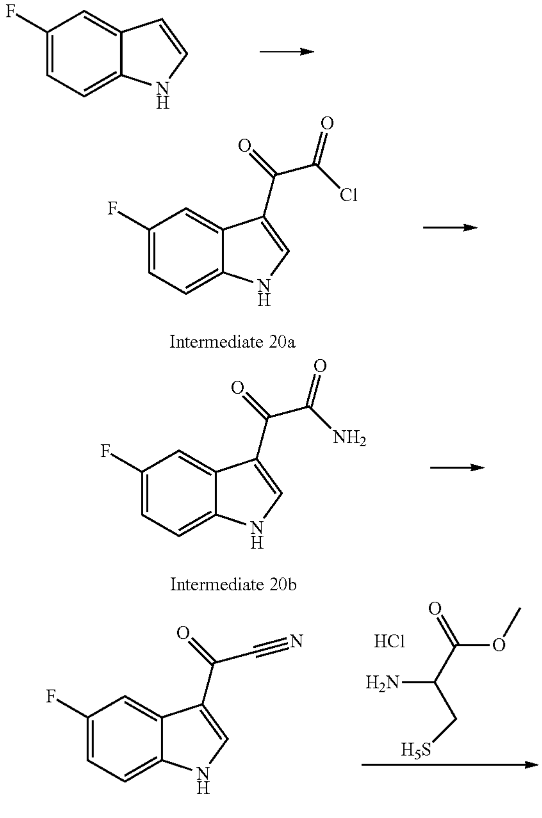

Intermediate 20a

Intermediate 20b

Intermediate 20c

-continued

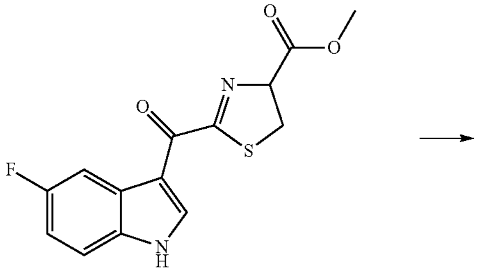

Compound 20-1

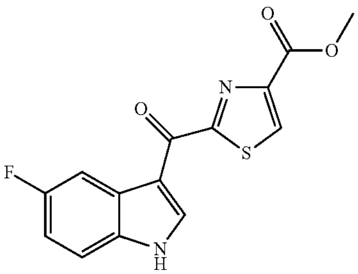

Compound 20-2

Synthetic route of Compound 20-1 and compound 20-2 were the same as that of Example 19. The difference was that 5-fluoro indole was used as starting raw materials to replace of 5-methoxy indole. Identification data of related structures were as follows, Intermediate 20b: MS(ESI) m/z: 207.2[M+1]$^+$.

Intermediate 20c: $^1$H NMR (400 MHz, DMSO-$d_6$): δ 12.94 (brs, 1H), 8.68 (s, 1H), 7.70 (dd, J=2.4, 9.2 Hz, 1H), 7.62 (dd, J=4.4, 8.8 Hz, 1H), 7.24 (dt, J=2.4, 9.2 Hz, 1H). MS(ESI) m/z: 189[M+1]$^+$.

Compound 20-1: $^1$H NMR (400 MHz, DMSO-$d_6$): δ 12.42 (brs, 1H), 8.69 (d, J=3.2 Hz, 1H), 7.87 (dd, J=2.4, 8.8 Hz, 1H), 7.59 (dd, J=4.4, 8.8 Hz, 1H), 7.16 (dt, J=2.4, 9.2 Hz, 1H), 5.67 (dd, J=8.4, 10.0 Hz, 1H), 3.92 (s, 3H), 3.68 (dd, J=11.2, 10.0 Hz, 1H), 3.55 (dd, J=8.4, 11.2 Hz, 1H). MS(ESI) m/z: 307[M+1]$^+$.

Compound 20-2: $^1$H NMR (400 MHz, DMSO-$d_6$): δ 12.48 (brs, 1H), 9.13 (s, 1H), 8.89 (s, 1H), 7.97 (dd, J=2.4, 9.6 Hz, 1H), 7.62 (dd, J=4.4, 8.8 Hz, 1H), 7.17 (dt, J=2.4, 9.2 Hz, 1H), 3.92 (s, 3H). MS(ESI) m/z: 305[M+1]$^+$

Example 21 Compound 21

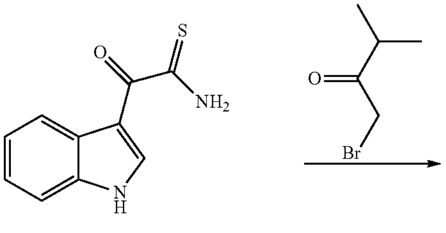

Raw material S3

-continued

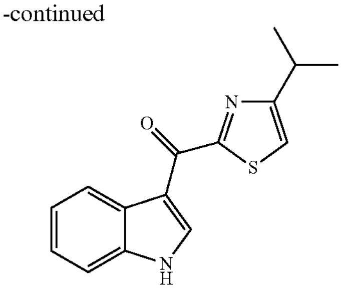

Compound 21

Synthesis of Compound 21

1-bromine-3-methyl-2-butanone (0.8 g, 4.89 mmol) was dissolved in ethanol (25 mL), into which Raw material S3 (1.0 g, 4.89 mmol) was added under stirring. Reaction system was heated to 80° C. and kept to react for 2 h, then cooled to room temperature, filtered and washed with ethanol to give Compound 21 (0.6 g, yield 45%).

$^1$H NMR (400 MHz, DMSO~$d_6$): δ 12.22 (brs, 1H), 9.10 (d, J=3.2 Hz, 1H), 8.31~8.33 (m, 1H), 7.77 (s, 1H), 7.57~7.59 (m, 1H), 7.25~7.31 (m, 2H), 3.16~3.23 (m, 1H), 1.36 (d, J=6.8 Hz, 6H)

Example 22 Compound 22

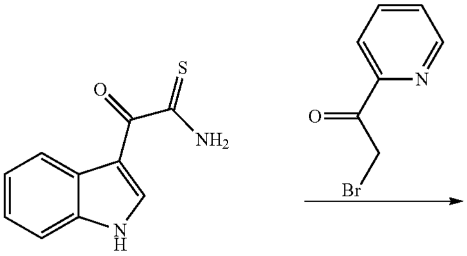

Raw material S3

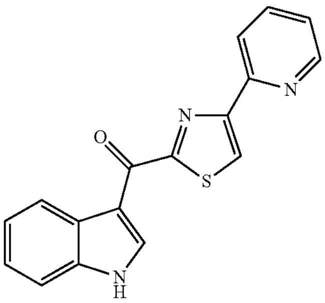

Compound 22

Synthesis of Compound 22 was the same as that of compound 21. Raw material S3 (1.0 g, 4.89 mmol) was used to synthesize Compound 22 (1.2 g, yield 80%).

$^1$H NMR (400 MHz, DMSO~$d_6$): δ 12.30 (brs, 1H), 9.30 (s, 1H), 8.69 (dd, J=1.2, 4.2 Hz, 1H), 8.65 (s, 1H), 8.34~8.36 (m, 1H), 8.32 (d, J=1.2 Hz, 1H), 8.01 (dt, J=2.0, 7.2 Hz, 1H), 7.60~7.62 (m, 1H), 7.44~7.47 (m, 1H), 7.30~7.34 (m, 2H).

Example 23 Compound 23

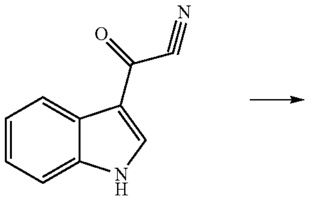

Raw material S4

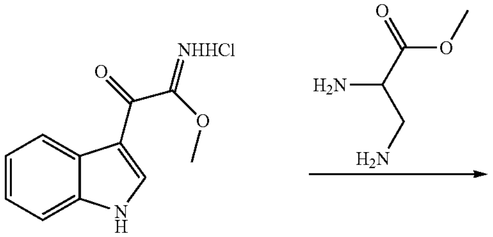

Intermediate 23a

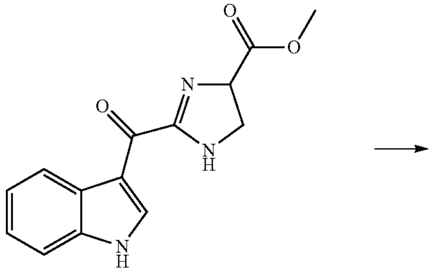

Intermediate 23b

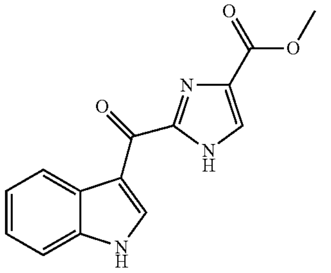

Compound 23

Synthesis of Intermediate 23a

Raw material S4 (4.0 g, 23.5 mmol) was dissolved in methanol (50 mL). Reaction system was cooled to below 0° C. and kept to react for 8 hours, into which dry hydrogen chloride gas continuously aerated. After stopping aeration, reaction system was sealed and stirred overnight, then filtered to give 5.4 g yellow solid, i.e. Intermediate 23a, which was used directly in subsequent reaction.

Synthesis of Intermediate 23b

Intermediate 23a (5.4 g, 19.6 mmol) was dissolved in acetonitrile (15 mL), into which 2,3-diamino propionic acid methyl ester hydrochloride (3.7 g, 19.6 mmol) was added, and then triethylamine (10 g, 98 mmol) was added dropwise. Reaction mixture was refluxed for 5 h, then from which solvent was removed under reduced pressure, and into which dichloromethane and water were added for dissolution and layer. Aqueous phase was extracted with dichloromethane twice. Organic phase after being combined was washed with saturated brine, dried over anhydrous sodium sulfate and concentrated under reduced pressure to give a crude product. The crude product was purified by silica gel column chromatography to obtain Intermediate 23b (2.4 g, yield 45%).

$^1$H NMR (400 MHz, $CDCl_3$): δ 9.19 (s, 1H), 8.91 (d, J=2.8 Hz, 1H), 8.44 (dd, J=6.8 Hz, J=1.6 Hz, 1H), 7.41~7.43 (m, 1H), 7.30~7.36 (m, 2H), 4.67 (brs, 1H), 4.18 (d, J=7.6 Hz, 2H), 3.82 (s, 3H), 1.87 (brs, 1H). MS (ESI) m/z: 272 [M+1].

Synthesis of Compound 23

Intermediate 23b (1.2 g, 4.42 mmol) was dissolved in DMF (20 mL), into which sodium hydroxide (530 mg, 13.3 mmol) was added. Reaction system was stirred to react for 3 hours with aeration of air at 60° C., then cooled and poured into ice water, extracted with ethyl acetate for three times. Organic phase was washed with saturated brine, dried over anhydrous sodium sulfate and concentrated under reduced pressure to give a crude product. The crude product was washed with a mixed solvent of PE:EA=2:1 to give Compound 23 (960 mg, yield 81%).

$^1$H NMR (400 MHz, DMSO): δ 13.69 (brs, 1H), 12.20 (s, 1H), 9.15 (s, 1H), 8.32~8.36 (m, 1H), 8.03 (s, 1H), 7.55~7.59 (m, 1H), 7.24~7.30 (m, 2H), 3.83 (s, 3H). MS(ESI) m/z: 270[M+1]$^+$.

Example 24 Compound 24

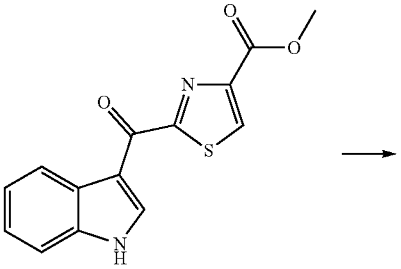

Raw material S1

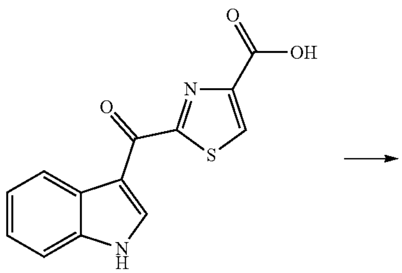

Intermediate 24a

-continued

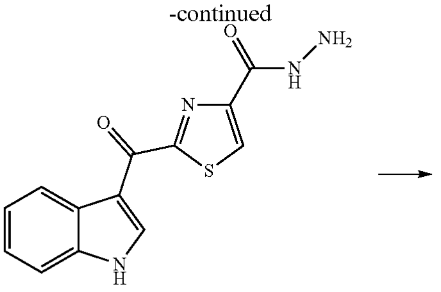

Intermediate 24b

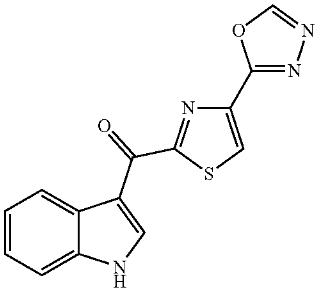

Compound 24

Synthesis of Intermediates 24a

Raw material S1 (2.86 g, 10 mmol) was dissolved in a mixed solvent of THF/MeOH/$H_2O$ (16/15/15 mL). Reaction system was stirred overnight at room temperature. Reaction solution was adjusted to pH=4-5 with 4N hydrochloric acid and then filtered. Filter cake was washed with water and dried in vacuo to give Intermediate 24a (2.6 g, yield 96%). MS(ESI) m/z: 271[M−1]$^-$.

Synthesis of Intermediate 24b

Intermediate 24a (1.36 g, 5 mmol) was dissolved in THF (20 mL), into which 2 drops of DMF was added and oxalyl chloride (755 mg, 6 mmol) was added dropwise. Reaction system was kept at room temperature for 2 h, then concentrated to dryness under reduced pressure and then dissolved in THF (20 mL), then which was added dropwise into 80% hydrazine hydrate (2 mL, 57 mmol) and stirred overnight. Reaction solution was concentrated to 5 mL under reduced pressure and filtered. Filter cake was washed with THF and dried to give Intermediate 24b (1.38 g, yield 97%).

Synthesis of Compound 24

Mixture of Intermediate 24b (1.0 g, 3.5 mmol), p-toluenesulfonic acid monohydrate (20 mg) and trimethyl orthoformate (5 mL) was heated to 80° C. and stirred overnight. Reaction solution was poured into ice water and filtered. Filter cake was washed with ethyl acetate and dried to give Compound 24 (280 mg, yield 27%).

$^1$H NMR (400 MHz, DMSO-$d_6$): δ 12.45 (brs, 1H), 9.43 (s, 1H), 9.15 (s, 1H), 8.95 (s, 1H), 8.32 (m, 1H), 7.61 (m, 1H), 7.32 (m, 2H). MS(ESI) m/z: 297[M+1]$^+$.

Example 25 Compound 25-1, 25-2

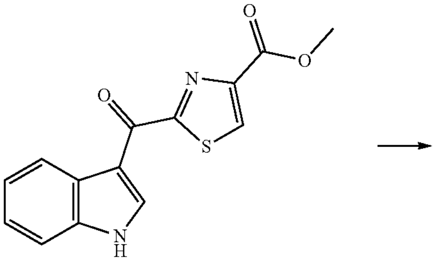

Raw material S1

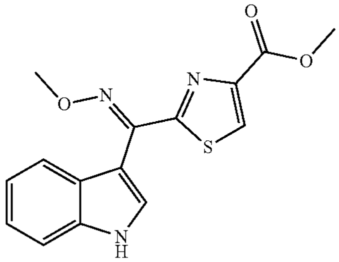

Compound 25-1

+

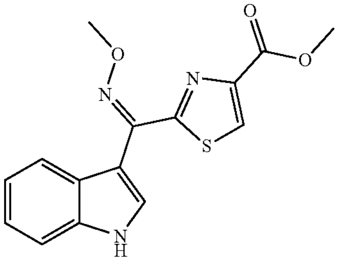

Compound 25-2

Synthesis of Compound 25-1 and Compound 25-2

Raw material S1 (1.0 g, 3.5 mmol) was dissolved in pyridine (15 mL), into which methoxylamine hydrochloride (1.75 g, 21 mmol) was added. Reaction system was heated to 90° C. and kept to react for 24 h, then cooled to room temperature and diluted with water and extracted with ethyl acetate twice. Organic phase was washed with 1N hydrochloric acid twice, then washed with saturated brine, dried over anhydrous sodium sulfate and concentrated under reduced pressure to give a crude product. The crude product was purified by silica gel column chromatography (petroleum ether:ethyl acetate=20:1 to 5:17) to give Compound 25-1 (410 mg) and Compound 25-2 (300 mg). Yield was 64.3%.

Compound 25-1: $^1$H NMR (400 MHz, $CDCl_3$): δ 8.54 (d, J=3.2 Hz, 1H), 8.51 (brs, 1H), 8.42 (s, 1H), 8.37~8.39 (m, 1H), 7.41~7.43 (m, 1H), 7.25~7.29 (m, 2H), 4.32 (s, 3H), 4.00 (s, 3H). MS(ESI) m/z: 316[M+1]$^+$.

Compound 25-2: $^1$H NMR (400 MHz, $CDCl_3$): δ 8.94 (bis, 1H), 8.24 (s, 1H), 7.80 (d, J=2.8 Hz, 1H), 7.40 (d, J=7.6 Hz, 1H), 7.29~7.31 (m, 1H), 7.14~7.18 (m, 1H), 7.09~7.13 (m, 1H), 4.16 (s, 3H), 3.92 (s, 3H). MS(ESI) m/z: 316[M+1]$^+$.

Example 26 Compound 26-1, 26-2

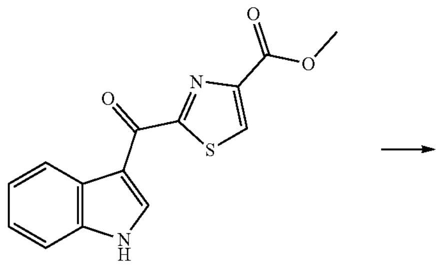

Raw material S1

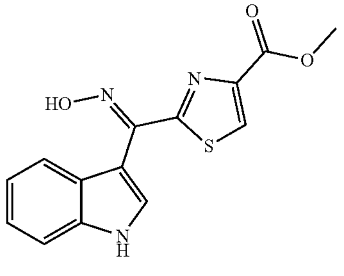

Compound 26-1

+

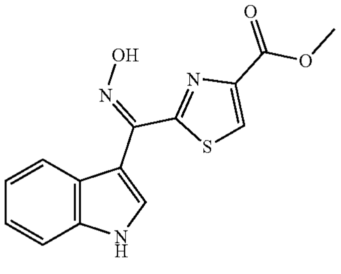

Compound 26-2

Synthesis of Compound 26-1 and Compound 26-2

Synthesis of Compound 26-1 and Compound 26-2 was the same as that of Compound 25-1 and Compound 25-2. Raw material S1 (324 mg, 1.13 mmol) and hydroxylamine hydrochloride (696 mg, 10 mmol) were used to synthesize Compound 26-1 and Compound 26-2 (149 mg, yield 44%).

Compound 26-1: $^1$H NMR (400 MHz, $CDCl_3$): δ 9.00 (s, 1H), 8.26 (s, 1H), 8.19 (d, J=8.0 Hz, 1H), 7.80 (d, J=2.8 Hz, 1H), 7.47 (d, J=8.0 Hz, 1H), 7.09~7.19 (m, 2H), 3.93 (s, 3H). MS(ESI) m/z: 302[M+1]$^+$.

Compound 26-2: $^1$H NMR (400 MHz, $CDCl_3$): δ 8.58 (s, 1H), 8.45 (s, 1H), 8.27 (d, J=3.2 Hz, 1H), 7.40 (dd, J=7.2 Hz, J=1.6 Hz, 1H), 7.33 (d, J=8.0 Hz, 1H), 7.20~7.28 (m 2H), 4.01 (s, 3H). MS(ESI) m/z: 302[M+1]$^+$.

Example 27 Compound 27

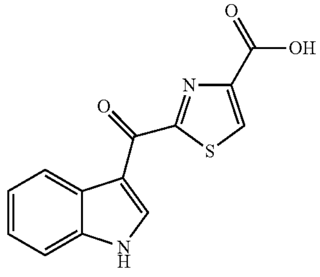

Intermediate 24a

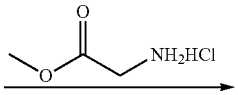

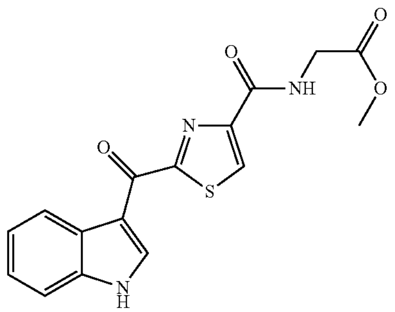

Compound 27

Glycine methyl ester hydrochloride (753 mg, 6 mmol), HATU (2.26 g, 6 mmol) and DIEA (2.3 g, 10 mmol) were added into a solution of Intermediate 24a (1.36 g, 5 mmol) in DMF (20 mL). Reaction system was stirred at room temperature for 2 h. Reaction mixture was poured into 100 mL ice water and filtered. Filter cake was washed with ethyl acetate and dried to give Compound 27 (1.45 g, yield 84.5%).

$^1$H NMR (400 MHz, DMSO-$d_6$): δ 12.40 (d, J=2.0 Hz, 1H), 9.43 (d, J=3.2 Hz, 1H), 9.29 (t, J=2.4 Hz, 1H), 8.66 (s, 1H), 8.32~8.35 (m, 1H), 7.58~7.60 (m, 1H), 7.27~7.34 (m, 2H), 4.13 (d, J=6.4 Hz, 2H), 3.70 (s, 3H)

Example 28 Compound 28

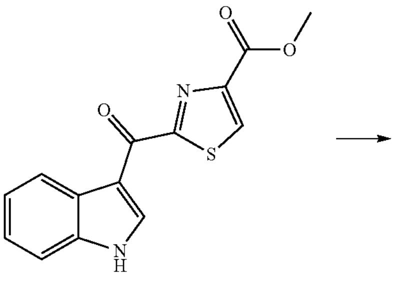

Raw material S1

-continued

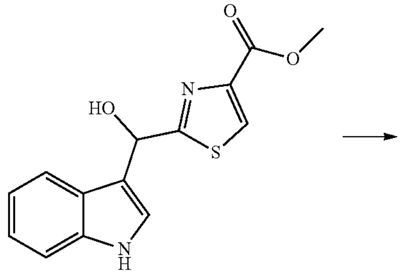

Intermediate 28a

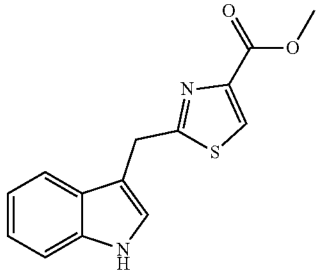

Compound 28

Synthesis of Intermediate 28a

Raw material S1 (7 g, 24 mmol) was dissolved in a mixed solvent of THF (42 mL) and methanol (168 mL). Mixture was cooled to 0° C. by ice-salt bath. Then sodium borohydride was slowly added (4.6 g, 122 mmol) in batches to the mixture. Then the ice-salt bath was removed. Reaction system was raised to room temperature to react for 1 hour. Reaction solution was poured into ice water and filtered. Filter cake was washed with methanol to give Intermediate 28a (6.8 g, yield 98%).

$^1$H NMR (400 MHz, DMSO-$d_6$): δ 11.07 (s, 1H), 8.46 (s, 1H), 7.48 (d, J=8.0 Hz, 1H), 7.37 (d, J=8.0 Hz, 1H), 7.34 (d, J=2.4 Hz, 1H), 7.07 (dt, J=0.8, 8.0 Hz, 1H), 6.96 (dt, J=0.8, 8.0 Hz, 1H), 6.68 (d, J=4.0 Hz, 1H), 6.18 (d, J=4.0 Hz, 1H), 3.77 (s, 3H). MS (ESI) m/z: 291.0 $[M+1]^+$.

Synthesis of Compound 28

Intermediate 28a (3 g, 10.4 mmol) was dissolved in methanol (25 mL), into which zinc powder (2 g, 31.2 mmol) was added under stirring. Reaction system was refluxed for 1 h at 100° C. under protection of nitrogen gas. Reaction solution was dropped to ice water and filtered to give 1.8 g of crude product. Crude product (200 mg) was purified by silica gel column chromatography (PE/EA=4/ito 2/1) to give Compound 28 (20 mg).

$^1$H NMR (400 MHz, DMSO-$d_6$): δ 11.06 (s, 1H), 8.32 (s, 1H), 7.39~7.44 (m, 3H), 7.10 (dt, J=1.1, 8.0 Hz, 1H), 6.98 (dt, J=1.1, 8.0 Hz, 1H), 4.05 (s, 2H), 3.81 (s, 3H). MS (ESI) m/z: 275.0 $[M+I]^+$.

Example 29 Compound 29

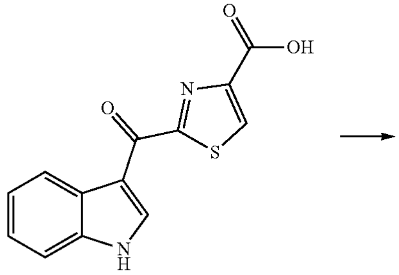

Intermediate 24a

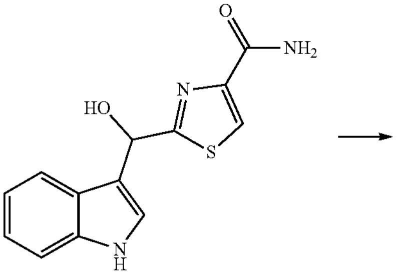

Intermediate 29a

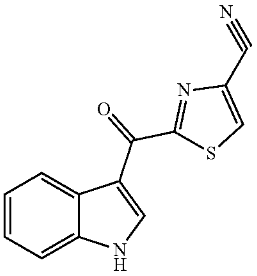

Compound 29

Synthesis of Intermediate 29a

Intermediate 24a (1.36 g, 5 mmol) was dissolved in THF (20 mL), into which 2 drop of DMF was added and oxalyl chloride (755 mg, 6 mmol) were added dropwise. Reaction system was kept to react for 2 h at room temperature, then concentrated under reduced pressure to dryness, and then dissolved in THF (20 mL), which was added dropwise into concentrated ammonia (10 mL). Reaction solution was stirred overnight and concentrated to 5 mL under reduced pressure and filtered. Filter cake was washed with THF and dried to give Intermediate 29a (1.3 g, yield 95%).

$^1$H NMR (400 MHz, DMSO-$d_6$): δ12.27 (s, 1H), 9.52 (s, 1H), 8.61 (s, 1H), 8.31~8.35 (m, 1H), 7.57~7.60 (m, 1H), 8.28 (s, 1H), 7.81 (s, 1H), 7.26~7.34 (m, 2H). MS (ESI) m/z: 272.0$[M+1]^+$.

Synthesis of Compound 29

Intermediate 29a (17 g, 62.66 mmol) was dissolved in ethyl acetate (250 mL), into which pyridine 14.87 g (187.9 mmol) was added, and trifluoroacetic anhydride (19.7 g, 93.99 mmol) was added dropwise at room temperature. Reaction system was stirred at room temperature for 4 h, concentrated to dryness under reduced pressure and then recrystallized with ethyl acetate to give Compound 29 (14 g, yield 88%).

$^1$H NMR (400 MHz, DMSO-$d_6$): δ 12.44 (s, 1H), 9.15 (s, 1H), 9.03 (d, J=3.6 Hz, 1H), 8.28~8.31 (m, 1H), 7.57~7.62 (m, 1H), 7.29~7.34 (m, 2H). MS (ESI) m/z: 254.0[M+1]$^+$.

Example 30 Compound 30-1, 30-2

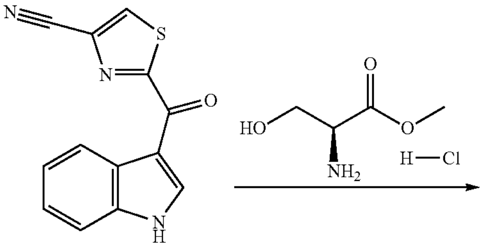

Compound 29

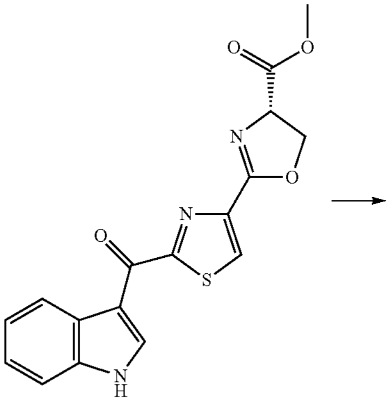

Compound 30-1

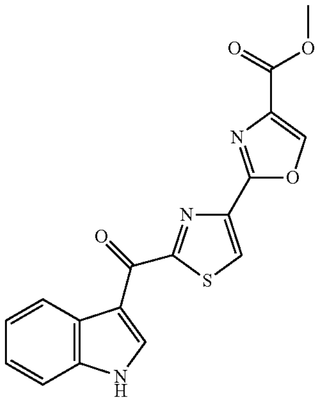

Compound 30-2

Synthesis of Compound 30-1

Compound 29 (1 g, 3.9 mmol) was dissolved in methanol (100 mL), which was replaced with nitrogen gas for three times, into which a solution of sodium methoxide (sodium 0.23 g, 10 mmol; methanol 50 mL) was added dropwise. Reaction system was stirred at room temperature for 4 h, then into which a solution of L-serine methyl ester hydrochloride (1.8 g, 11.6 mmol) in methanol (50 mL) was added dropwise. Reaction system was heated to 55° C. and stirred for 2 h. Reaction solution was poured into ice water and filtered to give a crude product. The crude product was purified by silica gel column chromatography (PE:EA=1:1) to give Compound 30-1 (0.4 g, yield 29%).

$^1$H NMR (400 MHz, DMSO-$d_6$): δ 12.33 (s, 1H), 9.10 (d, J=2.9 Hz, 1H), 8.73 (s, 1H), 8.44~8.21 (m, 1H), 7.69~7.49 (m, 1H), 7.40~7.21 (m, 2H), 5.06 (dd, J=10.0, 8.0 Hz, 1H), 4.76~4.57 (m, 2H), 3.74 (s, 3H). MS (ESI) m/z: 356.0[M+1]$^+$.

Synthesis of Compound 30-2

Compound 30-1 (200 mg, 0.56 mmol) was dissolved in tetrahydrofuran (50 mL), into which manganese dioxide (1000 mg, 11 0.56 mmol) was added. Reaction system was refluxed overnight, cooled and filtered. Filtrate was concentrated to dryness under reduced pressure to give a crude product. The crude product was purified by silica gel column chromatography (PE:EA=2:1) to give Compound 30-2 (25 mg, yield 12%).

$^1$H NMR (400 MHz, DMSO-$d_6$): δ 12.37 (s, 1H), 9.17 (d, J=2.7 Hz, 1H), 9.09 (s, 1H), 8.90 (s, 1H), 8.37~8.29 (m, 1H), 7.66~7.59 (m, 1H), 7.38~7.26 (m, 2H), 3.89 (s, 3H). MS (ESI) m/z: 354[M+1]$^+$.

Example 31 Compound 31-1, 31-2

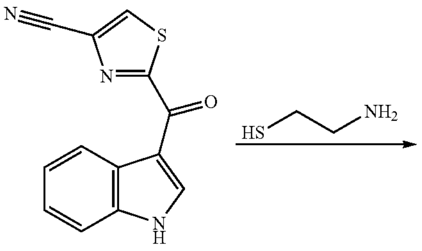

Compound 29

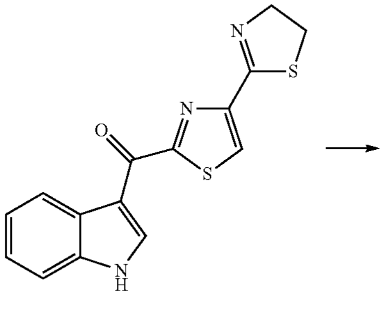

Compound 31-1

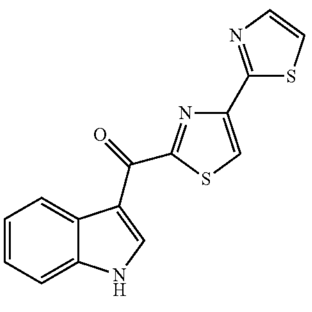

Compound 31-2

Synthesis of Compound 31-1

Synthesis method of Compound 31-1 was the same as that of Compound 30-1.

$^1$H NMR (400 MHz, DMSO-$d_6$): δ 12.41 (s, 1H), 9.08 (d, J=3.1 Hz, 1H), 8.63 (s, 1H), 8.42~8.24 (m, 1H), 7.68~7.49 (m, 1H), 7.31 (m, 2H), 4.47 (t, J=8.5 Hz, 2H), 3.48 (t, J=8.5 Hz, 2H). MS (ESI) m/z: 314.0 $[M+1]^+$.

Synthesis of Compound 31-2

Synthesis method of Compound 31-2 was the same as that of compound 30-2.

$^1$H NMR (400 MHz, DMSO-$d_6$): δ 12.41 (s, 1H), 9.13 (d, J=3.2 Hz, 1H), 8.64 (s, 1H), 8.37~8.30 (m, 1H), 8.01 (d, J=3.2 Hz, 1H), 7.91 (d, J=3.2 Hz, 1H), 7.65~7.57 (m, 1H), 7.35~7.27 (m, 2H). MS (ESI) m/z: 312.0 $[M+1]^+$.

Example 32 Compound 32-1, 32-2

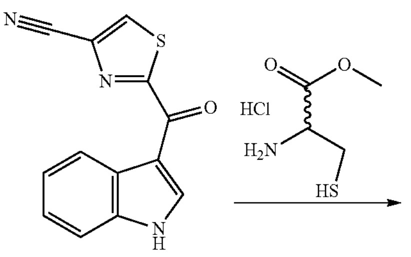

Compound 29

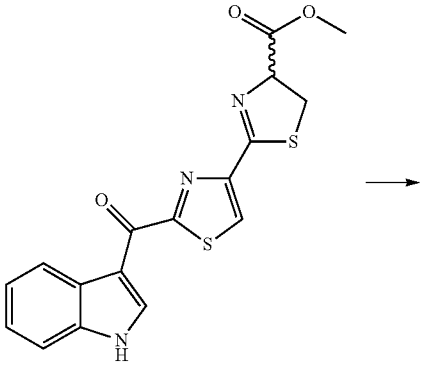

Compound 32-1

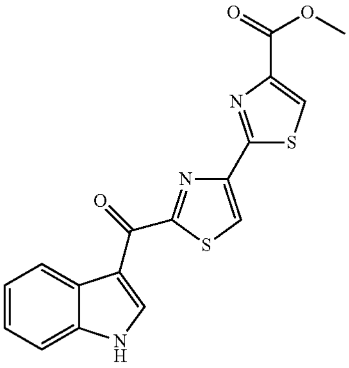

Compound 32-2

Compound 32-1

Synthesis method of Compound 32-1 was the same as that of Compound 30-1.

$^1$H NMR (400 MHz, DMSO-$d_6$): δ 12.43 (s, 1H), 9.04 (s, 1H), 8.70 (s, 1H), 8.29~8.344 (m, 1H), 7.57~7.60 (m, 1H), 7.21~7.34 (m, 2H), 5.48 (dd, J=9.2, 8.4 Hz, 1H), 3.78 (dd, J=6.0, 11.6 Hz, 1H), 3.75 (s, 3H), 3.67 (dd, J=11.6, 8.4 Hz, 1H). MS (ESI) m/z: 372.0$[M+1]^+$.

Compound 32-2

Synthesis method of Compound 32-2 was the same as that of compound 30-2.

MS (ESI) m/z: 370.0$[M+1]^+$.

Example 33 Compound 33-1, 33-2

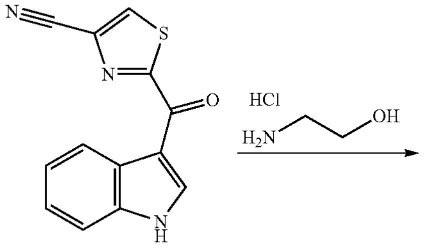

Compound 29

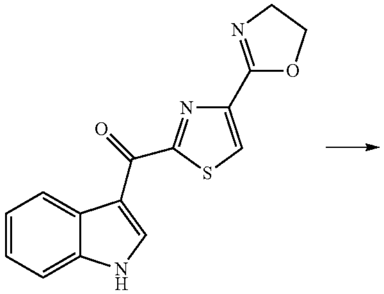

Compound 33-1

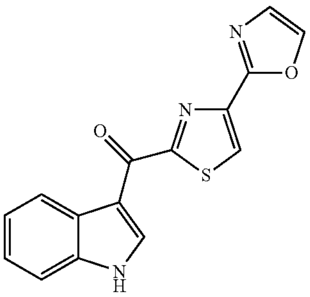

Compound 33-2

Compound 33-1

Synthesis method of Compound 33-1 was the same as that of Compound 30-1.

MS (ESI) m/z: 298.0$[M+1]^+$.

Compound 33-2

Synthesis method of Compound 33-2 was the same as that of compound 30-2.

$^1$H NMR (400 MHz, DMSO-$d_6$): δ 12.41 (s, 1H), 9.13 (d, J=3.2 Hz, 1H), 8.64 (s, 1H), 8.37~8.30 (m, 1H), 7.65~7.57

(m, 1H), 7.52 (brs, 1H), 7.35~7.27 (m, 2H), 7.11 (brs, 1H). MS (ESI) m/z: 296.0[M+1]$^+$.

Example 34 Compound 34

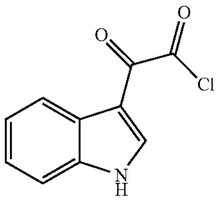

Intermediate 34a

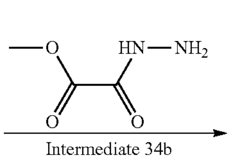

Intermediate 34b

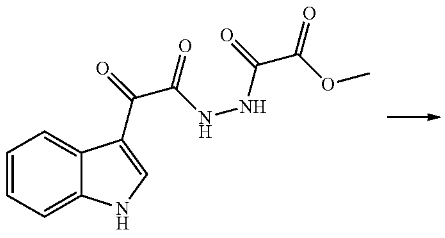

Intermediate 34c

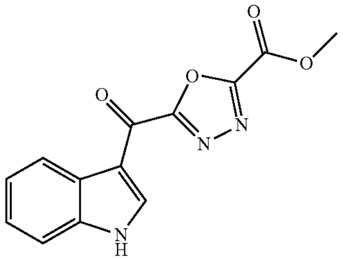

Compound 34

For synthesis of Intermediate 34a, please refer to *J. Am. Chem. Soc.,* 2002, 124(44), 13179-13184.

For synthesis of Intermediate 34b, please refer to *J. Med. Chem.,* 1961, 4, 259-296.

Synthesis of Intermediate 34c

Compound 34b (1.18 g, 10 mmol) and triethylamine (3.03 g, 30 mmol) were dissolved in dichloromethane (15 mL), then into which a solution of Compound 34a (2.07 g, 10 mmol) in dichloromethane (10 mL) was added dropwise at 0° C. Reaction mixture was stirred overnight at room temperature, then diluted with 30 mL water and extracted with dichloromethane for 3 times. Organic phase after being combined was dried over anhydrous sodium sulfate, filtered and concentrated under reduced pressure to give Intermediate 34c (2.8 g, yield 97%).

MS (ESI) m/z: 290.0 [M+1]$^+$.

Synthesis of Compound 34

Intermediate 34c (5 g, 17.286 mmol) was dissolved in DMF (200 mL), into which triethylamine (5.2 g, 51.86 mmol) was added under stirring, then THF (100 mL) was added and p-toluenesulfonyl chloride (9.88 g, 51.86 mmol) dissolved in dichloromethane (50 mL) was slowly added dropwise for 1 hour under protection of nitrogen gas. Reaction system was kept at room temperature overnight, then concentrated under reduced pressure to remove dichloromethane and THF, and then added dropwise to ice water and stirred and filtered to give a crude product. The crude product was purified by silica gel column chromatography (dichloromethane/methanol=50/1-10/1) to give Compound 34 (0.5 g, yield 10%).

$^1$H NMR (400 MHz, DMSO-d$_6$): δ 12.53 (brs, 1H), 8.90 (s, 1H), 8.27~8.29 (m, 1H), 7.60~7.62 (m, 1H), 7.32~7.37 (m, 2H), 4.02 (s, 3H). MS (ESI) m/z: 272.1 [M+1].

Example 35 Compound 35

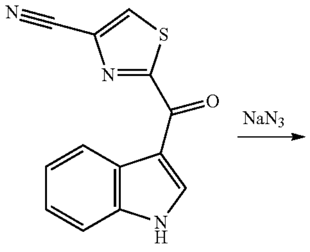

Compound 29

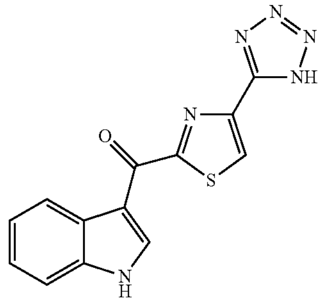

Compound 35

Compound 29 (2 g, 7.9 mmol) was added to a sealed reaction vessel, into which DMF (30 mL) was added and stirred, then ammonium chloride (0.49 g, 9.2 mmol) was added and sodium azide (0.6 g, 9.2 mmol) was added. Then the reaction vessel was sealed and kept to react overnight at 120° C. by oil bath. Reaction solution was cooled to room temperature, then added dropwise to 200 mL of ice water and extracted with ethyl acetate (150 mL). The pH of aqueous phase was adjusted to be acidic by 2N hydrochloric acid to precipitate solid, then filtered, washed with water and dried to give Compound 35 (1.8 g, 77%).

$^1$H NMR (400 MHz, DMSO-d$_6$): δ 12.50 (s, 1H), 9.48 (d, J=3.6 Hz, 1H), 8.88 (s, 1H), 8.36~8.34 (m, 1H), 7.62~7.60 (m, 1H), 7.34~7.31 (m, 2H). MS (ESI) m/z: 297.0 [M+1]$^+$.

Example 36 Compound 36

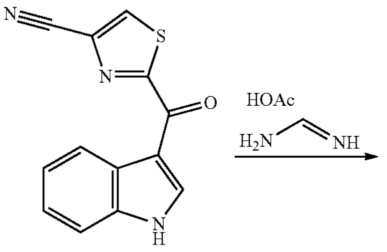

Compound 29

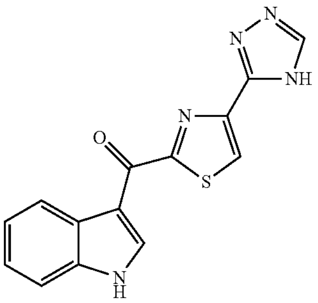

Compound 36

Compound 29 (0.5 g, 1.7 mmol) was suspended in 10 mL ethylene glycol methyl ether, into which 2 mL acetic acid and formamidine acetate (0.215 g, 2.07 mmol) were added. Reaction system was reflux for 24 hours by an oil bath under protection of nitrogen gas, then distilled under reduced pressure. Crude product was purified by silica gel column chromatography (DCM/methanol=200/1-20/1) to give Compound 35 (0.32 g, yield 55%).

$^1$H NMR (400 MHz, DMSO-$d_6$): δ 12.41 (s, 1H), 10.6 (s, 1H), 10.05 (s, 1H), 9.55 (s, 1H), 8.72 (s, 1H), 8.32~8.34 (m, 1H), 7.58~7.59 (m, 1H), 7.28~7.33 (m, 2H). MS (ESI) m/z: 296.0 $[M+1]^+$.

Example 37 Compound 37

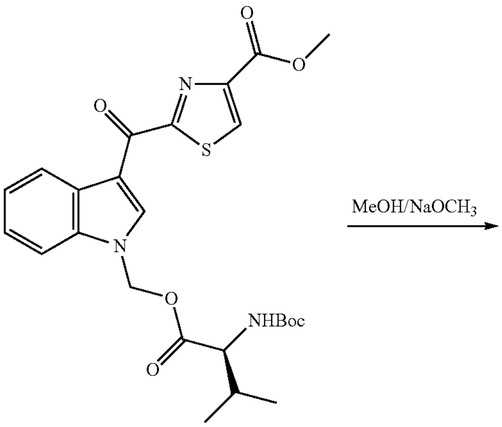

Compound 1-1

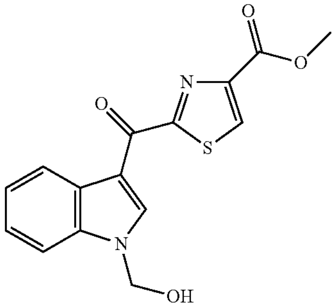

Compound 33

Compound 1-1 (500 mg, 0.97 mmol) was dissolved in methanol (2 mL), into which 0.1N sodium methoxide solution (2 mL) was added dropwise. Reaction system was kept at room temperature overnight and then filtered. Solid was washed with methanol and dried to give Compound 37 (153 mg, yield 50%).

$^1$H NMR (400 MHz, $CDCl_3$): δ 9.25 (s, 1H), 8.93 (s, 1H), 8.35 (d, J=7.6 Hz, 1H), 7.81 (d, J=7.6 Hz, 1H), 7.39~7.47 (m, 2H), 6.92 (t, 1H), 5.6 (d, 2H), 3.94 (s, 3H). MS(ESI) m/z:317 $[M+I]^+$.

Example 38 Compound 38-1 to Compound 38-4

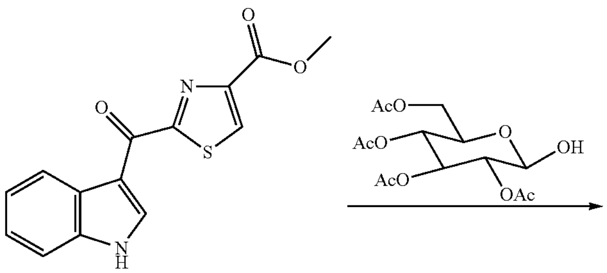

Raw material S-1

-continued

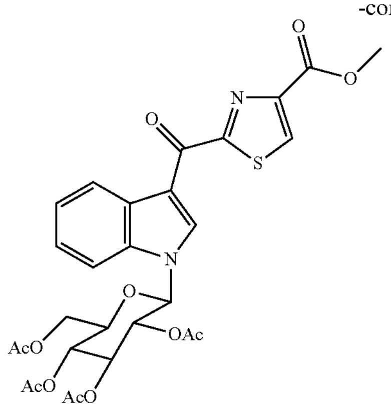

+

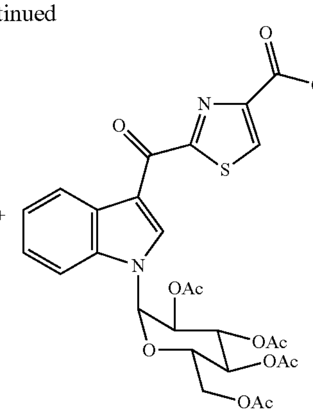

Compound 38-1

Compound 38-2

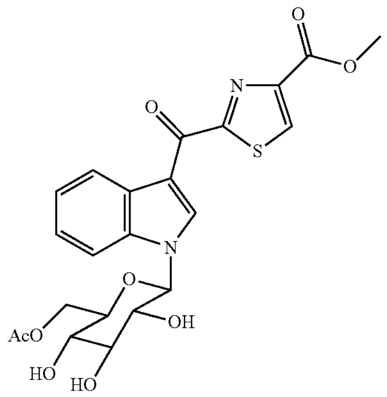

+

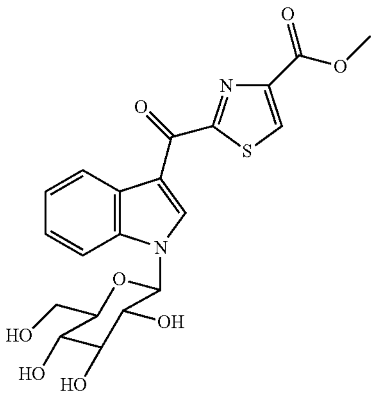

Compound 38-3

Compound 38-4

Synthesis of Compound 38-1, 38-2

Raw material S-1 (1.07 g, 3.78 mmol) was dissolved in THF (50 mL), into which 2, 3, 4, 6-tetraacetyl glucose (2.6 g, 7.55 mmol) was added, and then triphenylphosphine (2 g, 7.55 mmol) was added under protection of nitrogen gas. Reaction system was cooled to −15° C., then into which diisopropyl azodicarboxylate (1.53 g, 7.55 mmol) was added dropwise. Reaction solution was poured into ice water, extracted with ethyl acetate (100 mL×2), dried over anhydrous sodium sulfate, concentrated to dryness under reduced pressure and purified by silica gel column chromatography (petroleum ether/ethyl acetate: 10/1-2/1) to give Compound 38-1 (650 mg) and Compound 38-2 (600 mg) (yield 54%).

Compound 38-1: $^1$H NMR (400 MHz, $CDCl_3$): $^1$H NMR (400 MHz, $CDCl_3$): δ 9.18 (s, 1H), 8.52~8.54 (m, 1H), 8.44 (s, 1H), 7.60~7.63 (m, 1H), 7.38~7.42 (m, 2H), 5.72 (d, J=9.2 Hz, 1H), 5.64 (t, J=9.2 Hz, 1H), 5.50 (t, J=9.6 Hz, 1H), 5.40 (d, J=9.6 Hz, 2H), 4.35 (dd, J=4.8, 12.4 Hz, 2H), 4.27 (dd, J=2.4, 12.4 Hz, 1H), 4.07 (s, 3H), 4.05~4.10 (m, 1H), 2.16 (s, 3H), 2.13 (s, 3H), 2.05 (s, 3H), 1.74 (s, 3H); MS (ESI) m/z: 617.14 $[M+I]^+$.

Compound 38-2: δ 9.20 (s, 1H), 8.56~8.49 (m, 1H), 8.45 (s, 1H), 7.87~7.80 (m, 1H), 7.44~7.35 (m, 2H), 5.92 (d, J=5.2 Hz, 1H), 5.35 (t, J=2.3 Hz, 1H), 4.99 (dt, J=9.4, 1.7 Hz, 1H), 4.38~4.25 (m, 2H), 4.21~4.12 (m, 2H), 4.04 (s, 3H), 2.21 (s, 3H), 2.18 (s, 3H), 2.16 (s, 3H), 2.07 (s, 3H); MS (ESI) m/z: 617.14 $[M+1]^+$.

Synthesis of Compound 38-3, 38-4

Compound 38-1 (200 mg, 0.325 mmol) was dissolved in methanol (10 mL), into which sodium methoxide (190 mg 3.57 mmol) was added. Reaction system was stirred at room temperature for 5 h, then poured into saturated aqueous sodium chloride, then into which 50 mL ethyl acetate was added, and adjusted pH to neutral by use of citric acid. Organic phase was separated and aqueous phase was extracted once with ethyl acetate. Organic phase after being combined was dried over anhydrous sodium sulfate, filtered, concentrated to dryness under reduced pressure and purified by silica gel column chromatography (methanol/dichloromethane: 5%-10%) to give Compound 38-3 (40 mg) and Compound 38-4 (5 mg).

Compound 38-3: MS (ESI) m/z: 491.1 $[M+1]^+$.

Compound 38-4: MS (ESI) m/z: 449.1 $[M+1]^+$.

Example 39 Compound 39

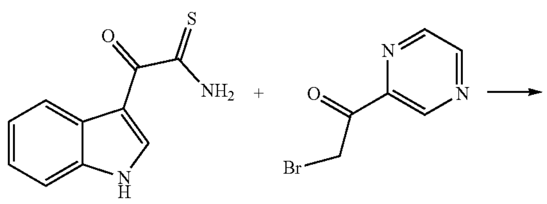

Raw material S3

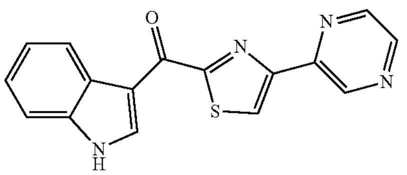

Compound 39

Synthesis method of compound 39 was the same as that in Example 21 to give Compound 39 (yield 65%).

$^1$H NMR (400 MHz, DMSO-$d_6$): δ 12.25 (s, 1H), 9.58 (d, J=0.8 Hz, 1H), 9.38 (d, J=3.2 Hz, 1H), 8.79 (s, 1H), 8.76 (d, J=1.2 Hz, 1H), 8.72 (d, J=2.4 Hz, 1H), 8.34~8.36 (m, 1H), 7.60~7.63 (m, 1H), 7.28~7.33 (m, 2H). MS(ESI) m/z: 307[M+1]$^+$.

Example 40 Compound 40

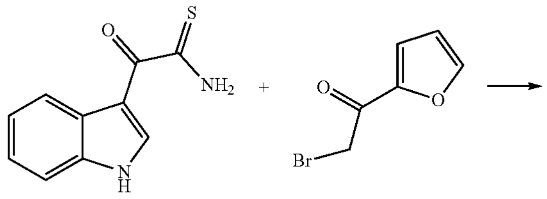

Raw material S3

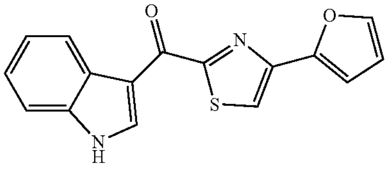

Compound 40

Synthesis method of compound 40 was the same as that in Example 21 to give Compound 40 (yield 58%).

$^1$H NMR (400 MHz, DMSO-$d_6$): δ 12.29 (s, 1H), 9.23 (d, J=3.2 Hz, 1H), 8.33~8.36 (m, 1H), 8.21 (s, 1H), 7.85 (d, J=0.8, 1H), 7.59~7.61 (m, 1H), 7.27~7.33 (m, 2H), 7.13 (d, J=2.8 Hz, 1H), 6.69~6.71 (m, 1H). MS(ESI) m/z: 295[M+1]$^+$.

Example 41 Compound 41

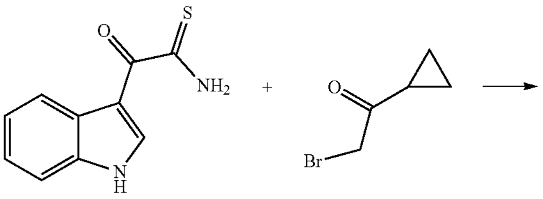

Raw material S3

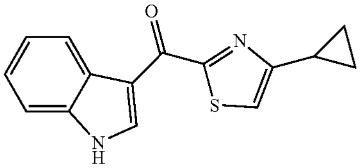

Compound 41

Synthesis method of compound 41 was the same as that in Example 21 to give Compound 41 (yield 58%).

$^1$H NMR (400 MHz, DMSO-$d_6$): δ 12.19 (s, 1H), 8.99 (d, J=3.2 Hz, 1H), 8.30 (m, 1H), 7.71 (s, 1H), 7.60 (m, 1H), 7.27 (m, 2H), 2.24 (m, 1H), 1.01 (d, J=6.8 Hz, 4H). MS(ESI) m/z: 269[M+1]$^+$.

Example 42 Compound 42-1 to Compound 42-2

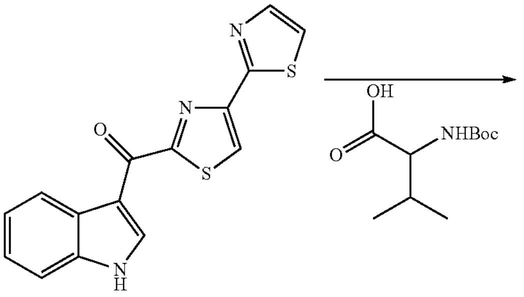

Compound 31-2

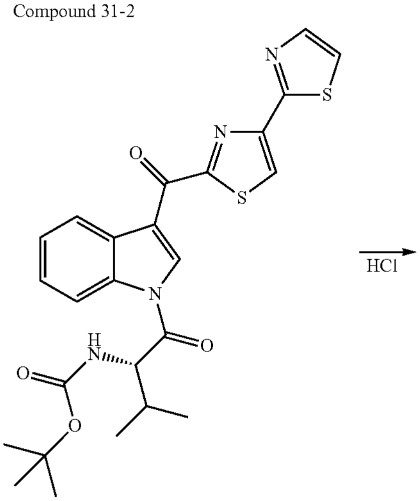

Compound 42-1

-continued

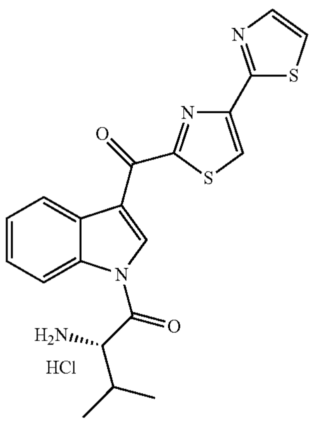

Compound 42-2

Synthesis method of compound 42-1 was the same as that in Example 4 to give Compound 42-1 (yield 83%). MS(ESI) m/z: 511.1[M+1]$^+$.

Compound 42-2 (yield 90%), $^1$H NMR (400 MHz, $CDCl_3$): δ 9.58 (s, 1H), 9.04 (s, 1H), 8.89 (brs, 3H), 8.78 (m, 1H), 8.46~8.51 (m, 1H), 8.35~8.38 (m, 1H), 8.03 (d, J=3.2 Hz, 1H), 7.96 (d, J=3.2 Hz, 1H), 7.54~7.62 (m, 2H), 5.13 (m, 1H), 2.54~2.59 (m, 1H), 1.15 (d, J=7.2 Hz, 3H), 1.07 (d, J=7.2 Hz, 3H). MS(ESI) m/z: 411.1[M+1]$^+$.

Example 43 Compound 43-1 to Compound 43-2

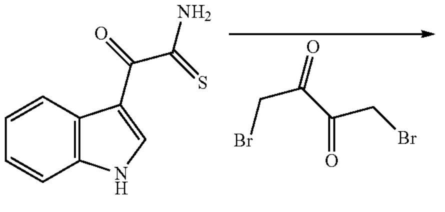

Raw material S3

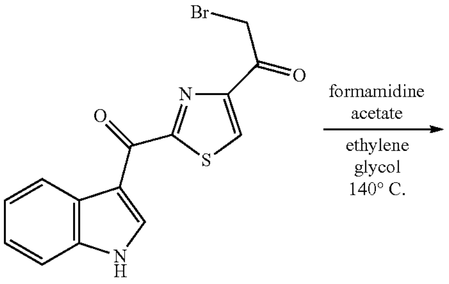

Compound 43-1

-continued

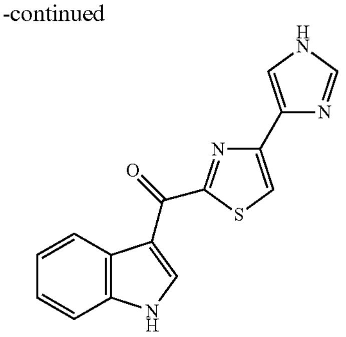

Compound 43-2

Synthesis method of Compound 43-1 was the same as that in Example 21. Yield was 78%, MS(ESI) m/z:349[M+1]$^+$.

Compound 43-1 (1.8 g, 5.15 mmol) was added to ethylene glycol (35 mL), then into which formamidine acetate (2.68 g, 25.77 mmol) was added. Reaction system was kept at 140° C. (external temperature) for 2 hours under protection of $N_2$, then cooled and added into ice water, then into which an aqueous solution of sodium hydroxide was added to adjust pH=9 to 10, and extracted with EA. Organic phases were combined, dried, distilled under reduced pressure to remove solvent. Solid was washed with mixture of EA and a small amount of ethanol and filtered. Crude product was dissolved in THF, filtered by silica gel, washed with THF, concentrated and then washed with mixture of THF/petroleum ether, then filtered to give 380 mg of Compound 43-2.

$^1$H NMR (400 MHz, DMSO) δ=12.37 (s, 1H), 12.45 (s, 1H), 9.38 (s, 1H), 8.33~8.38 (m, 1H), 8.04 (s, 1H), 7.79 (s, 2H), 7.58~7.63 (m, 1H), 7.26~7.33 (m, 2H). MS(ESI) m/z: 295[M+1]$^+$.

Example 44 Compound 44

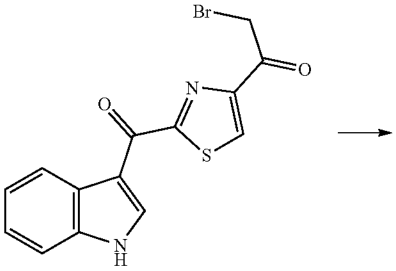

Compound 43-1

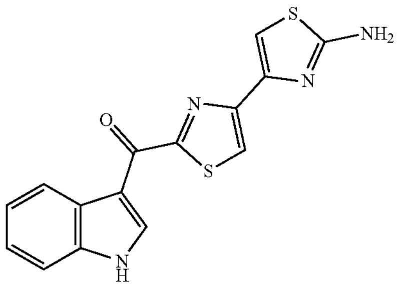

Compound 44

Compound 43-1 (1.5 g, 4.3 mmol) was dissolved in ethanol (25 mL), into which thiourea (327 mg, 4.3 mmol)

was added. Reaction system was kept at 80° C. for 3 h. After completion of reaction, reaction solution was cooled, filtered, washed with aqueous sodium bicarbonate, dried, dissolved with THF, filtered through silica gel. Filtrate was concentrated and washed with EA to give 1.2 g of Compound 44 (yield 85.6%).

$^1$H NMR (400 MHz, $CDCl_3$) δ=12.26 (d, J=2.4 Hz, 1H), 9.27 (d, J=3.2 Hz, 1H), 8.32~8.36 (m, 1H), 7.99 (s, 1H), 7.58~7.61 (m, 1H), 7.26~7.32 (m, 3H), 7.21 (s, 2H). MS(ESI) m/z: 327[M+1]$^+$.

Effect Example 1

AhR agonist assay (please refer to activity assay of MeBio agonist: Oncogene (2004) 23, 4400-4412)

Experimental material (plasmids): cells of reporter gene expressing natural (Human Hepatoma Huh-7) AhR receptor, in which reporter vector comprises a functional firefly luciferase gene connecting to an upstream receptor specific genetic response element (GRE).

AhR agonist test includes following three steps:

1, Implanting into cells: a suspension of reporter cell of AhR receptor was prepared in cell recovery medium (CRM; containing 10% charcoal-treated FBS). Then the suspension (100 μL) was assigned to wells in a white culture plate with 96 wells.

2, Before the experiment was about to begin, Master Stocks was diluted to be a processing medium of "concentration of 2 X" by use of appropriate compound screening assay medium (CSM: containing 10% charcoal-treated FBS). Test compounds were diluted with gradient method by use of CSM medium containing 0.2% DMSO to make the final concentration of DMSO in each well of each treatment group being 0.1%. The processing medium was added to culture plate (100 μL/well) on which cells containing reporter gene had been laid in advance in wells by means of double duplicate. The culture plate was placed in an incubator of 37° C. for 24 hours.

3, Fluorescence detection and analysis: after incubation, the processing medium was discarded and luciferase detection reagent was added 100 μL/well. Ave RLU (mean relative fluorescence intensity) of each well and coefficient of variation for each set of experiments were detected. Ratio of Ave $RLU^{Test\ Cmpd}$ of treatment groups with test compound of different concentrations to Ave $RLU^{Vehicle}$ of blank control group can determine activity quantitatively of AhR receptor under influence of test compound of different concentrations and activating multiples as well as $EC_{50}$.

$$\text{Coefficient of variation } (\%\ CV) = 100 \times \frac{SD}{AveRLU};$$

$$\text{Activating multiples} = \frac{AveRLU^{Test\ Cmpd}}{AveRLU^{Vehicle}}.$$

Processing method of data may refer to *J. Biomol. Screen*, 1999, 4(2), 67-73.

$EC_{50}$ of each compound was shown in Table 1, wherein A indicates 0.001 μM<$EC_{50}$≤1.0 μM; B indicates 1.0 μM<$EC_{50}$≤10.0 μM; C indicates 10.0 μM<$EC_{50}$≤100 μM.

TABLE 1

$EC_{50}$ of each test compound.

| Test compound | $EC_{50}$ (nM) |
|---|---|
| 1-2 | A |
| 2-2 | A |
| 3 | A |
| 4-2 | A |
| 5 | A |
| 6 | A |
| 7 | A |
| 8 | B |
| 9 | A |
| 10 | C |
| 11 | C |
| 12 | A |
| 13 | B |
| 14 | B |
| 15 | C |
| 16 | A |
| 17 | C |
| 18 | B |
| 19-1 | A |
| 19-2 | A |
| 20-1 | A |
| 20-2 | A |
| 21 | A |
| 22 | A |
| 23 | A |
| 24 | A |
| 25-1 | B |
| 25-2 | B |
| 26-1 | B |
| 26-2 | B |
| 27 | A |
| 28 | C |
| 29 | A |
| 30-1 | A |
| 30-2 | A |
| 31-1 | A |
| 31-2 | A |
| 32-1 | A |
| 32-2 | A |
| 33-1 | A |
| 33-2 | A |
| 34 | B |
| 35 | B |
| 36 | A |
| 37 | A |
| 38-1 | A |
| 38-2 | A |
| 38-3 | A |
| 38-4 | A |
| 39 | A |
| 40 | A |
| 41 | A |
| 42-2 | A |
| 43-2 | A |
| 44 | A |
| 42-1 | A |

It can be found in Table 1 that each of test compound above may be coupled to AhR and regulate those functions and signal pathways controlled by AhR, further affect growth and proliferation of cancer cells and invasiveness of tumor cell. Thus pharmaceutical composition of compounds shown in formula (I) in the present disclosure can be used as AhR inhibitor or non-constitutive AhR agonists (non-constitutive AhR agonists) for inhibiting growth of cancer cell and inhibiting metastasis and invasion of tumor cells.

INDUSTRIAL APPLICABILITY

The invention discloses an aryl hydrocarbon receptor modulators of formula (I), and pharmaceutically acceptable salts thereof, (I)

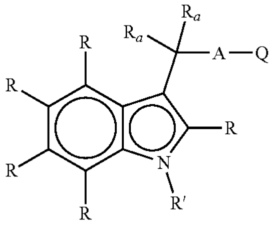

R' is H, CN, $CH_2(OH)R_0$, $C_mH_{2m+1}$, $C_nH_{2n-1}$, $C_nH_{2n-3}$,

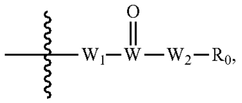

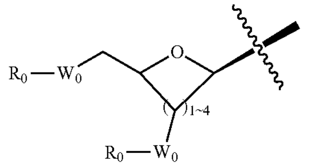

or

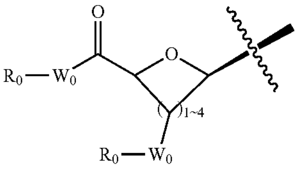

;

Two $R_a$ is independently H, or two $R_a$ together form =O or =N—$W_3$—$R_1$; A is a $C_6$ to $C_{10}$ aromatic ring, or a $C_2$ to $C_{10}$ heteroaromatic ring containing 1 to 5 heteroatom selected from N, O and S, or 4 to 7 membered non-aromatic heterocyclic ring containing 1 to 3 heteroatom selected from N, O and S and containing C=N, which are unsubstituted or substituted by 1 or 3 R;

Q is R, or a $C_6$ to $C_{10}$ aromatic ring, or a $C_2$ to $C_{10}$ heteroaromatic ring containing 1 to 5 heteroatoms selected N, O and S, which are unsubstituted or substituted by 1 or 3 R;

R is $R_c$ connected with C or RN connected with N.

Compounds of this invention of formula (I) can modulate activity of AhR for inhibiting growth of cancer cell and inhibiting migration and invasion of tumor cell.

The foregoing description of the exemplary embodiments of the present invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. An aryl hydrocarbon receptor modulator of formula (I), or a pharmaceutically acceptable salt thereof, (I)

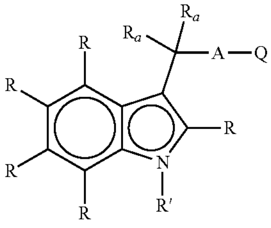

wherein R' is CN, $CH(OH)R_0$, $C_mH_{2m+1}$, $C_nH_{2n-1}$, $C_nH_{2n-3}$,

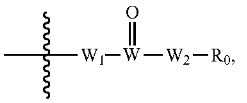

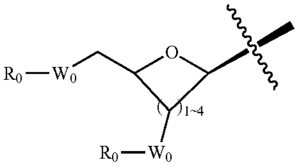

or

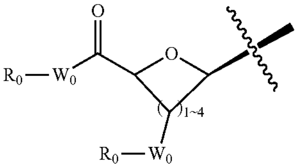

;

wherein $W_0$ is O or NH; $W_1$ is bond, $C(R_0)_2$, $C(R_0)_2O$, $C(R_0)_2OC(R_0)_2$ or $C(R_0)_2OC(R_0)_2C(R_0)_2$; W is C, S or S(O), or $P(OR_0)$, such that when W is C, S or S(O), $W_2$ is bond, O, $NR_0$, $CH(N(R_0)_2)$ or $OCH_2C(O)$; when W is $P(OR_0)$, $W_2$ is O or $NR_0$; each $R_0$ is independently H, $C_mH_{2m+1}$, $C_mH_{2m+1}OC(O)$, $C_mH_{2m+1-r}X_r$, $C_mH_{2m+1}OC(O)C_mH_{2m}$, (cyclic $C_4H_8NO)C_mH_{2m}$, $CH_3(OCH_2CH_2)_u$ or $CH_3(OCH_2CH_2)_uOCH_2$;

two $R_a$ are independently H, or two $R_a$ together form =O, =N—CN or =N—$W_3$—$R_1$; when $W_3$ is O or NH, $R_1$ is H, $C_mH_{2m+1}$, $C_mH_{2m+1}C(O)$, $C_mH_{2m+1}OC(O)$ or $C_mH_{2m+1}S(O)_{1\sim2}$;

A is $C_2$ to $C_{10}$ heteroaromatic ring containing 2 to 5 heteroatoms selected from N, O and S, or a 4 to 7 membered non-aromatic heterocyclic ring containing 1 to 3 heteroatoms selected from N, O and S and containing C=N, which are with no substituent or substituted by 1 to 3 R;

Q is R, or $C_6$ to $C_{10}$ aromatic ring with no substituent or substituted by 1 to 3 R; or 3 to 10 membered heterocyclic ring with no substituent or substituted by 1 to 3 R, which contain 1 to 5 heteroatoms selected N, O and S;

R is $R_c$ connected with C or $R_N$ connected with N, wherein each $R_c$ is independently X, CN, R", —Y—OR", —Y—C(O)R", —Y—OC(O)R", —Y—C(O)OR", —Y—OC(O)OR", —Y—NR"$_2$, —Y—C(O)NR"$_2$, —Y—NR"C(O)R", —Y—NR"C(O)NR"$_2$, —Y—OC(O)NR"$_2$, —Y—NR"C(O)OR", —Y—S(O)$_{1\sim2}$R", —Y—$S(O)_{1\sim2}NR''_2$ or —Y—$NR''S(O)_{1\sim2}R''$; each $R_N$ is independently CN, R'', —Y—OR'', —Y—C(O)R'', —Y—OC(O)R'', —Y—C(O)OR'', —Y—OC(O)OR'', —Y—$NR''_2$, —Y—$C(O)NR''_2$, —Y—NR''C(O)R'', —Y—$NR''C(O)NR''_2$, —Y—$OC(O)NR''_2$, —Y—NR''C(O)OR'', —Y—$S(O)_{1\sim2}R''$, —Y—$S(O)_{1\sim2}NR''_2$ or —Y—$NR''S(O)_{1\sim2}R''$;

R'' is H, D, $C_mH_{2m+1}$, $C_nH_{2n-1}$, $C_nH_{2n-3}$, $C_mH_{2m+1-r}X_r$, $C_nH_{2n-1-s}X_s$ or $C_nH_{2n-3-t}X_t$;

Y is bond, —$C_mH_{2m}$—, —$C_nH_{2n-2}$—, —$C_nH_{2n-4}$—, —$C_mH_{2m-i}X_i$—, —$C_nH_{2n-2-j}X_j$— or —$C_nH_{2n-4-k}X_k$—;

m is 1 to 8, n is 2 to 8, u is 1 to 5, r≤2m+1, s≤2n−1, t≤2n−3, i≤2m, j≤2n−2, k≤2n−4, X is F, Cl or Br, and when two $R_a$ are independently H, A is not thiazole.

2. The aryl hydrocarbon receptor modulator of claim 1, wherein when A is

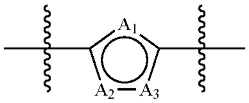

, formula (I) turns into formula (I1), (I1)

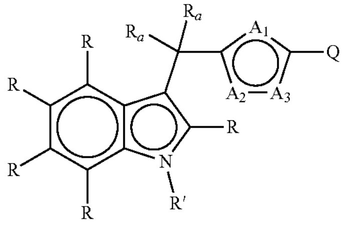

and wherein in formula (I1), one of $A_1$, $A_2$ and $A_3$ is O, S or N(R), the rest two are each independently C(R) and N.

3. The aryl hydrocarbon receptor modulator of claim 2, wherein one of $A_1$, $A_2$ and $A_3$ is O, S or N(R), the rest two are each independently N.

4. The aryl hydrocarbon receptor modulator of claim 2, wherein when $A_3$ is N, formula (I1) turns into formula (Ia), (Ia)

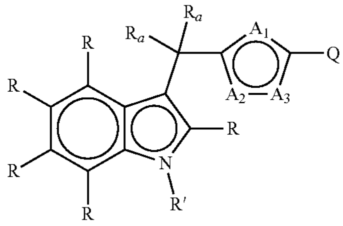

and wherein in formula (Ia), $A_1$ is O, S or N(R), $A_2$ is N; or $A_2$ is O, S or N(R), $A_1$ is N;

or when $A_2$ is CH, formula (I1) turns into formula (Ib), (Ib)

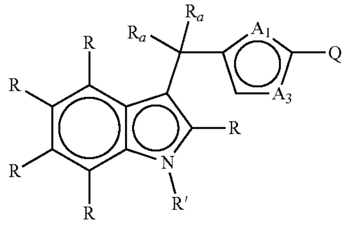

in formula (Ib), $A_1$ is N, $A_3$ is O, S or N(R); or $A_1$ is O, S or N(R), $A_3$ is N;

or when $A_1$ is N, $A_3$ is C(R) and two $R_a$ together form =N—$W_3$—$R_1$, formula (I1) turns into formula (Ic);

(Ic)

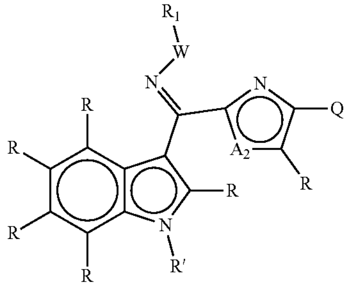

in formula (Ic), $A_2$ is O, S or N(R);

or when $A_1$ is N, $A_3$ is C(R) and two $R_a$ are H respectively, formula (I1) turns into formula (Id), (Id)

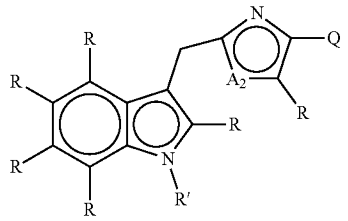

in formula (Id), $A_2$ is O or N(R);

or when $A_1$ is N, $A_3$ is C(R) and R' is

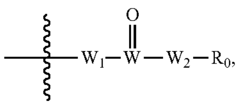

formula (I1) turns into formula (Ie), (Ie)

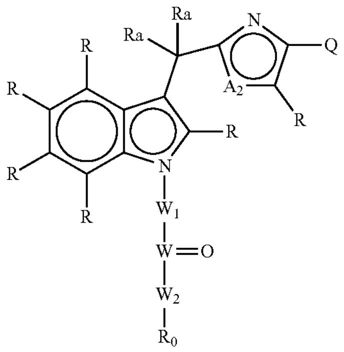

in formula (Ie), $A_2$ is O, S or N(R);

or when $A_1$ is N, $A_3$ is C(R) and R' is

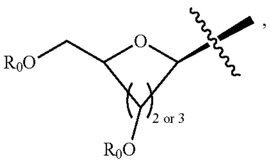

formula (I1) turns into formula (If);

(If)

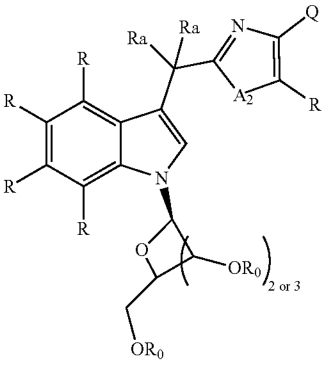

in formula (If), $A_2$ is O, S or N(R), each $R_0$ is independently H or Ac;

or when $A_1$ is N, $A_2$ is S, $A_3$ is CH and Q is a 5 membered heteroaromatic ring, formula (I1) turns into formula (Ig), formula (Ig)

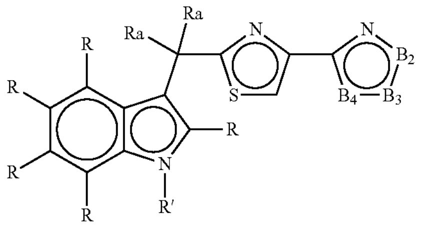

wherein one of $B_2$, $B_3$ and $B_4$ is O, S or N(R), the rest ones are each independently C(R) or N; or when $A_1$ is N, $A_2$ is S, $A_3$ is CH and Q is a 5 membered non-aromatic heterocycle containing C═N, formula (I1) turns into formula (Ih), (Ih)

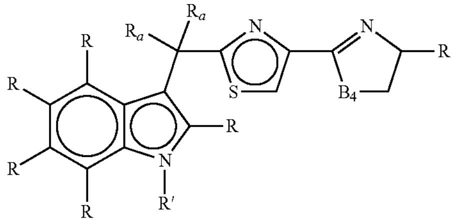

$B_4$ is O, S or N(R).

5. The aryl hydrocarbon receptor modulator of claim 1, wherein

Q is

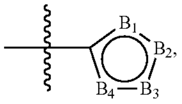

one of $B_1$, $B_2$, $B_3$ and $B_4$ is O, S or N(R), the rest three are each independently C(R) or N;

or, Q is

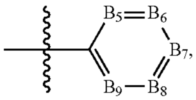

$B_5$ to $B_9$ is C(R); or one or two of $B_5$ to $B_9$ is N, the rest ones are each independently C(R).

6. The aryl hydrocarbon receptor modulator of claim 1, wherein when A is a non-aromatic heterocyclic ring with N and S heteroatom and Q is R, formula (I) turns into formula (I2), (I2)

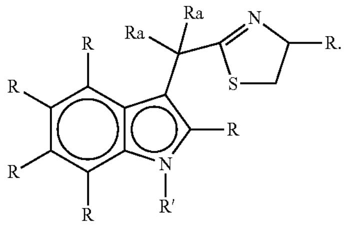

7. The aryl hydrocarbon receptor modulator of claim 1, wherein when A is

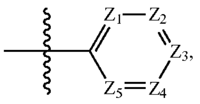

formula (I) turns into formula (I3),

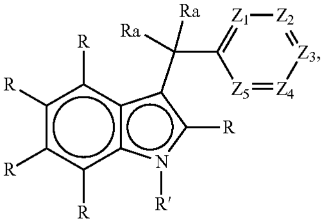

(I3)

and wherein in formula (I3), two of $Z_1$ to $Z_5$ is N, the rest ones are each independently C(Q); or, the two ones of $Z_1$ to $Z_5$ adjacent to each other are C(Q) and forms together a 5 to 6 membered heterocyclic ring containing 1 to 3 heteroatoms selected from N, O, and S, the rest three ones each are independently C(Q), or two of the rest three ones are each independently C(Q), the last one is N; or one of the rest three ones is C(Q), the rest two are independently N.

8. The aryl hydrocarbon receptor modulator of claim 1, wherein in formula (I), R' is selected from the following substituents:

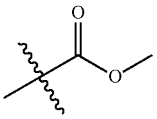 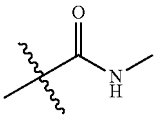

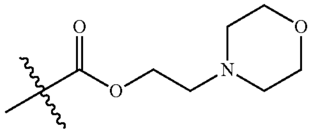

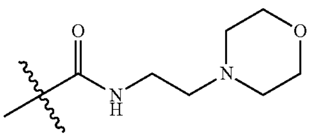 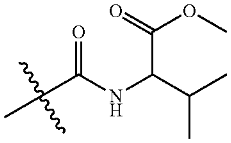

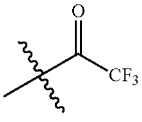 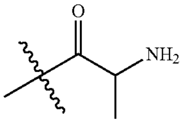 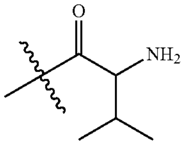

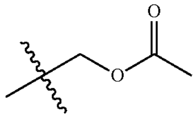 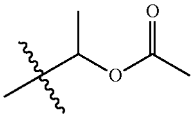

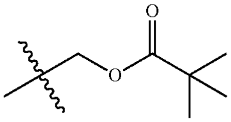 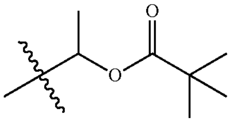

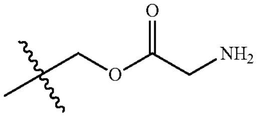 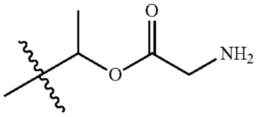

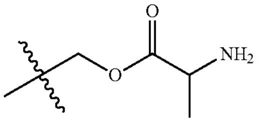 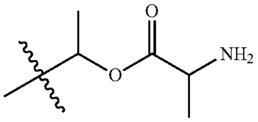

-continued

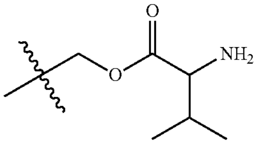 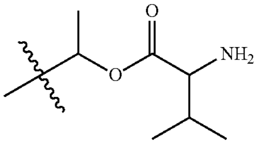

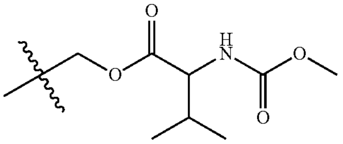

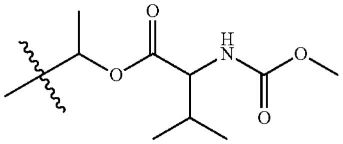 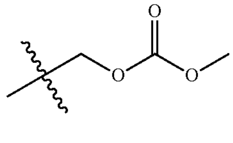

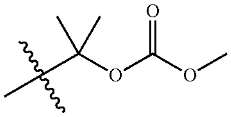 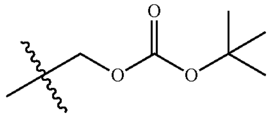

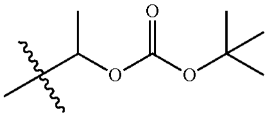 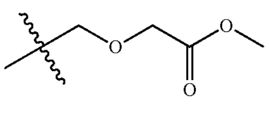

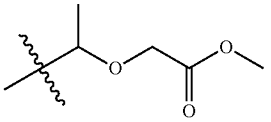 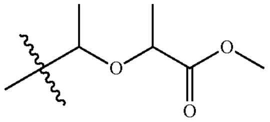

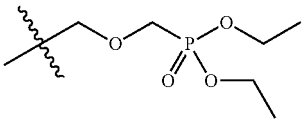 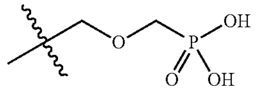

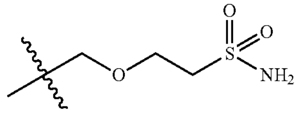

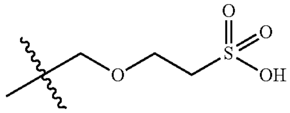

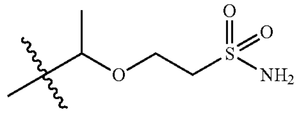

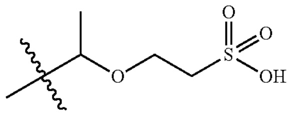

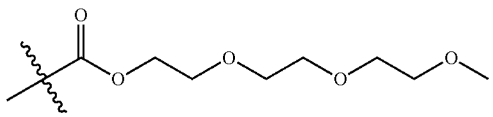

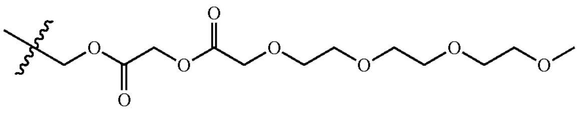

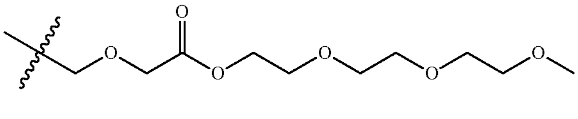

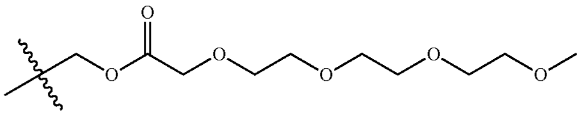
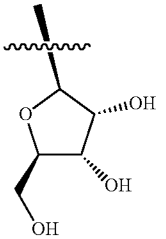
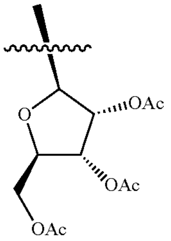
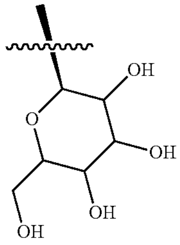
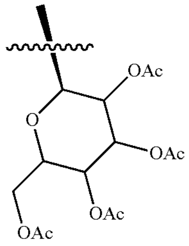
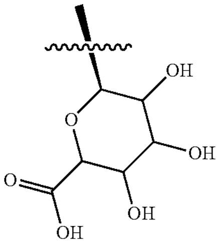
and
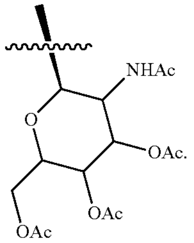
9. The aryl hydrocarbon receptor modulator of claim 3, wherein in formula (I1),
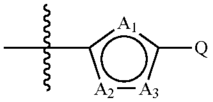
is selected from the following substituents:
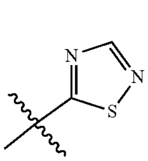
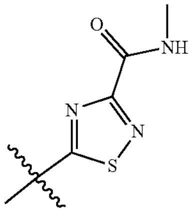
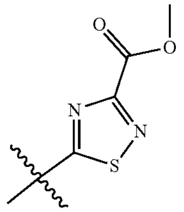
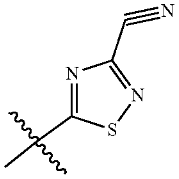
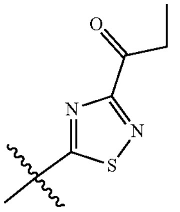
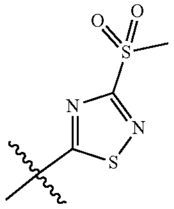
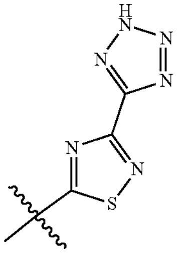
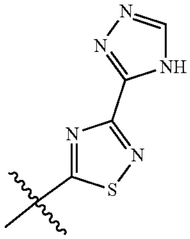
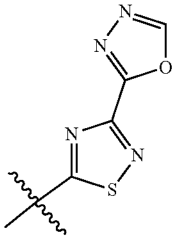
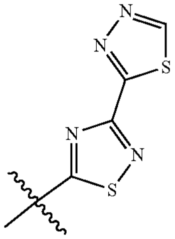
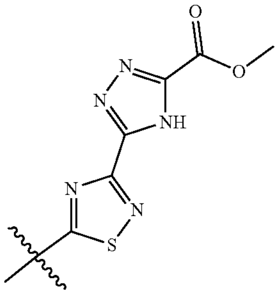
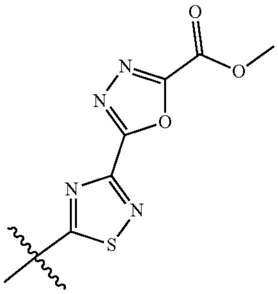
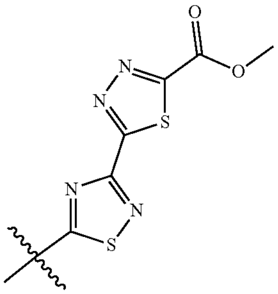
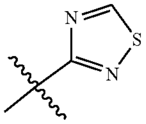
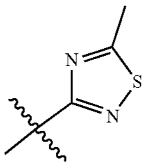
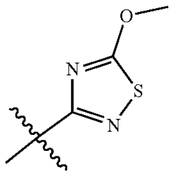
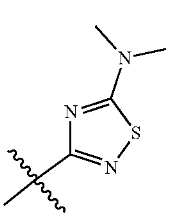
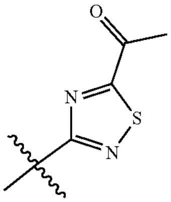
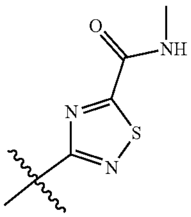
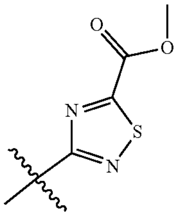
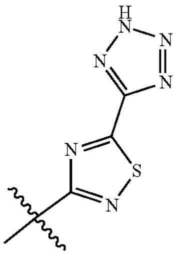
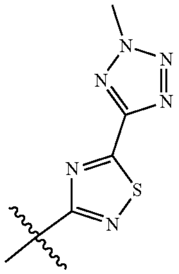

-continued
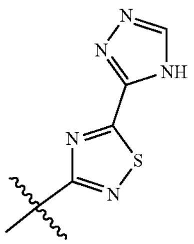
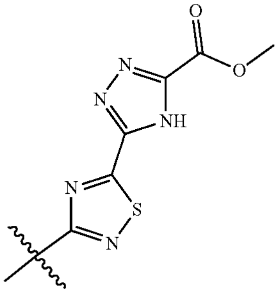
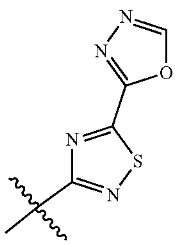
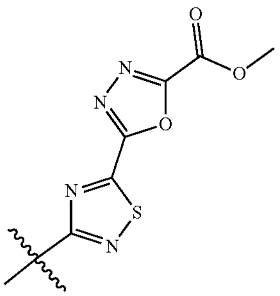
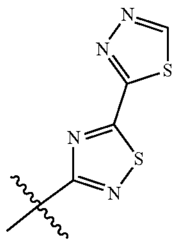
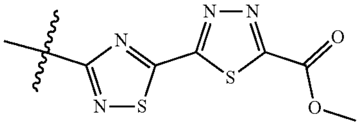
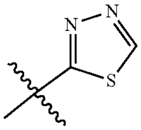
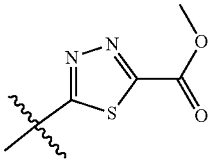
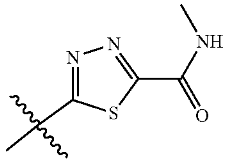
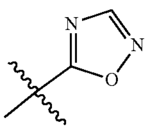
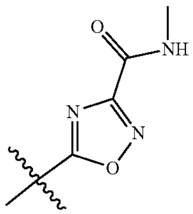
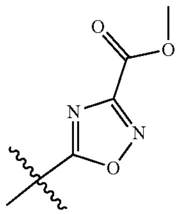
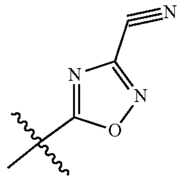
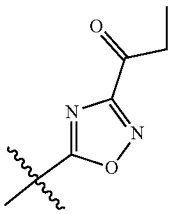
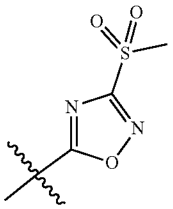
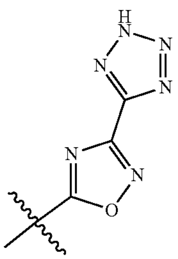
-continued
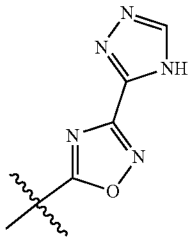
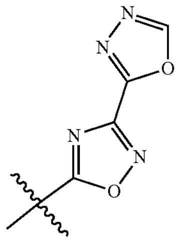
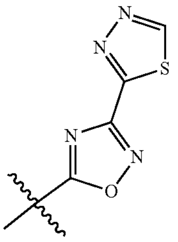
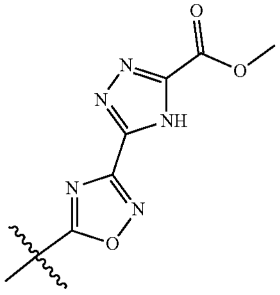
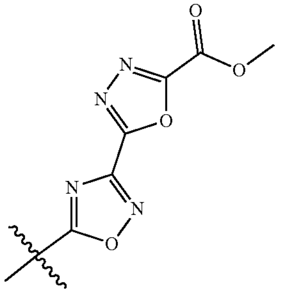
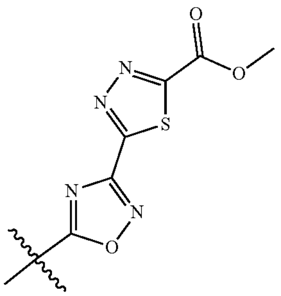
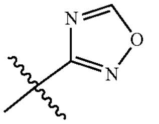
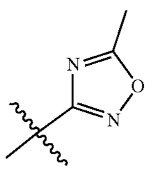
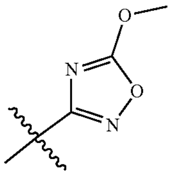
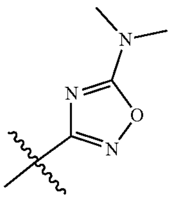
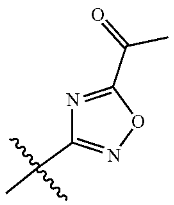
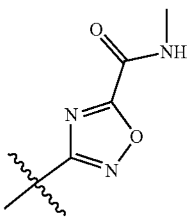
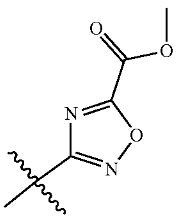
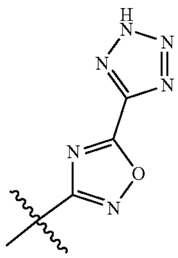
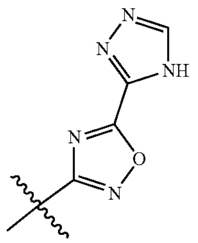
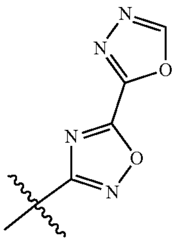

-continued
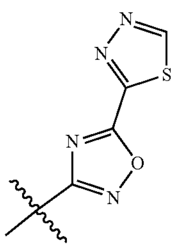
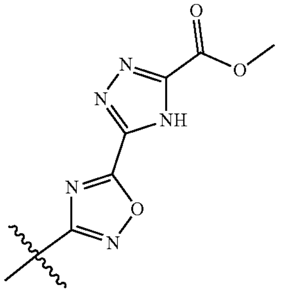
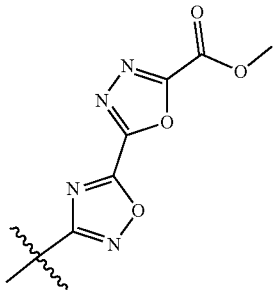
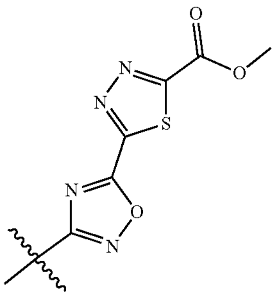
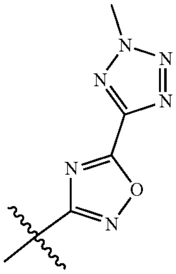
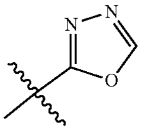
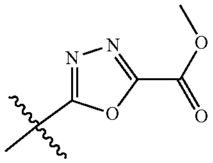
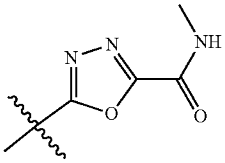
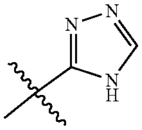
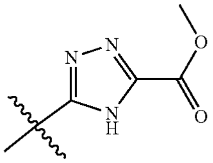
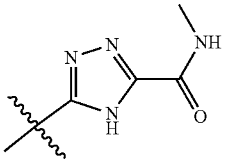
and
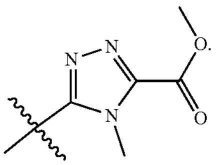
10. The aryl hydrocarbon receptor modulator of claim 4, wherein in formula (Ib),
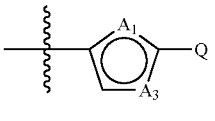
is selected from the following substituents:
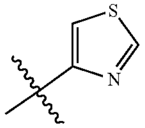
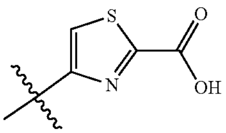
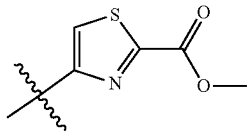
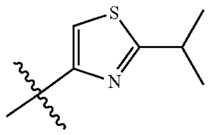
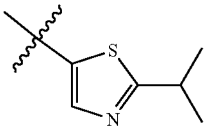
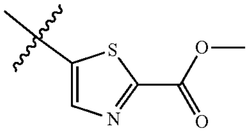
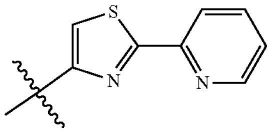
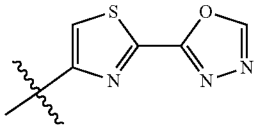
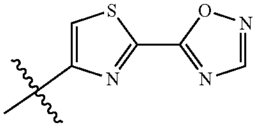 和
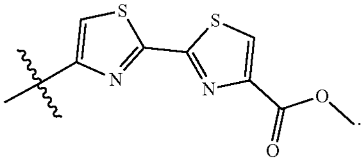
11. The aryl hydrocarbon receptor modulator of claim 4, wherein in formula (Ic) to formula (If),
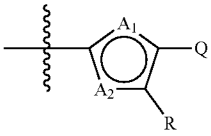
is selected from the following substituents:
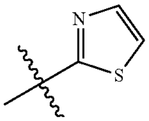
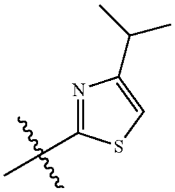
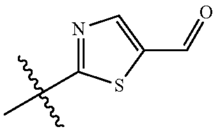
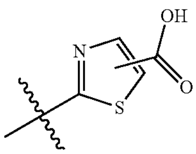
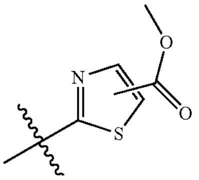

-continued
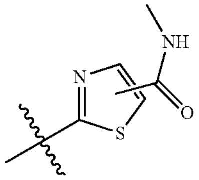
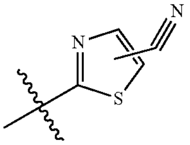
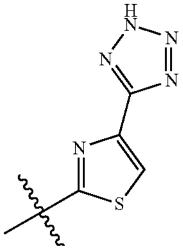
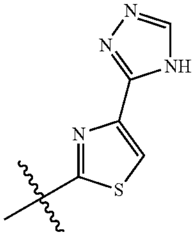
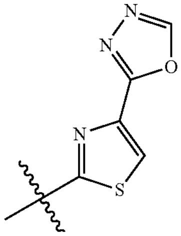
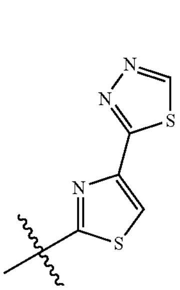
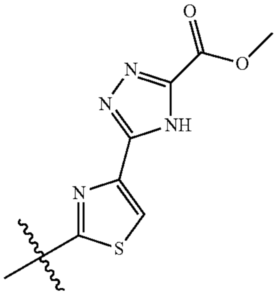
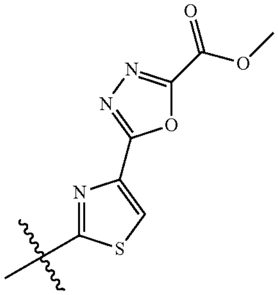
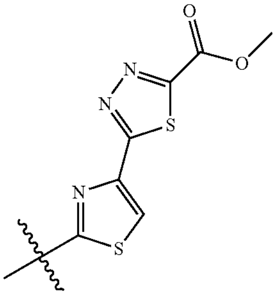
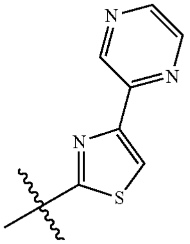
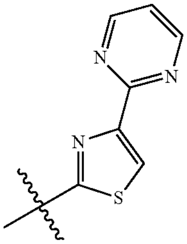
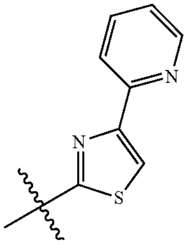
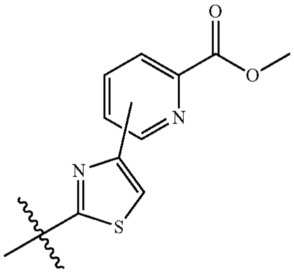
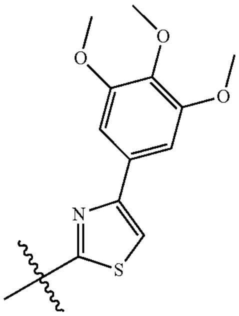
-continued
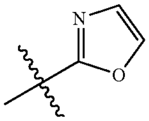
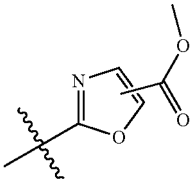
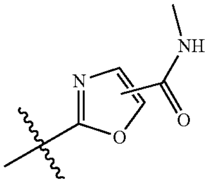
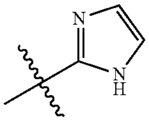
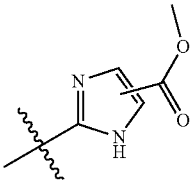
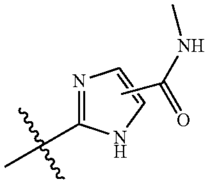
and
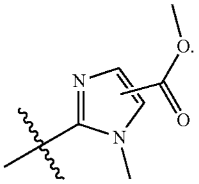
12. The aryl hydrocarbon receptor modulator of claim 1, wherein the aryl hydrocarbon receptor modulator is selected from
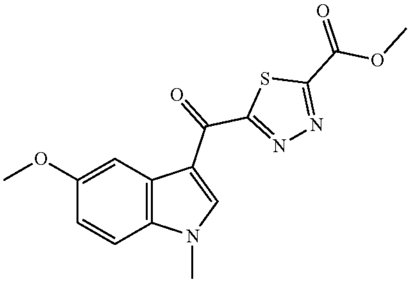
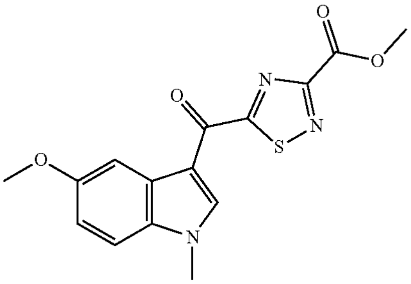
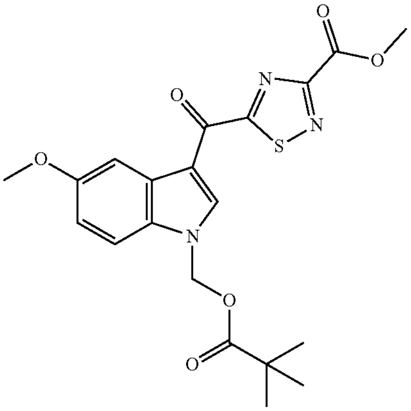

-continued
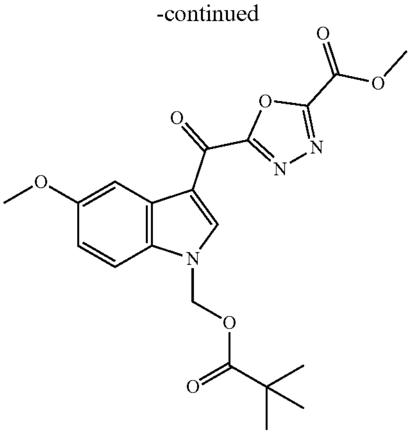
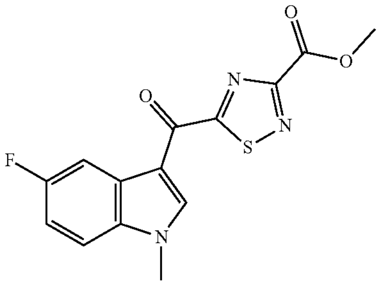
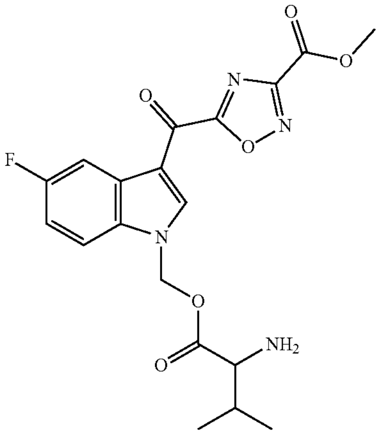
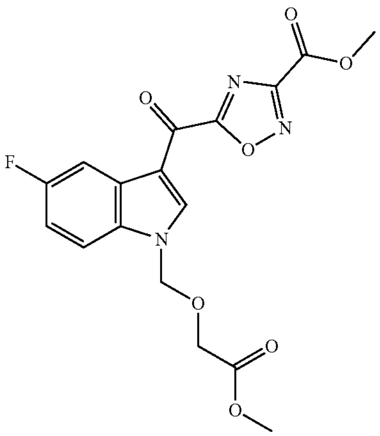
-continued
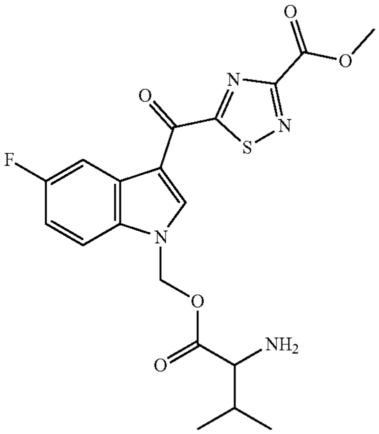
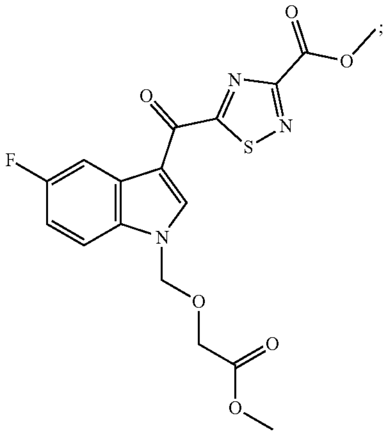
;
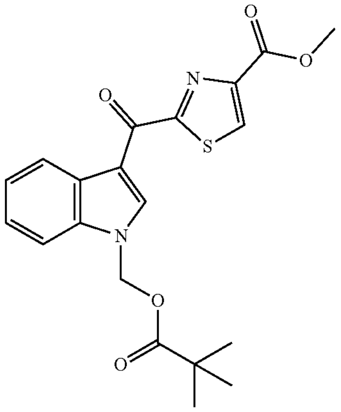
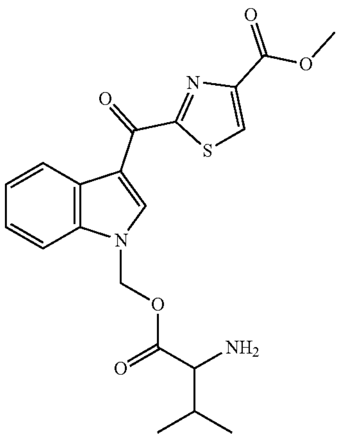

-continued
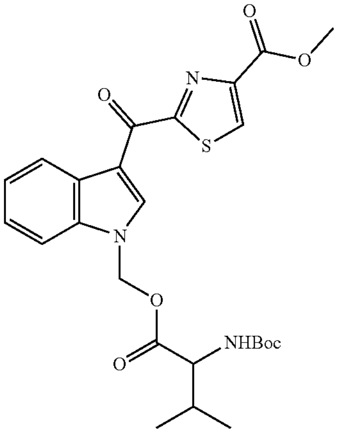
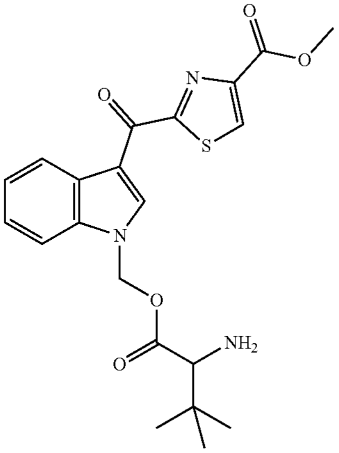
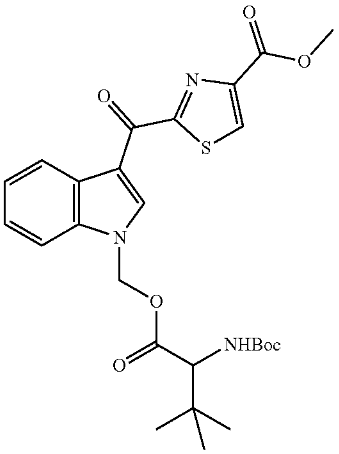
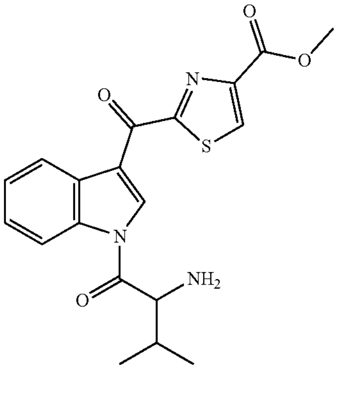
-continued
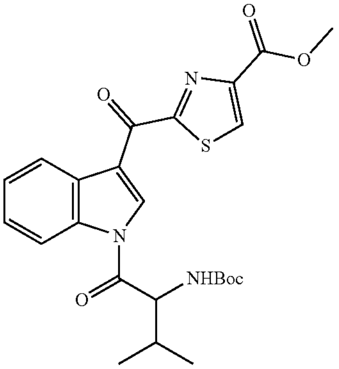
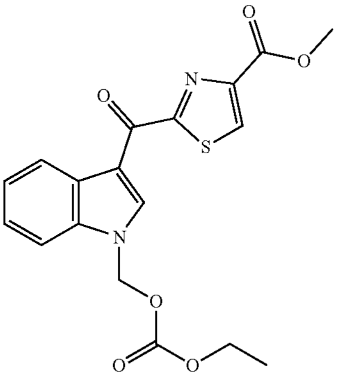
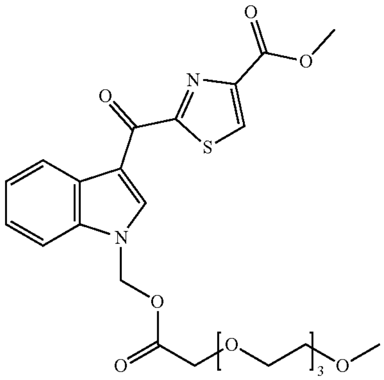
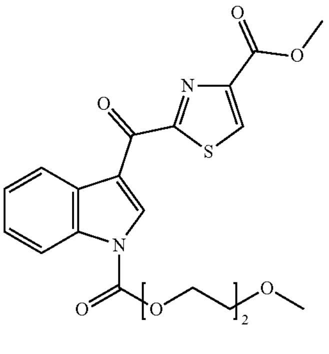

-continued
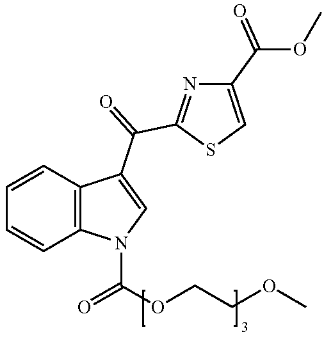
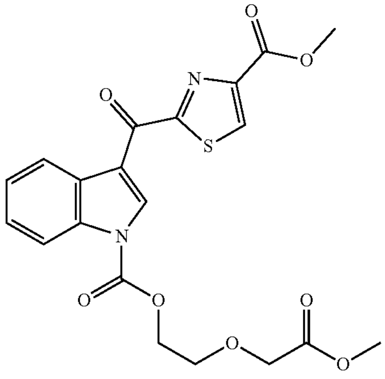
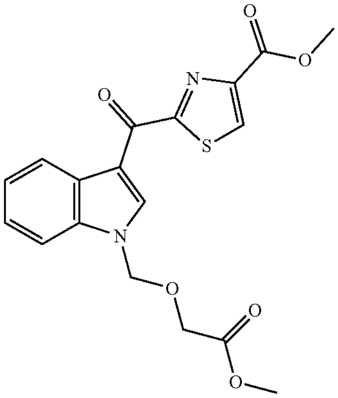
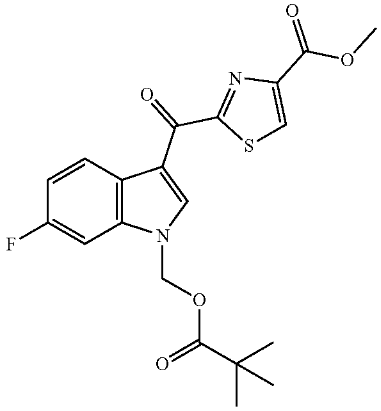
-continued
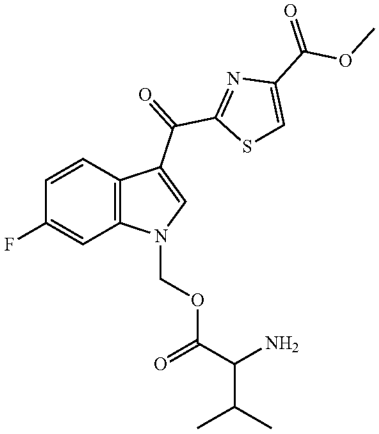
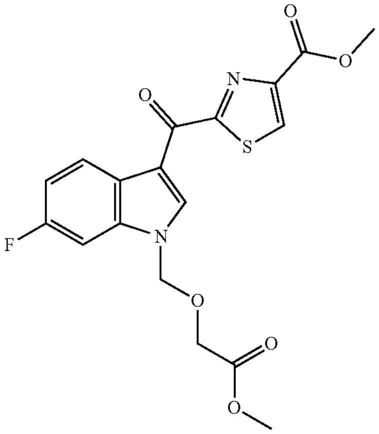
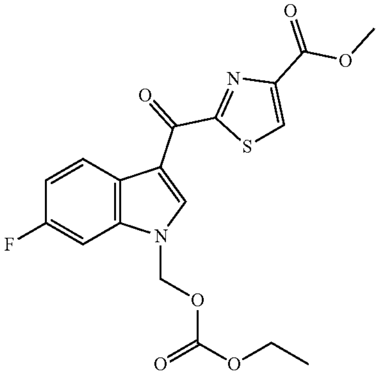
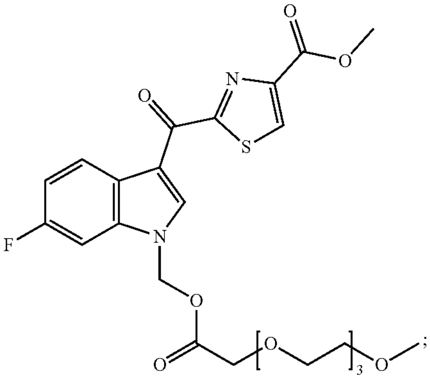

-continued
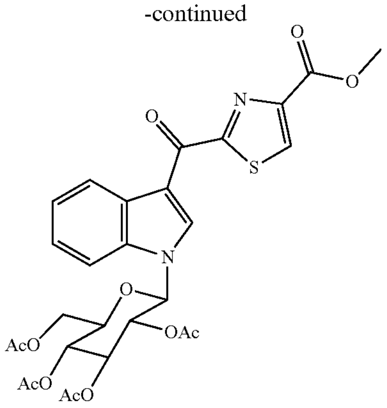
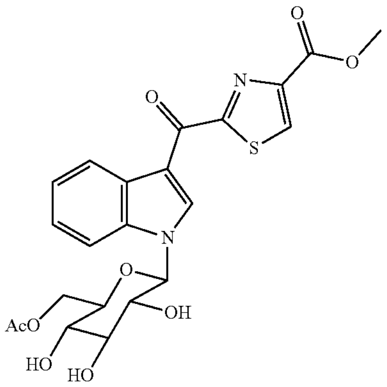
-continued
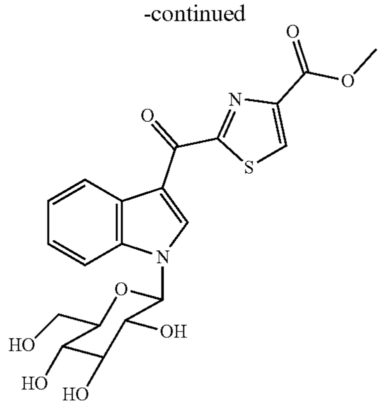
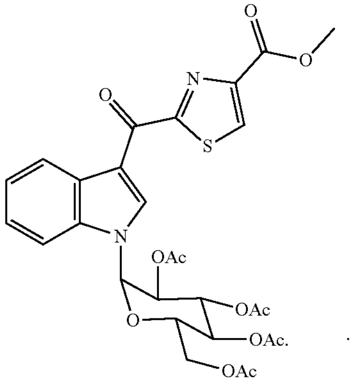 [SMILES: COC(=O)c1csc(C(=O)c2cn(C3OC(COC(C)=O)C(OC(C)=O)C(OC(C)=O)C3OC(C)=O)c3ccccc23)n1 ; "."]
13. A method of treating cancer in a patient in need thereof, comprising administering an aryl hydrocarbon receptor modulator of claim 1 to the patient.
* * * * *